United States Patent
Bravo et al.

(10) Patent No.: US 11,066,405 B2
(45) Date of Patent: *Jul. 20, 2021

(54) BICYCLIC COMPOUNDS AND THEIR USE IN THE TREATMENT OF CANCER

(71) Applicant: Tempest Therapeutics, Inc., South San Francisco, CA (US)

(72) Inventors: Yalda Bravo, San Diego, CA (US); Jason David Burch, Pointe-Claire (CA); Austin Chih-Yu Chen, San Marcos, CA (US); Joe Fred Nagamizo, San Diego, CA (US)

(73) Assignee: TEMPEST THERAPEUTICS, INC., South San Francisco, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 16/880,756

(22) Filed: May 21, 2020

(65) Prior Publication Data

US 2020/0283438 A1     Sep. 10, 2020

Related U.S. Application Data

(63) Continuation of application No. 16/605,408, filed as application No. PCT/US2018/028034 on Apr. 17, 2018.

(60) Provisional application No. 62/486,765, filed on Apr. 18, 2017.

(51) Int. Cl.
| | |
|---|---|
| *C07D 471/04* | (2006.01) |
| *C07D 209/18* | (2006.01) |
| *C07D 231/56* | (2006.01) |
| *A61P 35/00* | (2006.01) |
| *C07D 235/08* | (2006.01) |
| *C07K 16/28* | (2006.01) |

(52) U.S. Cl.
CPC ............ *C07D 471/04* (2013.01); *A61P 35/00* (2018.01); *C07D 209/18* (2013.01); *C07D 231/56* (2013.01); *C07D 235/08* (2013.01); *C07K 16/2818* (2013.01); *C07K 16/2827* (2013.01)

(58) Field of Classification Search
CPC .................................................... C07D 471/04
See application file for complete search history.

(56) References Cited

U.S. PATENT DOCUMENTS

| | | | |
|---|---|---|---|
| 8,158,671 B2* | 4/2012 | Boyd | A61P 9/10 514/412 |
| 2019/0315712 A1 | 10/2019 | Bravo et al. | |
| 2021/0008046 A1 | 1/2021 | Bravo et al. | |
| 2021/0024491 A1 | 1/2021 | Bravo et al. | |

FOREIGN PATENT DOCUMENTS

| | | | |
|---|---|---|---|
| EP | 2172447 A1 | 4/2010 | |
| EP | 2277858 A1 | 1/2011 | |
| WO | WO-2007143825 A1 | 12/2007 | |
| WO | WO-2008104055 A1 * | 9/2008 | ............... A61P 19/02 |
| WO | WO-2010121382 A1 | 10/2010 | |
| WO | WO-2018195123 A1 | 10/2018 | |
| WO | WO-2019204523 A1 | 10/2019 | |

OTHER PUBLICATIONS

Wolff, Manfred E. "Burger's Medicinal Chemistry, 5ed, Part I", John Wiley & Sons, 1995, pp. 975-977.*
Banker, G.S. et al, "Modern Pharmaceutics, 3ed.", Marcel Dekker, New York, 1996, pp. 451 and 596.*
Rautio et. al. "Prodrugs: design and clinical Applications" Nature Reviews Drug Discovery 2008, 7, 255-270.*
Beaumont "Design of Ester Prodrugs to Enhance Oral Absorption of Poorly Permeable Compounds: Challenges to the Discovery Scientist" Current Drug Metabolism, 2003, 4, 461-485.*
Prasanna "Ocular pharmacokinetics and hypotensive activity of PF-04475270, an EP4 prostaglandin agonist in preclinical models" Experimental Eye Research 89 (2009) 608-617.*
Colucci "Discovery of 4-{1-[({1-[4-(trifluoromethyl)benzyl]-1H-indol-7-yl}carbonyl) amino]cyclopropyl}benzoic acid (MF-766), a highly potent and selective EP4 antagonist for treating inflammatory pain." Bioorganic & Medicinal Chemistry Letters, 20(12), 3760-3763, 2010.*
Cancer [online], retrieved from the Internet on Jul. 6, 2007, URL: http://www.nlm.nih.gov/medlineplus/cancer.html.

(Continued)

*Primary Examiner* — David K O'Dell

(74) *Attorney, Agent, or Firm* — Wilson Sonsini Goodrich & Rosati

(57) ABSTRACT

The present disclosure is directed to novel compounds of Formula I and pharmaceutically acceptable salts, solvates, solvates of the salt and prodrugs thereof, useful in the prevention (e.g., delaying the onset of or reducing the risk of developing) and treatment (e.g., controlling, alleviating, or slowing the progression of) of cancer, including glioblastoma, bone cancer, head and neck cancer, melanoma, basal cell carcinoma, squamous cell carcinoma, adenocarcinoma, oral cancer, esophageal cancer, gastric cancer, intestinal cancer, colon cancer, bladder cancer, hepatocellular carcinoma, renal cell carcinoma, pancreatic cancer, ovarian cancer, cervical cancer, lung cancer, breast cancer, and prostate cancer. The compounds of the disclosure are selective antagonists of the EP4 receptor and useful treatment of various diseases that may be ameliorated with blockade of PGE2-mediated signaling.

16 Claims, 1 Drawing Sheet

(56) References Cited

OTHER PUBLICATIONS

Chen et al. A novel antagonist of the prostaglandin E(2) Ep(4) receptor inhibits Th1 differentiation and Th17 expansion and is orally active in arthritis models. British J. Pharmacol. 160:292 (2010).
Damasio. Alzheimer's Disease and Related Dementias. Cecil Textbook of Medicine, 20th edition, 2:1992-1996 (1996).
FDA mulls drug to slow late-stage Alzheimer's [online], [retrieved on Sep. 23, 2003]. Retrieved from the internet, URL;http;//www.cnn/com/2003/HEALTH/conditions/09/24/alzheimers.drug.ap/index.html.
Golub et al. Molecular Classification of Cancer: Class Discovery and Class Prediction by Gene Expression Monitoring. Science 286:531-537 (1999).
Lala et al. Role of nitric oxide in tumor progression: Lessons from experimental tumors. Cancer and Metastasis Reviews 17(1):91-106 (1998).
Layzer. Section Five—Degenerative Diseases of the Nervous System. Cecil Textbook of Medicine, 20th edition, 2:2050-2057 (1996).
PCT/US2018/028034 International Search Report and Written Opinion dated Jul. 6, 2018.
PCT/US2019/027992 International Search Report and Written Opinion dated Jul. 5, 2019.
U.S. Appl. No. 16/387,294 Office Action dated Mar. 25, 2020.
U.S. Appl. No. 16/387,294 Office Action dated Oct. 4, 2019.
Flesch et al. Novel prostaglandin receptor modulators—Part II: EP receptor modulators; a patent review (2002-2012). Expert Opin Ther Pat 23(2):233-267 (2013).
Marković et al. Structural features of subtype-selective EP receptor modulators. Drug Discovery Today 22(1):57-71 (2016).

\* cited by examiner

Dosing started Day0 when groups averaged 113mm^3 tumor volume

BICYCLIC COMPOUNDS AND THEIR USE IN THE TREATMENT OF CANCER

CROSS-REFERENCE

This application is a continuation of U.S. application Ser. No. 16/605,408, filed Oct. 15, 2019, which is the U.S. National Stage Entry of International Application No. PCT/US2018/028034, filed Apr. 17, 2018, which claims the benefit of U.S. Provisional Application No. 62/486,765, filed Apr. 18, 2017, each of which are hereby incorporated by reference in their entireties.

BACKGROUND OF THE INVENTION

The present disclosure is directed to heteroaryl carboxamide derivatives, pharmaceutical compositions containing such compounds, as well as methods for preventing and treating cancer using such compounds.

Prostaglandin E2 (PGE2) is an endogeneous molecule that, through its agonism of the EP4 receptor and activation of the resulting signaling cascade, has been shown to play a key role in the resolution of inflammation (Chen et al., British J. Pharmacol. 2010, 160, p. 292) and in the suppression of T cell receptor signaling (Wiemer et al., J. Immunology 2011, 187, p. 3663).

While this dampening of inflammatory response is pivotal for the prevention of excessive cellular damage following the successful mounting of an inflammatory response that has been triggered, for example, by the invasion of a foreign pathogen, it has been demonstrated that some tumors can also hijack this mechanism as a way of creating an immunosuppressive microenvironment within which tumor cells can proliferate (Whiteside, Expert Opin. Bio. Th. 2010, 10, p. 1019).

Indeed, one of the major hallmarks of an immunosuppressive tumor microenvironment is the presence of large amount of myeloid-derived suppressor cells (MDSCs) and type-2 tumor-associated macrophages (TAMs), which in turn, are significantly associated with poor overall survival in patients with gastric, ovarian, breast, bladder, hepatocellular carcinoma (HCC), head-and-neck, and other types of cancers (Qian et al., Cell. 2010, 141, p. 39; Gabitass et al., Cancer Immunol. Immunother. 2011, 60, p. 1419). Engagement of EP4 receptors on immature monocytes by PGE2, which is produced in significantly greater quantities by tumor cells (Ochs et al., J. Neurochem. 2016, 136, p. 1142; Zelenay, S. et al., Cell 2015, 162, p. 1257), have been demonstrated to skew the differentiation of these immature monocytes towards both immunosuppressive MDSC and TAM lineages (Mao, et al., Clin. Cancer Res. 2014, 20, p. 4096; Wang et al., Trends in Molecular Medicine 2016, 22, p. 1).

Furthermore, recent studies have revealed that tumor cells in some instances also mediate the upregulation of indoleamine 2,3-dioxygenase (IDO) and/or tryptophan 2,3-deoxygenase (TDO) activity in the surrounding tumor microenvironment via stimulation of the EP4 receptor by PGE2 (Ochs et al., J. Neurochem. 2016, 136, p. 1142; Hung et al., Breast Cancer Research, 2014, 16, p. 410). Since tryptophan, the substrate of the IDO and TDO enzymes, is essential for the proliferation and activation of cyototoxic Teff cells, and kyneurenine, the product of the IDO and TDO enzymes, is essential for the proliferation and activation of immunosuppressive Treg cells (Dounay et al., J. Med. Chem. 2015, 58, p. 8762), inhibition of the IDO and/or TDO activity represents a promising avenue for the treatment of various cancers (Jochems et al., Oncotarget 2016, 7, p. 37762). In fact, increased overall response rate in patients with advanced stage IIIB or IV melanoma have been reported with epacadostat, a potent and selective IDO inhibitor from Incyte, when used in combination with pembrolizumab. In light of all these observations and studies, it is therefore reasonable that antagonism of EP4 would represent a rational and efficacious approach for the treatment of advanced cancer, both as a single agent and in combination with other anti-cancer therapies.

SUMMARY OF THE INVENTION

Some embodiments provided herein describe compounds of Formula I, which are potent and selective antagonists of the EP4 receptor, pharmaceutically acceptable salts of Formula I, pharmaceutically acceptable compositions comprising such compounds, and the use of such compounds in the treatment of various diseases that may be ameliorated with the blockade of PGE2-mediated signaling, in particular cancer. For the treatment of cancer, compounds of Formula I, in some instances, are used alone or in combination with other cancer therapies, for example, radiation, antibodies to cytotoxic t-lymphocyte antigen 4 (i.e. anti-CTLA4 agents such as ipilimumab, or the like), antibodies to programmed death-ligand 1 (i.e. anti-PD-L1 agents such as atezolizumab, avelumab, or the like), antibodies to programmed cell death protein 1 (i.e. anti-PD-1 agents such as nivolumab, pembrolizumab, or the like) or cytotoxic agents (i.e. alkylating agents such as cisplatin, dacarbazine, chlorambucil, or the like; anti-metabolites such as methotrexate, fludarabine, gemcitabine, or the like; anti-microtubule agents such as vinblastine, paclitaxel, or the like; topoisomerase inhibitors such as topotecan, doxorubicin, or the like; and others). Other embodiments provided herein describe processes for the preparation of the compounds of Formula I, as well as for the preparation of intermediates used in the synthesis of the compounds described herein.

Some embodiments provided herein describe compounds of Formula I:

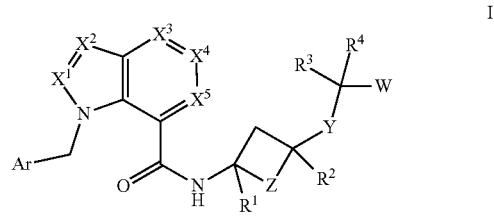

or a pharmaceutically acceptable salt, solvate, solvate of the salt, hydrate, a single stereoisomer, a mixture of stereoisomers, a racemic mixture of stereoisomers, or prodrug thereof;

wherein

Ar is an aryl or a heteroaryl, wherein said aryl and said heteroaryl are each optionally substituted with 1 to 3 substituents independently selected from: (a) $C_1$-$C_6$ alkyl, (b) $C_3$-$C_7$ cycloalkyl, (c) heterocycle, (d) aryl, (e) heteroaryl, (f) halogen, (g) CN, (h) $OR^b$, (i) $N(R^b)C(=O)R^c$, (j) $C(=O)N(R^b)(R^c)$, (k) $S(=O)_mR^b$, (l) $S(=O)_2N(R^b)(R^c)$, (m) $N(R^b)S(=O)_2R^c$, (n) $SF_5$, and (o) $C_1$-$C_6$ haloalkyl;

W is selected from: (a) $C(=O)OR^5$, (b) $C(=O)NHOH$, (c) $S(=O)_2NHR^b$, (d) $S(=O)_2NHC(=O)R^b$, (e) NHC (=O)NHSO$_2$R$^b$, (f) 1H-tetrazole, (g) 1,2,4-oxadiazol-5(4H)one, (h) 1,2,4-thiadiazol-5(4H)one, (i) 1,2,4-oxadiazole-5(4H)-thione, (j) 1,2,4-triazole-5(4H)-one, (k) tetrazol-5(4H)-one, and (l) C(=O)NHS(=O)$_2$R$^b$;

X$^1$, X$^2$, X$^3$, X$^4$, and X$^5$ are each independently N or CR$^a$, wherein not more than 2 of X$^1$, X$^2$, X$^3$, X$^4$, and X$^5$ are N;

Y is selected from: (a) a bond, (b) (CH$_2$)$_n$ wherein 1 to 4 hydrogen atoms may be replaced by R$^{a'}$, (c) O, and (d) NR$^b$;

Z is (CH$_2$)$_n$, wherein 1 to 4 hydrogen atoms may be replaced by R$^{a'}$;

R$^1$ and R$^2$ are independently selected from: (a) H, (b) C$_1$-C$_6$ alkyl, (c) C$_3$-C$_6$ cycloalkyl, and (d) C$_1$-C$_6$ haloalkyl, wherein R$^2$ is not H; or R$^1$ and R$^2$ taken together represent —(CH$_2$)$_n$—, —(CH$_2$)$_n$O(CH$_2$)$_p$—, —(CH$_2$)$_n$NR$^b$(CH$_2$)$_p$— or —(CH$_2$)$_n$S(=O)$_m$(CH$_2$)$_p$—;

R$^3$ and R$^4$ are independently selected from: (a) H, (b) C$_1$-C$_6$ alkyl, (c) C$_3$-C$_6$ cycloalkyl, (d) aryl, (e) heteroaryl, (f) halogen, (g) C$_1$-C$_6$ haloalkyl; or R$^3$ and R$^4$ taken together represent —(CH$_2$)$_n$—, —(CH$_2$)$_n$O(CH$_2$)$_p$—, —(CH$_2$)$_n$NR$^b$(CH$_2$)$_p$— or —(CH$_2$)$_n$S(=O)$_m$(CH$_2$)$_p$—;

or R$^1$, R$^2$, R$^3$ and R$^4$ above are selected as follows:

R$^1$ is selected from H, C$_1$-C$_6$ alkyl, C$_3$-C$_6$ cycloalkyl, and C$_1$-C$_6$ haloalkyl;

R$^3$ and R$^2$ taken together represent (CH$_2$)$_n$, (CH$_2$)$_n$O(CH$_2$)$_p$, (CH$_2$)$_n$NR$^b$(CH$_2$)$_p$, or (CH$_2$)$_n$S(=O)$_m$(CH$_2$)$_p$; and R$^4$ is selected from H, C$_1$-C$_6$ alkyl, C$_3$-C$_6$ cycloalkyl, aryl, heteroaryl, halogen and C$_1$-C$_6$ haloalkyl;

R$^5$ is selected from (a) H, (b) C$_1$-C$_6$ alkyl, (c) aryl, (d) aralkyl, (e) CH(R$^7$)OC(=O)R$^8$, (f) CH(R$^7$)OC(=O)OR$^8$, and (g) a (5-alkyl-2-oxo-1,3-dioxolen-4-yl)methyl group having the following formula:

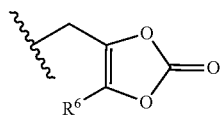

wherein R$^6$ is C$_1$-C$_6$ alkyl;

R$^7$ is hydrogen or C$_1$-C$_6$ alkyl

R$^8$ is C$_1$-C$_6$ alkyl or C$_3$-C$_6$-cycloalkyl;

R$^a$ is selected from: (a) H, (b) C$_1$-C$_6$ alkyl, (c) halogen, (d) aryl, (e) OR$^b$, (f) cyano, (g) heteroaryl, (h) C$_3$-C$_6$ cycloalkyl, and (i) C$_1$-C$_6$ haloalkyl;

R$^{a'}$ is selected from: (a) cyano, (b) C$_1$-C$_6$ alkyl, (c) halogen, (d) aryl, (e) OR$^b$, (f) heteroaryl, (g) C$_3$-C$_6$ cycloalkyl, and (h) C$_1$-C$_6$ haloalkyl;

R$^b$ and R$^c$ are independently selected from: (a) H, (b) C$_1$-C$_6$ alkyl, (c) aryl, (d) heteroaryl, (e) C$_3$-C$_6$ cycloalkyl, (f) C$_2$-C$_6$ heterocycle, or (g) C$_1$-C$_6$ haloalkyl; or R$^b$ and R$^c$ taken together with the N to which they are both attached form a 3- to 6-membered heterocycle optionally having an additional heteroatom selected from N, O and S;

m is 0, 1, or 2;

n is 1, 2 or 3; and p is 1, 2 or 3.

Some embodiments provided herein describe compounds of Formula I:

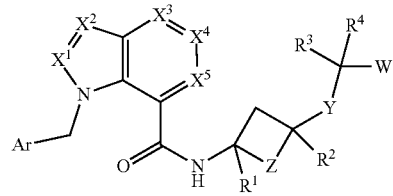

or a pharmaceutically acceptable salt, solvate, solvate of the salt, hydrate, a single stereoisomer, a mixture of stereoisomers, a racemic mixture of stereoisomers, or prodrug thereof;

wherein

Ar is an aryl or a heteroaryl, wherein said aryl and said heteroaryl are each optionally substituted with 1 to 3 substituents independently selected from: (a) C$_1$-C$_6$ alkyl, (b) C$_3$-C$_7$ cycloalkyl, (c) heterocycle, (d) aryl, (e) heteroaryl, (f) halogen, (g) CN, (h) OR$^b$, (i) N(R$^b$)C(=O)R$^c$, (j) C(=O)N(R$^b$)(R$^c$), (k) S(=O)$_m$R$^b$, (l) S(=O)$_2$N(R$^b$)(R$^c$), (m) N(R$^b$)S(=O)$_2$R$^c$, (n) SF$_5$, and (o) C$_1$-C$_6$ haloalkyl;

W is selected from: (a) C(=O)OR$^5$, (b) C(=O)NHOH, (c) S(=O)$_2$NHR$^b$, (d) S(=O)$_2$NHC(=O)R$^b$, (e) NHC(=O)NHSO$_2$R$^b$, (f) 1H-tetrazole, (g) 1,2,4-oxadiazol-5(4H)one, (h) 1,2,4-thiadiazol-5(4H)one, (i) 1,2,4-oxadiazole-5(4H)-thione, (j) 1,2,4-triazole-5(4H)-one, (k) tetrazol-5(4H)-one, and (l) C(=O)NHS(=O)$_2$R$^b$;

X$^1$, X$^2$, X$^3$, X$^4$, and X$^5$ are each independently N or CR$^a$, wherein not more than 2 of X$^1$, X$^2$, X$^3$, X$^4$, and X$^5$ are N;

Y is selected from: (a) a bond, (b) (CH$_2$)$_n$ wherein 1 to 4 hydrogen atoms may be replaced by R$^{a'}$, (c) O, and (d) NR$^b$;

Z is (CH$_2$)$_n$, wherein 1 to 4 hydrogen atoms may be replaced by R$^{a'}$;

R$^1$ and R$^2$ are independently selected from: (a) H, (b) C$_1$-C$_6$ alkyl, (c) C$_3$-C$_6$ cycloalkyl, and (d) C$_1$-C$_6$ haloalkyl, wherein R$^2$ is not H; or R$^1$ and R$^2$ taken together represent —(CH$_2$)$_n$—, —(CH$_2$)$_n$O(CH$_2$)$_p$—, —(CH$_2$)$_n$NR$^b$(CH$_2$)$_p$— or —(CH$_2$)$_n$S(=O)$_m$(CH$_2$)$_p$—;

R$^3$ and R$^4$ are independently selected from: (a) H, (b) C$_1$-C$_6$ alkyl, (c) C$_3$-C$_6$ cycloalkyl, (d) aryl, (e) heteroaryl, (f) halogen, (g) C$_1$-C$_6$ haloalkyl; or R$^3$ and R$^4$ taken together represent —(CH$_2$)$_n$—, —(CH$_2$)$_n$O(CH$_2$)$_p$—, —(CH$_2$)$_n$NR$^b$(CH$_2$)$_p$— or —(CH$_2$)$_n$S(=O)$_m$(CH$_2$)$_p$—;

or R$^1$, R$^2$, R$^3$ and R$^4$ above are selected as follows:

R$^1$ is selected from H, C$_1$-C$_6$ alkyl, C$_3$-C$_6$ cycloalkyl, and C$_1$-C$_6$ haloalkyl;

R$^3$ and R$^2$ taken together represent (CH$_2$)$_n$, (CH$_2$)$_n$O(CH$_2$)$_p$, (CH$_2$)$_n$NR$^b$(CH$_2$)$_p$, or (CH$_2$)$_n$S(=O)$_m$(CH$_2$)$_p$; and R$^4$ is selected from H, C$_1$-C$_6$ alkyl, C$_3$-C$_6$ cycloalkyl, aryl, heteroaryl, halogen and C$_1$-C$_6$ haloalkyl;

R$^5$ is selected from (a) H, (b) C$_1$-C$_6$ alkyl, (c) aryl, (d) aralkyl, (e) CH(R$^7$)OC(=O)R$^8$, (f) CH(R$^7$)OC(=O)OR$^8$, and (g) a (5-alkyl-2-oxo-1,3-dioxolen-4-yl)methyl group having the following formula:

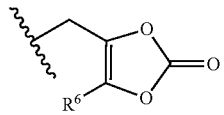

wherein $R^6$ is $C_1$-$C_6$ alkyl;

$R^7$ is hydrogen or $C_1$-$C_6$ alkyl;

$R^8$ is $C_1$-$C_6$ alkyl or $C_3$-$C_6$-cycloalkyl;

$R^a$ is selected from: (a) H, (b) $C_1$-$C_6$ alkyl, (c) halogen, (d) aryl, (e) $OR^b$, (f) cyano, (g) heteroaryl, (h) $C_3$-$C_6$ cycloalkyl, and (i) $C_1$-$C_6$ haloalkyl;

$R^{a'}$ is selected from: (a) cyano, (b) $C_1$-$C_6$ alkyl, (c) halogen, (d) aryl, (e) $OR^b$, (f) heteroaryl, (g) $C_3$-$C_6$ cycloalkyl, and (h) $C_1$-$C_6$ haloalkyl;

$R^b$ and $R^c$ are independently selected from: (a) H, (b) $C_1$-$C_6$ alkyl, (c) aryl, (d) heteroaryl, (e) $C_3$-$C_6$ cycloalkyl, or (f) $C_1$-$C_6$ haloalkyl; or $R^b$ and $R^c$ taken together with the N to which they are both attached form a 3- to 6-membered heterocycle optionally having an additional heteroatom selected from N, O and S;

m is 0, 1, or 2;

n is 1, 2 or 3; and p is 1, 2 or 3.

In some embodiments, Ar is an aryl or a heteroaryl, wherein said aryl and said heteroaryl are each optionally substituted with 1 to 3 substituents independently selected from the group consisting of:
(a) $C_1$-$C_6$ alkyl,
(b) $C_3$-$C_7$ cycloalkyl,
(c) heterocycle,
(d) aryl,
(e) heteroaryl,
(f) halogen,
(g) CN,
(h) $OR^b$,
(i) $N(R^b)C(=O)R^c$,
(j) $C(=O)N(R^b)(R^c)$,
(k) $S(=O)_m R^b$,
(l) $S(=O)_2 N(R^b)(R^c)$,
(m) $N(R^b)S(=O)_2 R^c$,
(n) $SF_5$ and
(o) $C_1$-$C_6$ haloalkyl.

In some embodiments, W is selected from the group consisting of:
(a) $CO_2H$,
(b) $C(=O)NHOH$,
(c) $S(=O)_2 NHR^b$,
(d) $S(=O)_2 NHC(=O)R^b$,
(e) $NHC(=O)NHSO_2 R^b$,
(f) 1H-tetrazole,
(g) 1,2,4-oxadiazol-5(4H)one,
(h) 1,2,4-thiadiazol-5(4H)one,
(i) 1,2,4-oxadiazole-5(4H)-thione,
(j) 1,2,4-triazole-5(4H)-one,
(k) tetrazol-5(4H)-one, and
(l) $C(=O)NHS(=O)_2 R^b$.

In some embodiments, $X^1$, $X^2$, $X^3$, $X^4$, and $X^5$ are each independently N or $CR^a$, wherein not more than 2 of $X^1$, $X^2$, $X^3$, $X^4$, and $X^5$ are N.

In some embodiments, Y is selected from: (a) a bond, (b) $(CH_2)_n$ wherein 1 to 4 hydrogen atoms may be replaced by $R^{a'}$, (c) O, and (d) $NR^b$.

In some embodiments, Z is $(CH_2)_n$, wherein 1 to 4 hydrogen atoms may be replaced by $R^{a'}$.

In some embodiments, $R^1$ and $R^2$ are independently selected from:
(a) H,
(b) $C_1$-$C_6$ alkyl,
(c) $C_3$-$C_6$ cycloalkyl, and
(d) $C_1$-$C_6$ haloalkyl.

In some embodiments, $R^1$ and $R^2$ are not both H.

In some embodiments, $R^1$ and $R^2$ taken together represent $-(CH_2)_n-$, $-(CH_2)_n O(CH_2)_p-$, $-(CH_2)_n NR^b(CH_2)_p-$ or $-(CH_2)_n S(=O)_m(CH_2)_p-$.

In some embodiments, $R^3$ and $R^4$ are independently selected from the group consisting of:
(a) H,
(b) $C_1$-$C_6$ alkyl,
(c) $C_3$-$C_6$ cycloalkyl,
(d) aryl,
(e) heteroaryl,
(f) halogen, and
(g) $C_1$-$C_6$ haloalkyl.

In some embodiments, $R^3$ and $R^4$ taken together represent $-(CH_2)_n-$, $-(CH_2)_n O(CH_2)_p-$, $-(CH_2)_n NR^b(CH_2)_p-$ or $-(CH_2)_n S(=O)_m(CH_2)_p-$.

In some embodiments, $R^3$ and $R^2$ taken together represent $(CH_2)_n$, $(CH_2)_n O(CH_2)_p$, $(CH_2)_n NR^b(CH_2)_p$, or $(CH_2)_n S(=O)_m(CH_2)_p$.

In some embodiments, $R^a$ is selected from the group consisting of:
(a) H,
(b) $C_1$-$C_6$ alkyl,
(c) halogen,
(d) aryl,
(e) $OR^b$,
(f) cyano,
(g) heteroaryl,
(h) $C_3$-$C_6$ cycloalkyl, and
(i) $C_1$-$C_6$ haloalkyl.

In some embodiments, $R^{a'}$ is selected from the group consisting of:
(a) cyano,
(b) $C_1$-$C_6$ alkyl,
(c) halogen,
(d) aryl,
(e) $OR^b$,
(f) heteroaryl,
(g) $C_3$-$C_6$ cycloalkyl, and
(h) $C_1$-$C_6$ haloalkyl.

In some embodiments, $R^b$ and $R^c$ are independently selected from the group consisting of:
(a) H,
(b) $C_1$-$C_6$ alkyl,
(c) aryl,
(d) heteroaryl,
(e) $C_3$-$C_6$ cycloalkyl, and
(f) $C_1$-$C_6$ haloalkyl.

In some embodiments, $R^b$ and $R^c$ taken together with the N to which they are both attached form a 3- to 6-membered heterocycle optionally having an additional heteroatom selected from N, O and S.

In some embodiments, m is 0, 1, or 2.

In some embodiments, n is 1, 2 or 3.

In some embodiments, p is 1, 2 or 3.

In some embodiments, Ar is phenyl optionally substituted with 1 to 3 substituents independently selected from:
(a) halogen,
(b) cyano,
(c) $C_1$-$C_6$ alkyl,
(d) $SF_5$, (e) $C_1$-$C_6$ haloalkyl,
(f) $OR^b$ wherein $R^b$ is $C_1$-$C_6$ alkyl, aryl, heteroaryl, $C_3$-$C_6$ cycloalkyl or $C_1$-$C_6$ haloalkyl,
(g) heterocycle,
(h) aryl, and
(i) heteroaryl.

In some embodiments, Ar is phenyl optionally substituted with 1 to 3 substituents independently selected from:
(a) halogen,
(b) cyano,
(c) $C_1$-$C_6$ alkyl,
(d) $SF_5$, and
(e) $C_1$-$C_6$ haloalkyl.

In some embodiments, each of $X^1$, $X^2$, $X^3$, $X^4$ and $X^5$ is independently C—$R^a$. In some embodiments, one of $X^1$, $X^2$, $X^3$, $X^4$ and $X^5$ is N, and the others are each independently C—$R^a$. In some embodiments, each of $X^1$, $X^2$, $X^3$, $X^4$ and $X^5$ is independently C—$R^a$. In some embodiments, $R^a$ is H or a halogen atom.

In some embodiments, W is selected from the group consisting of: (a) $CO_2H$ and (b) 1H-tetrazole.

In some embodiments, Z is —$CH_2$—.

In some embodiments, Y is a bond or —$CH_2$—.

In some embodiments, $R^1$ and $R^2$ taken together represent —$CH_2$— or —$CH_2CH_2$—.

In some embodiments, Y is —$CH_2$—, and $R^3$ and $R^2$ taken together represent —$CH_2$— or —$CH_2CH_2$—.

Some embodiments provided herein describe a compound of Formula I having the structure of Formula Ia:

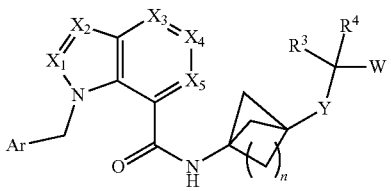

Ia or a pharmaceutically acceptable salt, solvate, solvate of the salt, hydrate, a single stereoisomer, a mixture of stereoisomers, a racemic mixture of stereoisomers, or prodrug thereof.

In some embodiments, Ar is phenyl optionally substituted with 1 to 3 substituents independently selected from:
(a) halogen,
(b) cyano,
(c) $C_1$-$C_6$ alkyl,
(d) $SF_5$,
(e) $C_1$-$C_6$ haloalkyl,
(f) $OR^b$ wherein $R^b$ is $C_1$-$C_6$ alkyl, aryl, heteroaryl, $C_3$-$C_6$ cycloalkyl or $C_1$-$C_6$ haloalkyl,
(g) heterocycle,
(h) aryl, and
(i) heteroaryl.

In some embodiments, Ar is phenyl optionally substituted with 1 to 3 substituents independently selected from:
(a) halogen,
(b) cyano,
(c) $C_1$-$C_6$ alkyl,
(d) $SF_5$, and
(e) $C_1$-$C_6$ haloalkyl.

In some embodiments, each of $X^1$, $X^2$, $X^3$, $X^4$ and $X^5$ is independently C—$R^a$. In some embodiments, one of $X^1$, $X^2$, $X^3$, $X^4$ and $X^5$ is N, and the others are each independently C—$R^a$.

In some embodiments, W is selected from the group consisting of: (a) $CO_2H$ and (b) 1H-tetrazole.

In some embodiments, Y is a bond or —$CH_2$—.

In some embodiments, n is 1 or 2.

In some embodiments, $R^3$ and $R^4$ are independently selected from the group consisting of: (a) H, (b) $C_1$-$C_3$ alkyl, and (c) $C_1$-$C_3$ haloalkyl.

In some embodiments, $R^a$ is selected from the group consisting of H and halogen.

In some embodiments, Y is a bond, and n is 1.

Some embodiments provided herein describe a compound of Formula I having the structure of Formula Ib:

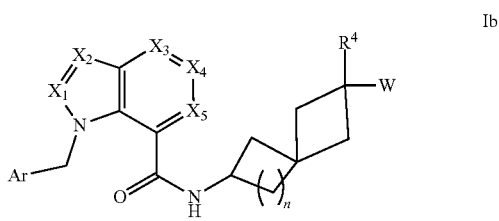

Ib or a pharmaceutically acceptable salt, solvate, solvate of the salt, hydrate, a single stereoisomer, a mixture of stereoisomers, a racemic mixture of stereoisomers, or prodrug thereof.

In some embodiments, Ar is phenyl optionally substituted with 1 to 3 substituents independently selected from:
(a) halogen,
(b) cyano,
(c) $C_1$-$C_6$ alkyl,
(d) $SF_5$,
(e) $C_1$-$C_6$ haloalkyl,
(f) $OR^b$ wherein $R^b$ is $C_1$-$C_6$ alkyl, aryl, heteroaryl, $C_3$-$C_6$ cycloalkyl or $C_1$-$C_6$ haloalkyl,
(g) heterocycle,
(h) aryl, and
(i) heteroaryl.

In some embodiments, Ar is phenyl optionally substituted with 1 to 3 substituents independently selected from:
(a) halogen,
(b) cyano,
(c) $C_1$-$C_6$ alkyl,
(d) $SF_5$, and
(e) $C_1$-$C_6$ haloalkyl.

In some embodiments, each $X^1$, $X^2$, $X^3$, $X^4$ and $X^5$ is independently C—$R^a$, or one of $X^1$, $X^2$, $X^3$, $X^4$ and $X^5$ is N, and the others are each independently C—$R^a$.

In some embodiments, W is selected from the group consisting of: (a) $CO_2H$ and (b) 1H-tetrazole.

In some embodiments, n is 1 or 2.

In some embodiments, $R^4$ is selected from the group consisting of: (a) H, (b) $C_1$-$C_3$, and (c) $C_1$-$C_3$ haloalkyl.

In some embodiments, $R^a$ is selected from the group consisting of H and halogen.

In some embodiments, n is 1.

Some embodiments provided herein describe a compound of Formula I having the Formula Ic or Id:

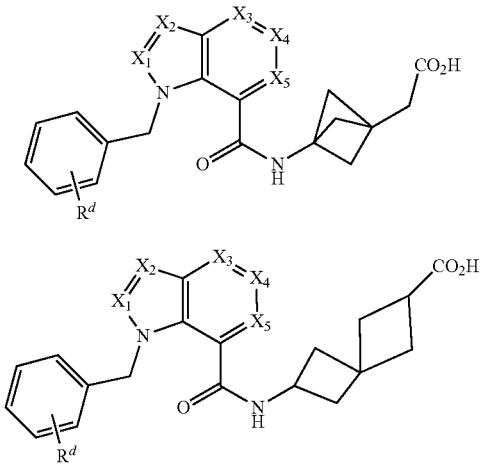

or a pharmaceutically acceptable salt, solvate, solvate of the salt, hydrate, a single stereoisomer, a mixture of stereoisomers, a racemic mixture of stereoisomers, or prodrug thereof.

In some embodiments, each $X^1$, $X^2$, $X^3$, $X^4$ and $X^5$ is independently C—$R^a$.

In some embodiments, one of $X^1$, $X^2$, $X^3$, $X^4$ and $X^5$ is N, and the others are each independently C—$R^a$.

In some embodiments, $R^a$ is selected from the group consisting of H and halogen.

In some embodiments, $R^d$ is selected from:
(a) CN,
(b) $C_1$-$C_3$ alkyl,
(c) $SF_5$,
(d) $C_1$-$C_3$ haloalkyl,
(e) $OR^b$ wherein $R^b$ is $C_1$-$C_6$ alkyl, aryl, heteroaryl, $C_3$-$C_6$ cycloalkyl or $C_1$-$C_6$ haloalkyl,
(f) heterocycle,
(g) aryl, and
(h) heteroaryl.

In some embodiments, $R^d$ is selected from the group consisting of: (a) CN, (b) $C_1$-$C_3$ alkyl, (c) $SF_5$, and (d) $C_1$-$C_3$ haloalkyl.

In some embodiments, each $X^1$, $X^2$, $X^3$, $X^4$ and $X^5$ is CH; or one of $X^1$, $X^2$, $X^3$, $X^4$ and $X^5$ is C—$R^a$ and the others are CH, and $R^a$ is halogen.

In some embodiments, the compound is selected from:
2-(3-(1-(4-cyanobenzyl)-1H-indole-7-carboxamido)bicyclo[1.1.1]pentan-1-yl)acetic acid;
2-(3-(1-(4-(trifluoromethyl)benzyl)-1H-indole-7-carboxamido)bicyclo[1.1.1]pentan-1-yl)acetic acid;
2-(3-(1-(4-(trifluoromethyl)benzyl)-1H-pyrrolo[3,2-b]pyridine-7-carboxamido)bicyclo[1.1.1]pentan-1-yl)acetic acid;
2-(3-(1-(4-(trifluoromethyl)benzyl)-1H-pyrrolo[3,2-c]pyridine-7-carboxamido)bicyclo[1.1.1]pentan-1-yl)acetic acid;
2-(3-(1-(4-(trifluoromethyl)benzyl)-1H-pyrrolo[2,3-c]pyridine-7-carboxamido)bicyclo[1.1.1]pentan-1-yl)acetic acid;
2-(3-(1-(4-(trifluoromethyl)benzyl)-1H-indazole-7-carboxamido)bicyclo[1.1.1]pentan-1-yl)acetic acid;
2-(3-(1-((4-(trifluoromethyl)phenyl)methyl-$d_2$)-1H-indole-7-carboxamido)bicyclo[1.1.1]pentan-1-yl)acetic acid;
6-(1-(4-(trifluoromethyl)benzyl)-1H-indole-7-carboxamido)spiro[3.3]heptane-2-carboxylic acid;
(R)-6-(1-(4-(trifluoromethyl)benzyl)-1H-indole-7-carboxamido)spiro[3.3]heptane-2-carboxylic acid;
(S)-6-(1-(4-(trifluoromethyl)benzyl)-1H-indole-7-carboxamido)spiro[3.3]heptane-2-carboxylic acid;
6-(1-(4-(trifluoromethyl)benzyl)-1H-pyrrolo[3,2-b]pyridine-7-carboxamido)spiro[3.3]heptane-2-carboxylic acid;
(R)-6-(1-(4-(trifluoromethyl)benzyl)-1H-pyrrolo[3,2-b]pyridine-7-carboxamido)spiro[3.3]heptane-2-carboxylic acid;
(S)-6-(1-(4-(trifluoromethyl)benzyl)-1H-pyrrolo[3,2-b]pyridine-7-carboxamido)spiro[3.3]heptane-2-carboxylic acid;
6-(1-(4-(trifluoromethyl)benzyl)-1H-pyrrolo[3,2-c]pyridine-7-carboxamido)spiro[3.3]heptane-2-carboxylic acid;
(R)-6-(1-(4-(trifluoromethyl)benzyl)-1H-pyrrolo[3,2-c]pyridine-7-carboxamido)spiro[3.3]heptane-2-carboxylic acid;
(S)-6-(1-(4-(trifluoromethyl)benzyl)-1H-pyrrolo[3,2-c]pyridine-7-carboxamido)spiro[3.3]heptane-2-carboxylic acid;
6-(1-(4-(trifluoromethyl)benzyl)-1H-pyrrolo[2,3-c]pyridine-7-carboxamido)spiro[3.3]heptane-2-carboxylic acid;
(R)-6-(1-(4-(trifluoromethyl)benzyl)-1H-pyrrolo[2,3-c]pyridine-7-carboxamido)spiro[3.3]heptane-2-carboxylic acid;
(S)-6-(1-(4-(trifluoromethyl)benzyl)-1H-pyrrolo[2,3-c]pyridine-7-carboxamido)spiro[3.3]heptane-2-carboxylic acid;
6-(1-(4-(trifluoromethyl)benzyl)-1H-indazole-7-carboxamido)spiro[3.3]heptane-2-carboxylic acid;
(R)-6-(1-(4-(trifluoromethyl)benzyl)-1H-indazole-7-carboxamido)spiro[3.3]heptane-2-carboxylic acid;
(S)-6-(1-(4-(trifluoromethyl)benzyl)-1H-indazole-7-carboxamido)spiro[3.3]heptane-2-carboxylic acid;
6-(1-(4-(trifluoromethyl)benzyl)-1H-benzo[d]imidazole-7-carboxamido)spiro[3.3]heptane-2-carboxylic acid;
(R)-6-(1-(4-(trifluoromethyl)benzyl)-1H-benzo[d]imidazole-7-carboxamido)spiro[3.3]heptane-2-carboxylic acid;
(S)-6-(1-(4-(trifluoromethyl)benzyl)-1H-benzo[d]imidazole-7-carboxamido)spiro[3.3]heptane-2-carboxylic acid;
3-(3-(1-(4-(trifluoromethyl)benzyl)-1H-indole-7-carboxamido)bicyclo[1.1.1]pentan-1-yl)propanoic acid;
3-(3-methyl-3-(1-(4-(trifluoromethyl)benzyl)-1H-indole-7-carboxamido)cyclobutyl)propanoic acid;
cis-3-(3-methyl-3-(1-(4-(trifluoromethyl)benzyl)-1H-indole-7-carboxamido)cyclobutyl)propanoic acid;
N-(3-(2-oxo-2-(phenylsulfonamido)ethyl)bicyclo[1.1.1]pentan-1-yl)-1-(4-(trifluoromethyl)benzyl)-1H-indole-7-carboxamide;
N-(3-((3-(phenylsulfonyl)ureido)methyl)bicyclo[1.1.1]pentan-1-yl)-1-(4-(trifluoromethyl)benzyl)-1H-indole-7-carboxamide;
N-(3-((1H-tetrazol-5-yl)methyl)bicyclo[1.1.1]pentan-1-yl)-1-(4-(trifluoromethyl)benzyl)-1H-indole-7-carboxamide;
2-(4-(1-(4-(trifluoromethyl)benzyl)-1H-indole-7-carboxamido)bicyclo[2.1.1]hexan-1-yl)acetic acid;
6-(4-fluoro-1-(4-(trifluoromethyl)benzyl)-1H-indole-7-carboxamido)spiro[3.3]heptane-2-carboxylic acid;
(R)-6-(4-fluoro-1-(4-(trifluoromethyl)benzyl)-1H-indole-7-carboxamido)spiro[3.3]heptane-2-carboxylic acid;
(S)-6-(4-fluoro-1-(4-(trifluoromethyl)benzyl)-1H-indole-7-carboxamido)spiro[3.3]heptane-2-carboxylic acid;
6-(5-fluoro-1-(4-(trifluoromethyl)benzyl)-1H-indole-7-carboxamido)spiro[3.3]heptane-2-carboxylic acid;
(R)-6-(5-fluoro-1-(4-(trifluoromethyl)benzyl)-1H-indole-7-carboxamido)spiro[3.3]heptane-2-carboxylic acid;
(S)-6-(5-fluoro-1-(4-(trifluoromethyl)benzyl)-1H-indole-7-carboxamido)spiro[3.3]heptane-2-carboxylic acid;

6-(5-chloro-1-(4-(trifluoromethyl)benzyl)-1H-indole-7-carboxamido)spiro[3.3]heptane-2-carboxylic acid;
(R)-6-(5-chloro-1-(4-(trifluoromethyl)benzyl)-1H-indole-7-carboxamido)spiro[3.3]heptane-2-carboxylic acid;
(S)-6-(5-chloro-1-(4-(trifluoromethyl)benzyl)-1H-indole-7-carboxamido)spiro[3.3]heptane-2-carboxylic acid;
6-(6-fluoro-1-(4-(trifluoromethyl)benzyl)-1H-indole-7-carboxamido)spiro[3.3]heptane-2-carboxylic acid;
(R)-6-(6-fluoro-1-(4-(trifluoromethyl)benzyl)-1H-indole-7-carboxamido)spiro[3.3]heptane-2-carboxylic acid;
(S)-6-(6-fluoro-1-(4-(trifluoromethyl)benzyl)-1H-indole-7-carboxamido)spiro[3.3]heptane-2-carboxylic acid;
6-(1-(4-cyanobenzyl)-1H-indole-7-carboxamido)spiro[3.3]heptane-2-carboxylic acid;
(R)-6-(1-(4-cyanobenzyl)-1H-indole-7-carboxamido)spiro[3.3]heptane-2-carboxylic acid;
(S)-6-(1-(4-cyanobenzyl)-1H-indole-7-carboxamido)spiro[3.3]heptane-2-carboxylic acid;
6-(1-(4-(difluoromethyl)benzyl)-1H-indole-7-carboxamido)spiro[3.3]heptane-2-carboxylic acid;
(R)-6-(1-(4-(difluoromethyl)benzyl)-1H-indole-7-carboxamido)spiro[3.3]heptane-2-carboxylic acid;
(S)-6-(1-(4-(difluoromethyl)benzyl)-1H-indole-7-carboxamido)spiro[3.3]heptane-2-carboxylic acid;
2-(4-(1-(4-(difluoromethyl)benzyl)-1H-indole-7-carboxamido)bicyclo[2.1.1]hexan-1-yl)acetic acid;
2-(3-(4-fluoro-1-(4-(trifluoromethyl)benzyl)-1H-indole-7-carboxamido)bicyclo[1.1.1]pentan-1-yl)acetic acid;
2-(4-(4-fluoro-1-(4-(trifluoromethyl)benzyl)-1H-indole-7-carboxamido)bicyclo[2.1.1]hexan-1-yl)acetic acid;
2-(4-(1-((4-(pentafluorothiol)phenyl)methyl)-1H-indole-7-carboxamido)bicyclo[2.1.1]hexan-1-yl)acetic acid;
6-(1-((4-(pentafluorothiol)phenyl)methyl)-1H-indole-7-carboxamido)spiro[3.3]heptane-2-carboxylic acid;
(R)-6-(1-((4-(pentafluorothiol)phenyl)methyl)-1H-indole-7-carboxamido)spiro[3.3]heptane-2-carboxylic acid;
(S)-6-(1-((4-(pentafluorothiol)phenyl)methyl)-1H-indole-7-carboxamido)spiro[3.3]heptane-2-carboxylic acid;
6-(1-(4-(difluoromethyl)benzyl)-4-fluoro-1H-indole-7-carboxamido)spiro[3.3]heptane-2-carboxylic acid;
(R)-6-(1-(4-(difluoromethyl)benzyl)-4-fluoro-1H-indole-7-carboxamido)spiro[3.3]heptane-2-carboxylic acid;
(S)-6-(1-(4-(difluoromethyl)benzyl)-4-fluoro-1H-indole-7-carboxamido)spiro[3.3]heptane-2-carboxylic acid;
2-(3-(1-(4-(difluoromethyl)benzyl)-4-fluoro-1H-indole-7-carboxamido)bicyclo[1.1.1]pentan-1-yl)acetic acid;
2-(3-(5-fluoro-1-(4-(trifluoromethyl)benzyl)-1H-indole-7-carboxamido)bicyclo[1.1.1]pentan-1-yl)acetic acid;
2-(3-(1-([1,1'-biphenyl]-4-ylmethyl)-1H-indole-7-carboxamido)bicyclo[1.1.1] pentan-1-yl)acetic acid;
2-(3-(1-([1,1'-biphenyl]-4-ylmethyl)-4-fluoro-1H-indole-7-carboxamido)bicyclo[1.1.1]pentan-1-yl)acetic acid;
2-(3-(1-([1,1'-biphenyl]-4-ylmethyl)-1H-indazole-7-carboxamido)bicyclo[1.1.1] pentan-1-yl)acetic acid;
2-(3-(1-(4-(trifluoromethoxy)benzyl)-1H-indazole-7-carboxamido)bicyclo[1.1.1] pentan-1-yl)acetic acid;
2-(3-(4-fluoro-1-(4-iodobenzyl)-1H-indole-7-carboxamido)bicyclo[1.1.1]pentan-1-yl) acetic acid;
2-(3-(4-fluoro-1-(4-(pyridine-4-yl)benzyl)-1H-indole-7-carboxamido)bicyclo[1.1.1]pentan-1-yl) acetic acid; and
2-(3-(4-fluoro-1-(4-morpholinobenzyl)-1H-indole-7-carboxamido)bicyclo[1.1.1]pentan-1-yl) acetic acid;
or a pharmaceutically acceptable salt, solvate, solvate of the salt, hydrate, a single stereoisomer, a mixture of stereoisomers, a racemic mixture of stereoisomers, or prodrug thereof.

Some embodiments provided herein describe pharmaceutical compositions comprising a compound of any of Formula I, Ia, Ib, Ic, or Id, or a pharmaceutically acceptable salt, solvate, solvate of the salt, hydrate, a single stereoisomer, a mixture of stereoisomers, a racemic mixture of stereoisomers, or prodrug thereof of any of the foregoing, and a pharmaceutically acceptable carrier.

Some embodiments provided herein describe methods for the treatment of cancer comprising administering to a patient in need thereof a compound of any of Formula I, Ia, Ib, Ic, or Id, or a pharmaceutically acceptable salt, solvate, solvate of the salt, hydrate, a single stereoisomer, a mixture of stereoisomers, a racemic mixture of stereoisomers, or prodrug thereof of any of the foregoing, or a pharmaceutical composition comprising any of Formula I, Ia, Ib, Ic, or Id, or a pharmaceutically acceptable salt of any of the foregoing.

In some embodiments, the cancer is selected from the group consisting of glioblastoma, bone cancer, head and neck cancer, melanoma, basal cell carcinoma, squamous cell carcinoma, adenocarcinoma, oral cancer, esophageal cancer, gastric cancer, intestinal cancer, colon cancer, bladder cancer, hepatocellular carcinoma, renal cell carcinoma, pancreatic cancer, ovarian cancer, cervical cancer, lung cancer, breast cancer, and prostate cancer.

In some embodiments, the treatment further comprises an additional agent selected from an anti-PD-1 antibody and an anti-PD-L1 antibody.

DETAILED DESCRIPTION OF THE INVENTION

Figure 1A:
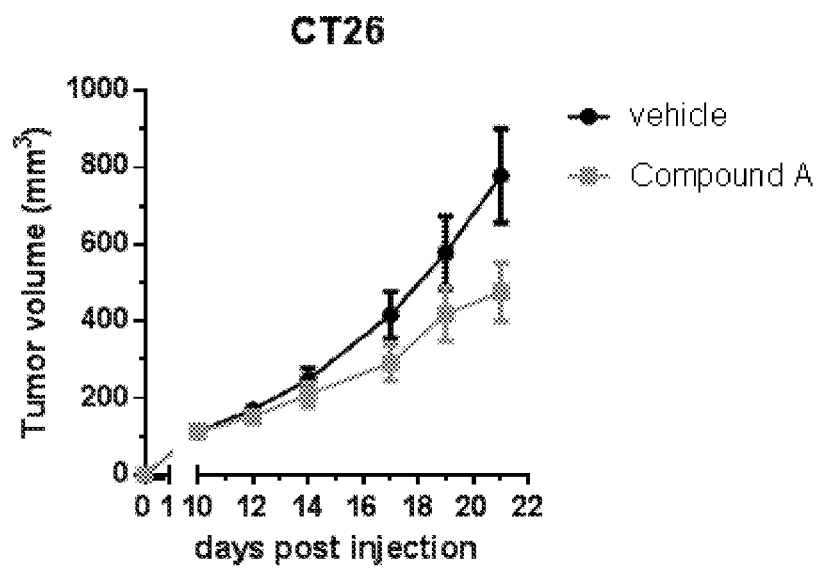
FIGS. 1A and 1B illustrate the effect of Compound A on tumor volume in a murine colon cancer model.

Provided herein in some embodiments are selective EP4 receptor antagonists and compositions comprising these compounds (i.e., the selective EP4 receptor antagonists). The compounds and compositions are useful for the treatment of cancer.

Some embodiments provided herein describe compounds of Formula I:

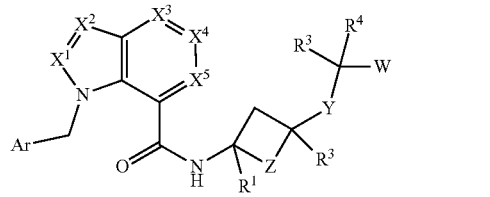

or a pharmaceutically acceptable salt, solvate, solvate of the salt, or prodrug thereof.

In certain embodiments, provided herein are compounds of Formula I:

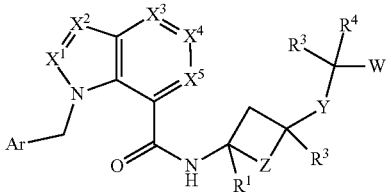

or a pharmaceutically acceptable salt, solvate, solvate of the salt, or prodrug thereof, wherein:

Ar is an aryl or a heteroaryl, wherein said aryl and said heteroaryl are each optionally substituted with 1 to 3 substituents independently selected from the group consisting of:
(a) $C_1$-$C_6$ alkyl,
(b) $C_3$-$C_7$ cycloalkyl,
(c) heterocycle,
(d) aryl,
(e) heteroaryl,
(f) halogen,
(g) CN,
(h) $OR^b$,
(i) $N(R^b)C(=O)R^c$,
(j) $C(=O)N(R^b)(R^c)$,
(k) $S(=O)_m R^b$,
(l) $S(=O)_2 N(R^b)(R^c)$,
(m) $N(R^b)S(=O)_2 R^c$,
(n) $SF_5$; and
(o) $C_1$-$C_6$ haloalkyl.

W is selected from the group consisting of:
(a) $CO_2H$,
(b) $C(=O)NHOH$,
(c) $S(=O)_2 NHR^b$,
(d) $S(=O)_2 NHC(=O)R^b$,
(e) $NHC(=O)NHSO_2 R^b$,
(f) 1H-tetrazole,
(g) 1,2,4-oxadiazol-5(4H)one,
(h) 1,2,4-thiadiazol-5(4H)one,
(i) 1,2,4-oxadiazole-5(4H)-thione,
(j) 1,2,4-triazole-5(4H)-one,
(k) tetrazol-5(4H)-one, and
(l) $C(=O)NHS(=O)_2 R^b$;

$X^1$, $X^2$, $X^3$, $X^4$, and $X^5$ are each independently N or $CR^a$, wherein not more than 2 of $X^1$, $X^2$, $X^3$, $X^4$, and $X^5$ are N;

Y is selected from:
(a) a bond,
(b) $(CH_2)_n$ wherein 1 to 4 hydrogen atoms may be replaced by $R^{a'}$,
(c) O, and
(d) $NR^b$;

Z is $(CH_2)_n$, wherein 1 to 4 hydrogen atoms may be replaced by $R^{a'}$;

$R^1$ and $R^2$ are independently selected from:
(a) H,
(b) $C_1$-$C_6$ alkyl,
(c) $C_3$-$C_6$ cycloalkyl, and
(d) $C_1$-$C_6$ haloalkyl;
wherein $R^1$ and $R^2$ are not both H; or $R^1$ and $R^2$ taken together represent $-(CH_2)_n-$, $-(CH_2)_n O(CH_2)_p-$, $-(CH_2)_n NR^b(CH_2)_p-$ or $-(CH_2)_n S(=O)_m (CH_2)_p-$;

$R^3$ and $R^4$ are independently selected from the group consisting of:
(a) H,
(b) $C_1$-$C_6$ alkyl,
(c) $C_3$-$C_6$ cycloalkyl,
(d) aryl,
(e) heteroaryl,
(f) halogen,
(g) $C_1$-$C_6$ haloalkyl; or $R^3$ and $R^4$ taken together represent $-(CH_2)_n-$, $-(CH_2)_n O(CH_2)_p-$, $-(CH_2)_n NR^b(CH_2)_p-$ or $-(CH_2)_n S(=O)_m (CH_2)_p-$; or $R^3$ and $R^2$ taken together represent $(CH_2)_n$, $(CH_2)_n O(CH_2)_p$, $(CH_2)_n NR^b(CH_2)_p$, or $(CH_2)_n S(=O)_m (CH_2)_p$;

$R^a$ is selected from the group consisting of:
(a) H,
(b) $C_1$-$C_6$ alkyl,
(c) halogen,
(d) aryl,
(e) $OR^b$,
(f) cyano,
(g) heteroaryl,
(h) $C_3$-$C_6$ cycloalkyl,
(i) $C_1$-$C_6$ haloalkyl;

$R^{a'}$ is selected from the group consisting of:
(a) cyano,
(b) $C_1$-$C_6$ alkyl,
(c) halogen,
(d) aryl,
(e) $OR^b$,
(f) heteroaryl,
(g) $C_3$-$C_6$ cycloalkyl, and
(h) $C_1$-$C_6$ haloalkyl;

$R^b$ and $R^c$ are independently selected from the group consisting of
(a) H,
(b) $C_1$-$C_6$ alkyl,
(c) aryl,
(d) heteroaryl,
(e) $C_3$-$C_6$ cycloalkyl,
(f) $C_2$-$C_6$ heterocycle and
(g) $C_1$-$C_6$ haloalkyl; or $R^b$ and $R^c$ taken together with the N to which they are both attached form a 3- to 6-membered heterocycle optionally having an additional heteroatom selected from N, O and S;

m is 0, 1, or 2;
n is 1, 2 or 3; and
p is 1, 2 or 3.

In certain embodiments, provided herein are compounds of Formula I:

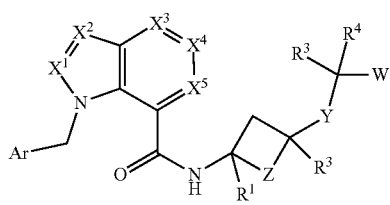

or a pharmaceutically acceptable salt, solvate, solvate of the salt, or prodrug thereof, wherein:

Ar is an aryl or a heteroaryl, wherein said aryl and said heteroaryl are each optionally substituted with 1 to 3 substituents independently selected from the group consisting of:
- (a) $C_1$-$C_6$ alkyl,
- (b) $C_3$-$C_7$ cycloalkyl,
- (c) heterocycle,
- (d) aryl,
- (e) heteroaryl,
- (f) halogen,
- (g) CN,
- (h) $OR^b$,
- (i) $N(R^b)C(=O)R^c$,
- (j) $C(=O)N(R^b)(R^c)$,
- (k) $S(=O)_m R^b$,
- (l) $S(=O)_2 N(R^b)(R^c)$,
- (m) $N(R^b)S(=O)_2 R^c$,
- (n) $SF_5$; and
- (o) $C_1$-$C_6$ haloalkyl.

W is selected from the group consisting of:
- (a) $CO_2 H$,
- (b) $C(=O)NHOH$,
- (c) $S(=O)_2 NHR^b$,
- (d) $S(=O)_2 NHC(=O)R^b$,
- (e) $NHC(=O)NHSO_2 R^b$,
- (f) 1H-tetrazole,
- (g) 1,2,4-oxadiazol-5(4H)one,
- (h) 1,2,4-thiadiazol-5(4H)one,
- (i) 1,2,4-oxadiazole-5(4H)-thione,
- (j) 1,2,4-triazole-5(4H)-one,
- (k) tetrazol-5(4H)-one, and
- (l) $C(=O)NHS(=O)_2 R^b$;

$X^1$, $X^2$, $X^3$, $X^4$, and $X^5$ are each independently N or $CR^a$, wherein not more than 2 of $X^1$, $X^2$, $X^3$, $X^4$, and $X^5$ are N;

Y is selected from:
- (a) a bond,
- (b) $(CH_2)_n$ wherein 1 to 4 hydrogen atoms may be replaced by $R^{a'}$,
- (c) O, and
- (d) $NR^b$;

Z is $(CH_2)_n$, wherein 1 to 4 hydrogen atoms may be replaced by $R^{a'}$;

$R^1$ and $R^2$ are independently selected from:
- (a) H,
- (b) $C_1$-$C_6$ alkyl,
- (c) $C_3$-$C_6$ cycloalkyl, and
- (d) $C_1$-$C_6$ haloalkyl;

wherein $R^1$ and $R^2$ are not both H; or $R^1$ and $R^2$ taken together represent $-(CH_2)_n-$, $-(CH_2)_n O(CH_2)_p-$, $-(CH_2)_n NR^b(CH_2)_p-$ or $-(CH_2)_n S(=O)_m (CH_2)_p-$;

$R^3$ and $R^4$ are independently selected from the group consisting of:
- (a) H,
- (b) $C_1$-$C_6$ alkyl,
- (c) $C_3$-$C_6$ cycloalkyl,
- (d) aryl,
- (e) heteroaryl,
- (f) halogen,
- (g) $C_1$-$C_6$ haloalkyl; or $R^3$ and $R^4$ taken together represent $-(CH_2)_n-$, $-(CH_2)_n O(CH_2)_p-$, $-(CH_2)_n NR^b(CH_2)_p-$ or $-(CH_2)_n S(=O)_m (CH_2)_p-$; or $R^3$ and $R^2$ taken together represent $(CH_2)_n$, $(CH_2)_n O(CH_2)_p$, $(CH_2)_n NR^b(CH_2)_p$, or $(CH_2)_n S(=O)_m (CH_2)_p$;

$R^a$ is selected from the group consisting of:
- (a) H,
- (b) $C_1$-$C_6$ alkyl,
- (c) halogen,
- (d) aryl,
- (e) $OR^b$,
- (f) cyano,
- (g) heteroaryl,
- (h) $C_3$-$C_6$ cycloalkyl,
- (i) $C_1$-$C_6$ haloalkyl;

$R^{a'}$ is selected from the group consisting of:
- (a) cyano,
- (b) $C_1$-$C_6$ alkyl,
- (c) halogen,
- (d) aryl,
- (e) $OR^b$,
- (f) heteroaryl,
- (g) $C_3$-$C_6$ cycloalkyl, and
- (h) $C_1$-$C_6$ haloalkyl;

$R^b$ and $R^c$ are independently selected from the group consisting of
- (a) H,
- (b) $C_1$-$C_6$ alkyl,
- (c) aryl,
- (d) heteroaryl,
- (e) $C_3$-$C_6$ cycloalkyl, and
- (f) $C_1$-$C_6$ haloalkyl; or $R^b$ and $R^c$ taken together with the N to which they are both attached form a 3- to 6-membered heterocycle optionally having an additional heteroatom selected from N, O and S;

m is 0, 1, or 2;
n is 1, 2 or 3; and
p is 1, 2 or 3.

In some embodiments, Ar is an aryl or a heteroaryl, wherein said aryl and said heteroaryl are each optionally substituted with 1 to 3 substituents independently selected from the group consisting of:
- (a) $C_1$-$C_6$ alkyl,
- (b) $C_3$-$C_7$ cycloalkyl,
- (c) heterocycle,
- (d) aryl,
- (e) heteroaryl,
- (f) halogen,
- (g) CN,
- (h) $OR^b$,
- (i) $N(R^b)C(=O)R^c$,
- (j) $C(=O)N(R^b)(R^c)$,
- (k) $S(=O)_m R^b$,
- (l) $S(=O)_2 N(R^b)(R^c)$,
- (m) $N(R^b)S(=O)_2 R^c$,
- (n) $SF_5$, and
- (o) $C_1$-$C_6$ haloalkyl.

In some embodiments, Ar is a mono-substituted phenyl group. In some embodiments, Ar is a di-substituted phenyl group. In some embodiments, Ar is a tri-substituted phenyl group. In some embodiments, Ar is a mono-substituted pyridyl group. In some embodiments, Ar is a mono-substituted pyrimidinyl group. In some embodiments, Ar is a di-substituted pyridyl group. In some embodiments, Ar is a di-substituted pyrimidinyl group. In some embodiments, the mono-substituted group is substituted with CN (cyano), halogen, $CF_3$, $CF_2 H$, $SF_5$, or an unsubstituted $C_1$-$C_6$ alkyl. In some embodiments, the mono-substituted group is substituted with CN (cyano), halogen, haloalkyl, aryl, heteroaryl, haloalkoxy, heterocycle, or alkyl. In some embodiments, the mono-substituted group is substituted with CN (cyano), halogen, haloalkyl, phenyl, pyridyl, haloalkoxy, or heterocycle. In some embodiments, Ar is a phenyl substituted with one to three substituents selected from aryl, heteroaryl, cycloalkyl, heterocycle, CN (cyano), halogen, haloalkyl, $SF_5$, —$OR^b$, and alkyl; and each $R^b$ is independently H, $C_1$-$C_6$ alkyl, $C_3$-$C_6$ cycloalkyl, heterocyclyl, or $C_1$-$C_6$ haloalkyl.

In some embodiments, W is selected from the group consisting of:
(a) $CO_2H$,
(b) C(=O)NHOH,
(c) S(=O)$_2$$NHR^b$,
(d) S(=O)$_2$NHC(=O)$R^b$,
(e) NHC(=O)$NHSO_2R^b$,
(f) 1H-tetrazole,
(g) 1,2,4-oxadiazol-5(4H)one,
(h) 1,2,4-thiadiazol-5(4H)one,
(i) 1,2,4-oxadiazole-5(4H)-thione,
(j) 1,2,4-triazole-5(4H)-one,
(k) tetrazol-5(4H)-one, and
(l) C(=O)NHS(=O)$_2R^b$.

In some embodiments, $X^1$, $X^2$, $X^3$, $X^4$, and $X^5$ are each independently N or $CR^a$, with the proviso that not more than 2 of $X^1$, $X^2$, $X^3$, $X^4$, and $X^5$ are N.

In some embodiments, Y is selected from:
(a) a bond,
(b) $(CH_2)_n$ wherein 1 to 4 hydrogen atoms may be replaced by $R^{a'}$,
(c) O, and
(d) $NR^b$.

In some embodiments, Z is $(CH_2)_n$, wherein 1 to 4 hydrogen atoms may be replaced by $R^{a'}$ In some embodiments, $R^1$ and $R^2$ are independently selected from:
(a) H,
(b) $C_1$-$C_6$ alkyl,
(c) $C_3$-$C_6$ cycloalkyl, and
(d) $C_1$-$C_6$ haloalkyl.

In some embodiments, $R^1$ and $R^2$ are not both H.

In some embodiments, $R^1$ and $R^2$ taken together represent —$(CH_2)_n$—, —$(CH_2)_nO(CH_2)_p$—, —$(CH_2)_nNR^b(CH_2)_p$— or —$(CH_2)_nS(=O)_m(CH_2)_p$—.

In some embodiments, $R^3$ and $R^4$ are independently selected from the group consisting of:
(a) H,
(b) $C_1$-$C_6$ alkyl,
(c) $C_3$-$C_6$ cycloalkyl,
(d) aryl,
(e) heteroaryl,
(f) halogen, and
(g) $C_1$-$C_6$ haloalkyl.

In some embodiments, $R^3$ and $R^4$ taken together represent —$(CH_2)_n$—, —$(CH_2)_nO(CH_2)_p$—, —$(CH_2)_nNR^b(CH_2)_p$— or —$(CH_2)_nS(=O)_m(CH_2)_p$—.

In some embodiments, $R^3$ and $R^2$ taken together represent $(CH_2)_n$, $(CH_2)_nO(CH_2)_p$, $(CH_2)_nNR^b(CH_2)_p$, or $(CH_2)_nS(=O)_m(CH_2)_p$.

In some embodiments, $R^a$ is selected from the group consisting of:
(a) H,
(b) $C_1$-$C_6$ alkyl,
(c) halogen,
(d) aryl,
(e) $OR^b$,
(f) cyano,
(g) heteroaryl,
(h) $C_3$-$C_6$ cycloalkyl, and
(i) $C_1$-$C_6$ haloalkyl.

In some embodiments, $R^{a'}$ is selected from the group consisting of:
(a) cyano,
(b) $C_1$-$C_6$ alkyl,
(c) halogen,
(d) aryl,
(e) $OR^b$,
(f) heteroaryl,
(g) $C_3$-$C_6$ cycloalkyl, and
(h) $C_1$-$C_6$ haloalkyl.

In some embodiments, $R^b$ and $R^c$ are independently selected from the group consisting of:
(a) H,
(b) $C_1$-$C_6$ alkyl,
(c) aryl,
(d) heteroaryl,
(e) $C_3$-$C_6$ cycloalkyl, and
(f) $C_1$-$C_6$ haloalkyl.

In some embodiments, $R^b$ and $R^c$ taken together with the N to which they are both attached form a 3- to 6-membered heterocycle optionally having an additional heteroatom selected from N, O and S.

In some embodiments, m is 0, 1, or 2.
In some embodiments, n is 1, 2 or 3.
In some embodiments, p is 1, 2 or 3.

In some embodiments, Ar is phenyl optionally substituted with 1 to 3 substituents independently selected from:
(a) halogen,
(b) cyano,
(c) $C_1$-$C_6$ alkyl,
(d) $SF_5$,
(e) $C_1$-$C_6$ haloalkyl
(f) $OR^b$ wherein $R^b$ is $C_1$-$C_6$ alkyl, aryl, heteroaryl, $C_3$-$C_6$ cycloalkyl or $C_1$-$C_6$ haloalkyl;
(g) heterocycle,
(h) aryl, and
(i) heteroaryl.

In some embodiments, Ar is phenyl optionally substituted with 1 to 3 substituents independently selected from:
(a) halogen,
(b) cyano,
(c) $C_1$-$C_6$ alkyl,
(d) $SF_5$, and
(e) $C_1$-$C_6$ haloalkyl.

In some embodiments, each of $X^1$, $X^2$, $X^3$, $X^4$ and $X^5$ is independently C—$R^a$, or one of $X^1$, $X^2$, $X^3$, $X^4$ and $X^5$ is N, and the others are each independently C—$R^a$.

In some embodiments, each of $X^1$, $X^2$, $X^3$, $X^4$ and $X^5$ is independently C—$R^a$.

In some embodiments, $R^a$ is H or a halogen atom.

In some embodiments, W is selected from the group consisting of:
(a) $CO_2H$ and
(b) 1H-tetrazole.

In some embodiments, Z is —$CH_2$—.
In some embodiments, Y is a bond or —$CH_2$—.
In some embodiments, $R^1$ and $R^2$ taken together represent —$CH_2$—, —$CH_2CH_2$— or —$CH_2CH_2CH_2$—. In some embodiments, $R^1$ and $R^2$ taken together represent —$CH_2$— or —$CH_2CH_2$—.

In some embodiments, Y is a direct bond or —$CH_2$—, and $R^3$ and $R^2$ taken together represent —$CH_2$—, —$CH_2CH_2$— or —$CH_2CH_2CH_2$—.

In some embodiments, Y is —$CH_2$—, and $R^3$ and $R^2$ taken together represent —$CH_2$—, —$CH_2CH_2$— or —$CH_2CH_2CH_2$—.

In some embodiments, Y is —CH$_2$—, and R$^3$ and R$^2$ taken together represent —CH$_2$— or —CH$_2$CH$_2$—.

Some embodiments provide compounds having the Formula Ia:

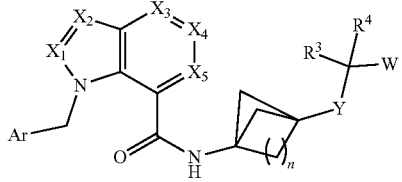

Ia or a pharmaceutically acceptable salt, solvate, solvate of the salt, or prodrug thereof.

In some embodiments, Ar is aryl or heteroaryl optionally substituted with 1 to 3 substituents independently selected from:
(a) halogen,
(b) cyano,
(c) C$_1$-C$_6$ alkyl,
(d) SF$_5$,
(e) C$_1$-C$_6$ haloalkyl,
(f) OR$^b$ wherein R$^b$ is C$_1$-C$_6$ alkyl, aryl, heteroaryl, C$_3$-C$_6$ cycloalkyl or C$_1$-C$_6$ haloalkyl,
(g) heterocycle,
(h) aryl, and
(i) heteroaryl.

In some embodiments, Ar is phenyl optionally substituted with 1 to 3 substituents independently selected from:
(a) halogen,
(b) cyano,
(c) C$_1$-C$_6$ alkyl,
(d) SF$_5$,
(e) C$_1$-C$_6$ haloalkyl,
(f) OR$^b$ wherein R$^b$ is C$_1$-C$_6$ alkyl, aryl, heteroaryl, C$_3$-C$_6$ cycloalkyl or C$_1$-C$_6$ haloalkyl;
(g) heterocycle,
(h) aryl, and
(i) heteroaryl.

In some embodiments, Ar is phenyl optionally substituted with 1 to 3 substituents independently selected from:
(a) halogen,
(b) cyano,
(c) C$_1$-C$_6$ alkyl,
(d) SF$_5$, and
(e) C$_1$-C$_6$ haloalkyl.

In some embodiments, each X$^1$, X$^2$, X$^3$, X$^4$ and X$^5$ is independently C—R$^a$, or one of X$^1$, X$^2$, X$^3$, X$^4$ and X$^5$ is N, and the others are each independently C—R$^a$.

In some embodiments, W is selected from the group consisting of: (a) CO$_2$H and (b) 1H-tetrazole.

In some embodiments, Y is a bond or —CH$_2$—.

In some embodiments, n is 1 or 2.

In some embodiments, R$^3$ and R$^4$ are independently selected from the group consisting of: (a) H, (b) C$_1$-C$_3$ alkyl, (c) C$_1$-C$_3$ haloalkyl.

In some embodiments, R$^a$ is selected from the group consisting of: (a) H and (b) halogen.

In some embodiments, Y is a bond, and n is 1.

Some embodiments provide compounds having the Formula Ib:

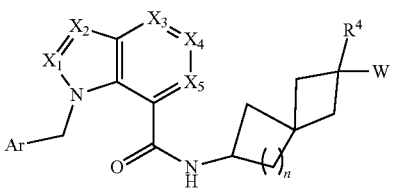

Ib or a pharmaceutically acceptable salt, solvate, solvate of the salt, or prodrug thereof.

In some embodiments, Ar is aryl or heteroaryl optionally substituted with 1 to 3 substituents independently selected from:
(a) halogen,
(b) cyano,
(c) C$_1$-C$_6$ alkyl;
(d) SF$_5$,
(e) C$_1$-C$_6$ haloalkyl,
(f) OR$^b$ wherein R$^b$ is C$_1$-C$_6$ alkyl, aryl, heteroaryl, C$_3$-C$_6$ cycloalkyl or C$_1$-C$_6$ haloalkyl,
(g) heterocycle,
(h) aryl, and
(i) heteroaryl.

In some embodiments, Ar is phenyl optionally substituted with 1 to 3 substituents independently selected from:
(a) halogen,
(b) cyano,
(c) C$_1$-C$_6$ alkyl,
(d) SF$_5$,
(e) C$_1$-C$_6$ haloalkyl,
(f) OR$^b$ wherein R$^b$ is C$_1$-C$_6$ alkyl, aryl, heteroaryl, C$_3$-C$_6$ cycloalkyl or C$_1$-C$_6$ haloalkyl,
(g) heterocycle,
(h) aryl, and
(i) heteroaryl.

In some embodiments, Ar is phenyl optionally substituted with 1 to 3 substituents independently selected from:
(a) halogen,
(b) cyano,
(c) C$_1$-C$_6$ alkyl,
(d) SF$_5$, and
(e) C$_1$-C$_6$ haloalkyl.

In some embodiments, each X$^1$, X$^2$, X$^3$, X$^4$ and X$^5$ is independently C—R$^a$, or one of X$^1$, X$^2$, X$^3$, X$^4$ and X$^5$ is N, and the others are each independently C—R$^a$.

In some embodiments, W is selected from the group consisting of: (a) CO$_2$H and (b) 1H-tetrazole.

In some embodiments, n is 1 or 2.

In some embodiments, R$^4$ is selected from the group consisting of: (a) H, (b) C$_1$-C$_3$ alkyl, and (c) C$_1$-C$_3$ haloalkyl.

In some embodiments, n is 1 and R$^a$ is selected from the group consisting of: (a) H and (b) halogen.

Some embodiments provided herein describe compounds of Formula I having the structure of Formula Ic or Id:

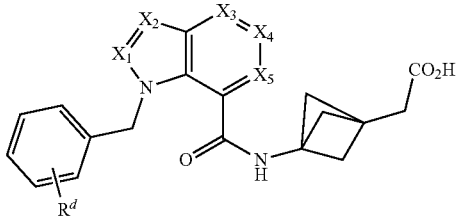

Ic

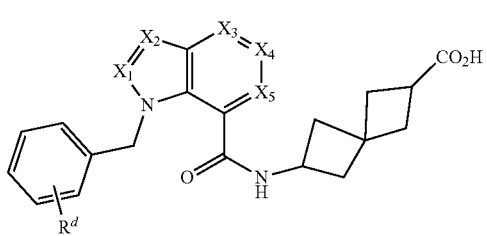

Id or a pharmaceutically acceptable salt, solvate, solvate of the salt, or prodrug thereof.

In some embodiments, each $X^1$, $X^2$, $X^3$, $X^4$ and $X^5$ is independently C—$R^a$, or one of $X^1$, $X^2$, $X^3$, $X^4$ and $X^5$ is N, and the others are each independently C—$R^a$.

In some embodiments, $R^a$ is selected from the group consisting of: (a) H and (b) halogen.

In some embodiments, $R^d$ is selected from the group consisting of:
(a) CN,
(b) $C_1$-$C_3$ alkyl,
(c) $SF_5$, and
(d) $C_1$-$C_3$ haloalkyl,
(e) $OR^b$ wherein $R^b$ is $C_1$-$C_6$ alkyl, aryl, heteroaryl, $C_3$-$C_6$ cycloalkyl or $C_1$-$C_6$ haloalkyl,
(f) heterocycle,
(g) aryl, and
(h) heteroaryl.

In some embodiments, $R^d$ is selected from the group consisting of:
(a) CN,
(b) $C_1$-$C_3$ alkyl,
(c) $SF_5$, and
(d) $C_1$-$C_3$ haloalkyl.

In some embodiments, each $X^1$, $X^2$, $X^3$, $X^4$ and $X^5$ is CH; or one of $X^1$, $X^2$, $X^3$, $X^4$ and $X^5$ is C—$R^a$ and the others are CH, and $R^a$ is halogen.

In some embodiments, $R^1$ and $R^2$, taken together, represent $CH_2$, Ar is a mono-substituted aryl group, and Y is a bond. In some embodiments, each $X^1$, $X^2$, $X^3$, $X^4$ and $X^5$ is CH, $R^1$ and $R^2$, taken together, represent $CH_2$, Ar is a mono-substituted aryl group, and Y is a bond. In some embodiments, one of $X^1$, $X^2$, $X^3$, $X^4$ and $X^5$ is C—$R^a$ and the others are CH, $R^a$ is halogen, $R^1$ and $R^2$, taken together, represent $CH_2$, Ar is a mono-substituted aryl group, and Y is a bond. In some embodiments, one of $X^1$, $X^2$, $X^3$, $X^4$ and $X^5$ is N and the others are CH, $R^1$ and $R^2$, taken together, represent $CH_2$, Ar is a mono-substituted aryl group, and Y is a bond. In some embodiments, two of $X^1$, $X^2$, $X^3$, $X^4$ and $X^5$ is N and the others are CH, $R^1$ and $R^2$, taken together, represent $CH_2$, Ar is a mono-substituted aryl group, and Y is a bond.

In certain embodiments, the mono-substituted aryl group is substituted with phenyl, pyridyl, heterocycle, CN (cyano), halogen, $C_1$-$C_6$ haloalkyl, $SF_5$, or haloalkoxy.

In certain embodiments, provided herein are compounds of Formula I:

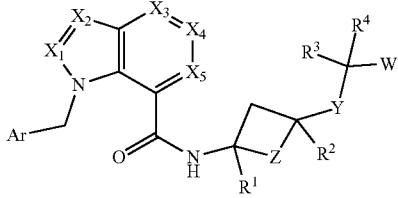

I or a pharmaceutically acceptable salt, solvate, solvate of the salt, hydrate, a single stereoisomer, a mixture of stereoisomers, a racemic mixture of stereoisomers, or prodrug thereof, wherein:

Ar is an aryl or a heteroaryl, wherein said aryl and said heteroaryl are each optionally substituted with 1 to 3 substituents independently selected from:
(a) $C_1$-$C_6$ alkyl,
(b) $C_3$-$C_7$ cycloalkyl,
(c) heterocycle,
(d) aryl,
(e) heteroaryl,
(f) halogen,
(g) CN,
(h) $OR^b$,
(i) $N(R^b)C(=O)R^c$,
(j) $C(=O)N(R^b)(R^c)$,
(k) $S(=O)_mR^b$,
(l) $S(=O)_2N(R^b)(R^c)$,
(m) $N(R^b)S(=O)_2R^c$,
(n) $SF_5$; and
(o) $C_1$-$C_6$ haloalkyl W is selected from:
(a) $C(=O)OR^5$,
(b) $C(=O)NHOH$,
(c) $S(=O)_2NHR^b$,
(d) $S(=O)_2NHC(=O)R^b$,
(e) $NHC(=O)NHSO_2R^b$,
(f) 1H-tetrazole,
(g) 1,2,4-oxadiazol-5(4H)one,
(h) 1,2,4-thiadiazol-5(4H)one,
(i) 1,2,4-oxadiazole-5(4H)-thione,
(j) 1,2,4-triazole-5(4H)-one,
(k) tetrazol-5(4H)-one, and
(l) $C(=O)NHS(=O)_2R^b$;

$X^1$, $X^2$, $X^3$, $X^4$, and $X^5$ are each independently N or $CR^a$, wherein not more than 2 of $X^1$, $X^2$, $X^3$, $X^4$, and $X^5$ are N;

Y is selected from:
(a) a bond,
(b) $(CH_2)_n$ wherein 1 to 4 hydrogen atoms may be replaced by $R^{a'}$,
(c) O, and
(d) $NR^b$;

Z is $(CH_2)_n$, wherein 1 to 4 hydrogen atoms may be replaced by $R^{a'}$;

$R^1$ and $R^2$ are independently selected from:
(a) H,
(b) $C_1$-$C_6$ alkyl,
(c) $C_3$-$C_6$ cycloalkyl, and
(d) $C_1$-$C_6$ haloalkyl;
wherein $R^2$ is not H; or
$R^1$ and $R^2$ taken together represent —$(CH_2)_n$—, —$(CH_2)_nO(CH_2)_p$—, —$(CH_2)_nNR^b(CH_2)_p$— or —$(CH_2)_nS(=O)_m(CH_2)_p$—;

$R^3$ and $R^4$ are independently selected from:
(a) H,
(b) $C_1$-$C_6$ alkyl,
(c) $C_3$-$C_6$ cycloalkyl,
(d) aryl,
(e) heteroaryl,
(f) halogen, and
(g) $C_1$-$C_6$ haloalkyl; or
$R^3$ and $R^4$ taken together represent —$(CH_2)_n$—, —$(CH_2)_nO(CH_2)_p$—, —$(CH_2)_nNR^b(CH_2)_p$— or —$(CH_2)_nS(=O)_m(CH_2)_p$—;
or $R^1$, $R^2$, $R^3$ and $R^4$ above are selected as follows:
$R^1$ is selected from H, $C_1$-$C_6$ alkyl, $C_3$-$C_6$ cycloalkyl, and $C_1$-$C_6$ haloalkyl;
$R^3$ and $R^2$ taken together represent $(CH_2)_n$, $(CH_2)_nO(CH_2)_p$, $(CH_2)_nNR^b(CH_2)_p$, or $(CH_2)_nS(=O)_m(CH_2)_p$; and
$R^4$ is selected from H, $C_1$-$C_6$ alkyl, $C_3$-$C_6$ cycloalkyl, aryl, heteroaryl, halogen and $C_1$-$C_6$ haloalkyl;
$R^5$ is selected from
(a) H,
(b) $C_1$-$C_6$ alkyl,
(c) aryl,
(d) aralkyl,
(e) $CH(R^7)OC(=O)R^8$,
(f) $CH(R^7)OC(=O)OR^8$, and
(g) a (5-alkyl-2-oxo-1,3-dioxolen-4-yl)methyl group having the following formula:

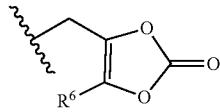

wherein $R^6$ is $C_1$-$C_6$ alkyl;
$R^7$ is hydrogen or $C_1$-$C_6$ alkyl;
R is $C_1$-$C_6$ alkyl or $C_3$-$C_6$-cycloalkyl;
each $R^a$ is independently selected from:
(a) H,
(b) $C_1$-$C_6$ alkyl,
(c) halogen,
(d) aryl,
(e) $OR^b$,
(f) cyano,
(g) heteroaryl,
(h) $C_3$-$C_6$ cycloalkyl, and
(i) $C_1$-$C_6$ haloalkyl;
each $R^{a'}$ is independently selected from:
(a) cyano,
(b) $C_1$-$C_6$ alkyl,
(c) halogen,
(d) aryl,
(e) $OR^b$,
(f) heteroaryl,
(g) $C_3$-$C_6$ cycloalkyl,
(h) $C_1$-$C_6$ haloalkyl;
$R^b$ and $R^c$ are independently selected from:
(a) H,
(b) $C_1$-$C_6$ alkyl,
(c) aryl,
(d) heteroaryl,
(e) $C_3$-$C_6$ cycloalkyl, and
(f) $C_1$-$C_6$ haloalkyl; or
$R^b$ and $R^c$ taken together with the N to which they are both attached form a 3- to 6-membered heterocycle optionally having an additional heteroatom selected from N, O and S;

m is 0, 1, or 2;
n is 1, 2 or 3; and
p is 1, 2 or 3.

In certain embodiments, provided herein are compounds of Formula I:

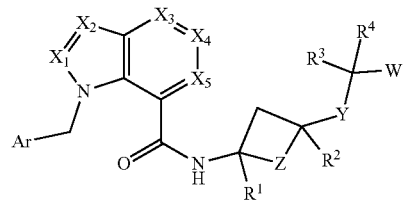

or a pharmaceutically acceptable salt, solvate, solvate of the salt, hydrate, a single stereoisomer, a mixture of stereoisomers, a racemic mixture of stereoisomers, or prodrug thereof, wherein:
Ar is an aryl or a heteroaryl, wherein said aryl and said heteroaryl are each optionally substituted with 1 to 3 substituents independently selected from:
(a) $C_1$-$C_6$ alkyl,
(b) $C_3$-$C_7$ cycloalkyl,
(c) heterocycle,
(d) aryl,
(e) heteroaryl,
(f) halogen,
(g) CN,
(h) $OR^b$,
(i) $N(R^b)C(=O)R^c$,
(j) $C(=O)N(R^b)(R^c)$,
(k) $S(=O)_mR^b$,
(l) $S(=O)_2N(R^b)(R^c)$,
(m) $N(R^b)S(=O)_2R^c$,
(n) $SF_5$; and
(o) $C_1$-$C_6$ haloalkyl.
W is selected from:
(a) $C(=O)OR^5$,
(b) $C(=O)NHOH$,
(c) $S(=O)_2NHR^b$,
(d) $S(=O)_2NHC(=O)R^b$,
(e) $NHC(=O)NHSO_2R^b$,
(f) 1H-tetrazole,
(g) 1,2,4-oxadiazol-5(4H)one,
(h) 1,2,4-thiadiazol-5(4H)one,
(i) 1,2,4-oxadiazole-5(4H)-thione,
(j) 1,2,4-triazole-5(4H)-one,
(k) tetrazol-5(4H)-one, and
(l) $C(=O)NHS(=O)_2R^b$;
$X^1$, $X^2$, $X^3$, $X^4$, and $X^5$ are each independently N or $CR^a$, wherein not more than 2 of $X^1$, $X^2$, $X^3$, $X^4$, and $X^5$ are N;
Y is selected from:
(a) a bond,
(b) $(CH_2)_n$ wherein 1 to 4 hydrogen atoms may be replaced by $R^{a'}$,
(c) O, and
(d) $NR^b$;
Z is $(CH_2)_n$, wherein 1 to 4 hydrogen atoms may be replaced by $R^{a'}$;
$R^1$ and $R^2$ are independently selected from:
(a) H,
(b) $C_1$-$C_6$ alkyl,
(c) $C_3$-$C_6$ cycloalkyl, and
(d) $C_1$-$C_6$ haloalkyl;

wherein $R^2$ is not H; or
$R^1$ and $R^2$ taken together represent —$(CH_2)_n$—, —$(CH_2)_nO(CH_2)_p$—, —$(CH_2)_nNR^b(CH_2)_p$— or —$(CH_2)_nS(=O)_m(CH_2)_p$—;
$R^3$ and $R^4$ are independently selected from:
(a) H,
(b) $C_1$-$C_6$ alkyl,
(c) $C_3$-$C_6$ cycloalkyl,
(d) aryl,
(e) heteroaryl,
(f) halogen,
(g) $C_1$-$C_6$ haloalkyl; or
$R^3$ and $R^4$ taken together represent —$(CH_2)_n$—, —$(CH_2)_nO(CH_2)_p$—, —$(CH_2)_nNR^b(CH_2)_p$— or —$(CH_2)_nS(=O)_m(CH_2)_p$—;
or $R^1$, $R^2$, $R^3$ and $R^4$ above are selected as follows:
$R^1$ is selected from H, $C_1$-$C_6$ alkyl, $C_3$-$C_6$ cycloalkyl, and $C_1$-$C_6$ haloalkyl;
$R^3$ and $R^2$ taken together represent $(CH_2)_n$, $(CH_2)_nO(CH_2)_p$, $(CH_2)_nNR^b(CH_2)_p$, or $(CH_2)_nS(=O)_m(CH_2)_p$; and
$R^4$ is selected from H, $C_1$-$C_6$ alkyl, $C_3$-$C_6$ cycloalkyl, aryl, heteroaryl, halogen and $C_1$-$C_6$ haloalkyl;
$R^5$ is selected from
(a) H,
(b) $C_1$-$C_6$ alkyl,
(c) aryl,
(d) aralkyl,
(e) $CH(R^7)OC(=O)R^8$,
(f) $CH(R^7)OC(=O)OR^8$, and
(g) a (5-alkyl-2-oxo-1,3-dioxolen-4-yl)methyl group having the following formula:

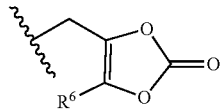

wherein $R^6$ is $C_1$-$C_6$ alkyl;
$R^7$ is hydrogen or $C_1$-$C_6$ alkyl;
$R^8$ is $C_1$-$C_6$ alkyl or $C_3$-$C_6$-cycloalkyl;
each $R^a$ is independently selected from:
(a) H,
(b) $C_1$-$C_6$ alkyl,
(c) halogen,
(d) $OR^b$,
(e) cyano,
(f) $C_3$-$C_6$ cycloalkyl, and
(g) $C_1$-$C_6$ haloalkyl;
each $R^{a'}$ is independently selected from:
(a) $C_1$-$C_6$ alkyl,
(b) halogen, and
(c) $C_1$-$C_6$ haloalkyl;
$R^b$ and $R^c$ are independently selected from:
(a) H,
(b) $C_1$-$C_6$ alkyl,
(c) aryl,
(d) heteroaryl,
(e) $C_3$-$C_6$ cycloalkyl, and
(f) $C_1$-$C_6$ haloalkyl; or
$R^b$ and $R^c$ taken together with the N to which they are both attached form a 3- to 6-membered heterocycle optionally having an additional heteroatom selected from N, O and S;
m is 0, 1, or 2;
n is 1, 2 or 3; and
p is 1, 2 or 3.

In certain embodiments, $X^2$ is C—$R^a$; $X^1$, $X^3$, $X^4$ and $X^5$, are each independently N or $CR^a$; and $R^a$ is selected from H, $C_1$-$C_6$ alkyl, halogen, aryl, $OR^b$, cyano, heteroaryl, $C_3$-$C_6$ cycloalkyl, and $C_1$-$C_6$ haloalkyl.

In yet certain embodiments, $X^2$ and $X^3$ are C—$R^a$; $X^1$, $X^4$ and $X^5$ are each independently N or $CR^a$, wherein not more than 2 of $X^1$, $X^4$ and $X^5$ are N; and $R^a$ is selected from H, $C_1$-$C_6$ alkyl, halogen, aryl, $OR^b$, cyano, heteroaryl, $C_3$-$C_6$ cycloalkyl, and $C_1$-$C_6$ haloalkyl.

In yet certain embodiments, $X^2$ is CH; and $X^3$ is CH or C-(halogen); $X^1$, $X^4$ and $X^5$ are each independently N or $CR^a$, wherein not more than 2 of $X^1$, $X^4$ and $X^5$ are N; and $R^a$ is selected from H, $C_1$-$C_6$ alkyl, halogen, aryl, $OR^b$, cyano, heteroaryl, $C_3$-$C_6$ cycloalkyl, and $C_1$-$C_6$ haloalkyl. In yet certain embodiments, $X^2$ is CH; and $X^3$ is CH or C-(halogen); $X^1$, $X^4$ and $X^5$ are each independently N or CH, wherein not more than 2 of $X^1$, $X^4$ and $X^5$ are N.

In certain embodiments, $X^1$ is N or C—$R^a$; $X^2$, $X^3$, $X^4$ and $X^5$ are C—$R^a$; and $R^a$ is selected from H, $C_1$-$C_6$ alkyl, halogen, aryl, $OR^b$, cyano, heteroaryl, $C_3$-$C_6$ cycloalkyl, and $C_1$-$C_6$ haloalkyl. In yet certain embodiments, $X^1$ is N or CH; $X^2$ is CH or C-(halogen) and $X^3$, $X^4$ and $X^5$ are CH.

In certain embodiments, each of $X^1$, $X^2$, $X^3$, $X^4$ and $X^5$ is independently C—$R^a$, or one of $X^1$, $X^2$, $X^3$, $X^4$ and $X^5$ is N, and the others are each independently C—$R^a$.

In certain embodiments, each of $X^1$, $X^2$, $X^3$, $X^4$ and $X^5$ is independently C—$R^a$. In yet certain embodiments, each of $X^1$, $X^2$, $X^3$, $X^4$ and $X^5$ is independently CH.

In certain embodiments, $R^a$ is H or a halogen atom.
In certain embodiments, Z is —$CH_2$—.
In certain embodiments, Y is a bond or —$CH_2$—.
In certain embodiments, $R^1$ and $R^2$ taken together represent —$CH_2$—, —$CH_2CH_2$— or —$CH_2CH_2CH_2$—.
In certain embodiments, Y is —$CH_2$—, and $R^3$ and $R^2$ taken together represent —$CH_2$—, —$CH_2CH_2$— or —$CH_2CH_2CH_2$—.
In certain embodiments, Z is —$CH_2$—; Y is a bond or —$CH_2$—; $R^1$ and $R^2$ taken together represent —$CH_2$—, —$CH_2CH_2$— or —$CH_2CH_2CH_2$—. In yet certain embodiments, Z is —$CH_2$—; Y is a bond; and $R^1$ and $R^2$ taken together represent —$CH_2$—, —$CH_2CH_2$— or —$CH_2CH_2CH_2$—.
In certain embodiments, Z is —$CH_2$—; Y is a bond or —$CH_2$—; and $R^3$ and $R^2$ taken together represent —$CH_2$—, —$CH_2CH_2$— or —$CH_2CH_2CH_2$—. In yet certain embodiments, Z is —$CH_2$—; Y is a bond; and $R^3$ and $R^2$ taken together represent —$CH_2$—, —$CH_2CH_2$— or —$CH_2CH_2CH_2$—. In yet certain embodiments, Z is —$CH_2$—; Y is a bond; and $R^3$ and $R^2$ taken together represent —$CH_2$—, —$CH_2CH_2$— or —$CH_2CH_2CH_2$—; $R^1$ is H; and $R^4$ is selected from H, $C_1$-$C_6$ alkyl, $C_3$-$C_6$ cycloalkyl, aryl, heteroaryl, halogen and $C_1$-$C_6$ haloalkyl.

In some embodiments, Ar is aryl or heteroaryl optionally substituted with 1 to 3 substituents independently selected from:
(a) halogen,
(b) cyano,
(c) $C_1$-$C_6$ alkyl,
(d) $SF_5$,
(e) $C_1$-$C_6$ haloalkyl,
(f) $OR^b$ wherein $R^b$ is $C_1$-$C_6$ alkyl, aryl, heteroaryl, $C_3$-$C_6$ cycloalkyl or $C_1$-$C_6$ haloalkyl,
(g) heterocycle,
(h) aryl, and
(i) heteroaryl.

In certain embodiments, W is selected from:
(a) C(=O)OR$^5$,
(b) C(=O)NHOH,
(c) S(=O)$_2$NHR$^b$,
(d) S(=O)$_2$NHC(=O)R$^b$,
(e) NHC(=O)NHSO$_2$R$^b$,
(f) 1H-tetrazole,
(g) 1,2,4-oxadiazol-5(4H)one,
(h) 1,2,4-thiadiazol-5(4H)one,
(i) 1,2,4-oxadiazole-5(4H)-thione,
(j) 1,2,4-triazole-5(4H)-one,
(k) tetrazol-5(4H)-one, and
(l) C(=O)NHS(=O)$_2$R$^b$, R$^5$ is selected from
(h) H,
(i) C$_1$-C$_6$ alkyl,
(j) aryl,
(k) aralkyl,
(l) CH(R$^7$)OC(=O)R$^8$,
(m) CH(R$^7$)OC(=O)OR$^8$, and
(n) a (5-alkyl-2-oxo-1,3-dioxolen-4-yl)methyl group having the following formula:

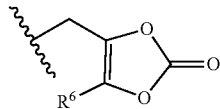

wherein R$^6$ is C$_1$-C$_6$ alkyl; and

R$^b$ is selected from:
(a) H,
(b) C$_1$-C$_6$ alkyl,
(c) aryl,
(d) heteroaryl,
(e) C$_3$-C$_6$ cycloalkyl, and
(f) C$_1$-C$_6$ haloalkyl.

In certain embodiments, W is CO$_2$H or 1H-tetrazole.

In some embodiments, the compound is selected from the group consisting of:

2-(3-(1-(4-cyanobenzyl)-1H-indole-7-carboxamido)bicyclo[1.1.1]pentan-1-yl)acetic acid;
2-(3-(1-(4-(trifluoromethyl)benzyl)-1H-indole-7-carboxamido)bicyclo[1.1.1]pentan-1-yl)acetic acid;
2-(3-(1-(4-(trifluoromethyl)benzyl)-1H-pyrrolo[3,2-b]pyridine-7-carboxamido)bicyclo[1.1.1]-pentan-1-yl)acetic acid;
2-(3-(1-(4-(trifluoromethyl)benzyl)-1H-pyrrolo[3,2-c]pyridine-7-carboxamido)bicyclo[1.1.1]-pentan-1-yl)acetic acid;
2-(3-(1-(4-(trifluoromethyl)benzyl)-1H-pyrrolo[2,3-c]pyridine-7-carboxamido)bicyclo[1.1.1]-pentan-1-yl)acetic acid;
2-(3-(1-(4-(trifluoromethyl)benzyl)-1H-indazole-7-carboxamido)bicyclo[1.1.1]pentan-1-yl)acetic acid;
2-(3-(1-((4-(trifluoromethyl)phenyl)methyl-d$_2$)-1H-indole-7-carboxamido)bicyclo[1.1.1]pentan-1-yl)acetic acid;
6-(1-(4-(trifluoromethyl)benzyl)-1H-indole-7-carboxamido)spiro[3.3]heptane-2-carboxylic acid;
(R)-6-(1-(4-(trifluoromethyl)benzyl)-1H-indole-7-carboxamido)spiro[3.3]heptane-2-carboxylic acid;
(S)-6-(1-(4-(trifluoromethyl)benzyl)-1H-indole-7-carboxamido)spiro[3.3]heptane-2-carboxylic acid;
rac-6-(1-(4-(trifluoromethyl)benzyl)-1H-pyrrolo[3,2-b]pyridine-7-carboxamido)spiro[3.3]-heptane-2-carboxylic acid;
(R)-6-(1-(4-(trifluoromethyl)benzyl)-1H-pyrrolo[3,2-b]pyridine-7-carboxamido)spiro[3.3]-heptane-2-carboxylic acid;
(S)-6-(1-(4-(trifluoromethyl)benzyl)-1H-pyrrolo[3,2-b]pyridine-7-carboxamido)spiro[3.3]-heptane-2-carboxylic acid;
6-(1-(4-(trifluoromethyl)benzyl)-1H-pyrrolo[3,2-c]pyridine-7-carboxamido)spiro[3.3]heptane-2-carboxylic acid;
(R)-6-(1-(4-(trifluoromethyl)benzyl)-1H-pyrrolo[3,2-c]pyridine-7-carboxamido)spiro[3.3]-heptane-2-carboxylic acid;
(S)-6-(1-(4-(trifluoromethyl)benzyl)-1H-pyrrolo[3,2-c]pyridine-7-carboxamido)spiro[3.3]-heptane-2-carboxylic acid; rac-6-(1-(4-(trifluoromethyl)benzyl)-1H-pyrrolo[2,3-c]pyridine-7-carboxamido)spiro[3.3]heptane-2-carboxylic acid;
(R)-6-(1-(4-(trifluoromethyl)benzyl)-1H-pyrrolo[2,3-c]pyridine-7-carboxamido)spiro[3.3]-heptane-2-carboxylic acid;
(S)-6-(1-(4-(trifluoromethyl)benzyl)-1H-pyrrolo[2,3-c]pyridine-7-carboxamido)spiro[3.3]-heptane-2-carboxylic acid;
rac-6-(1-(4-(trifluoromethyl)benzyl)-1H-indazole-7-carboxamido)spiro[3.3]heptane-2-carboxylic acid;
(R)-6-(1-(4-(trifluoromethyl)benzyl)-1H-indazole-7-carboxamido)spiro[3.3]heptane-2-carboxylic acid;
(S)-6-(1-(4-(trifluoromethyl)benzyl)-1H-indazole-7-carboxamido)spiro[3.3]heptane-2-carboxylic acid;
rac-6-(1-(4-(trifluoromethyl)benzyl)-1H-benzo[d]imidazole-7-carboxamido)spiro[3.3]heptane-2-carboxylic acid;
(R)-6-(1-(4-(trifluoromethyl)benzyl)-1H-benzo[d]imidazole-7-carboxamido)spiro[3.3]heptane-2-carboxylic acid;
(R)-6-(1-(4-(trifluoromethyl)benzyl)-1H-benzo[d]imidazole-7-carboxamido)spiro[3.3]heptane-2-carboxylic acid;
3-(3-(1-(4-(trifluoromethyl)benzyl)-1H-indole-7-carboxamido)bicyclo[1.1.1]pentan-1-yl)propanoic acid;
3-(3-methyl-3-(1-(4-(trifluoromethyl)benzyl)-1H-indole-7-carboxamido)cyclobutyl)propanoic acid;
cis-3-(3-methyl-3-(1-(4-(trifluoromethyl)benzyl)-1H-indole-7-carboxamido)cyclobutyl)-propanoic acid;
N-(3-(2-oxo-2-(phenylsulfonamido)ethyl)bicyclo[1.1.1]pentan-1-yl)-1-(4-(trifluoromethyl)benzyl)-1H-indole-7-carboxamide;
N-(3-((3-(phenylsulfonyl)ureido)methyl)bicyclo[1.1.1]pentan-1-yl)-1-(4-(trifluoromethyl)benzyl)-1H-indole-7-carboxamide;
N-(3-((1H-tetrazol-5-yl)methyl)bicyclo[1.1.1]pentan-1-yl)-1-(4-(trifluoromethyl)benzyl)-1H-indole-7-carboxamide;
2-(4-(1-(4-(trifluoromethyl)benzyl)-1H-indole-7-carboxamido)bicyclo[2.1.1]hexan-1-yl)acetic acid;
6-(4-fluoro-1-(4-(trifluoromethyl)benzyl)-1H-indole-7-carboxamido)spiro[3.3]heptane-2-carboxylic acid;
(R)-6-(4-fluoro-1-(4-(trifluoromethyl)benzyl)-1H-indole-7-carboxamido)spiro[3.3]heptane-2-carboxylic acid;
(S)-6-(4-fluoro-1-(4-(trifluoromethyl)benzyl)-1H-indole-7-carboxamido)spiro[3.3]heptane-2-carboxylic acid;
rac-6-(5-fluoro-1-(4-(trifluoromethyl)benzyl)-1H-indole-7-carboxamido)spiro[3.3]heptane-2-carboxylic acid;
(R)-6-(5-fluoro-1-(4-(trifluoromethyl)benzyl)-1H-indole-7-carboxamido)spiro[3.3]heptane-2-carboxylic acid;
(S)-6-(5-fluoro-1-(4-(trifluoromethyl)benzyl)-1H-indole-7-carboxamido)spiro[3.3]heptane-2-carboxylic acid;
rac-6-(5-chloro-1-(4-(trifluoromethyl)benzyl)-1H-indole-7-carboxamido)spiro[3.3]heptane-2-carboxylic acid;
(R)-6-(5-chloro-1-(4-(trifluoromethyl)benzyl)-1H-indole-7-carboxamido)spiro[3.3]heptane-2-carboxylic acid;

(S)-6-(5-chloro-1-(4-(trifluoromethyl)benzyl)-1H-indole-7-carboxamido)spiro[3.3]heptane-2-carboxylic acid;
rac-6-(6-fluoro-1-(4-(trifluoromethyl)benzyl)-1H-indole-7-carboxamido)spiro[3.3]heptane-2-carboxylic acid;
(R)-6-(6-fluoro-1-(4-(trifluoromethyl)benzyl)-1H-indole-7-carboxamido)spiro[3.3]heptane-2-carboxylic acid;
(S)-6-(6-fluoro-1-(4-(trifluoromethyl)benzyl)-1H-indole-7-carboxamido)spiro[3.3]heptane-2-carboxylic acid;
rac-6-(1-(4-cyanobenzyl)-1H-indole-7-carboxamido)spiro[3.3]heptane-2-carboxyli c acid;
(R)-6-(1-(4-cyanobenzyl)-1H-indole-7-carboxamido)spiro[3.3]heptane-2-carboxylic acid;
(S)-6-(1-(4-cyanobenzyl)-1H-indole-7-carboxamido)spiro[3.3]heptane-2-carboxylic acid;
rac-6-(1-(4-(difluoromethyl)benzyl)-1H-indole-7-carboxamido)spiro[3.3]heptane-2-carboxyli c acid;
(R)-6-(1-(4-(difluoromethyl)benzyl)-1H-indole-7-carboxamido)spiro[3.3]heptane-2-carboxyli c acid;
(S)-6-(1-(4-(difluoromethyl)benzyl)-1H-indole-7-carboxamido)spiro[3.3]heptane-2-carboxylic acid;
2-(4-(1-(4-(difluoromethyl)benzyl)-1H-indole-7-carboxamido)bicyclo[2.1.1]hexan-1-yl)acetic acid;
2-(3-(4-fluoro-1-(4-(trifluoromethyl)benzyl)-1H-indole-7-carboxamido)bicyclo[1.1.1]pentan-1-yl)acetic acid;
2-(4-fluoro-1-(4-(trifluoromethyl)benzyl)-1H-indole-7-carboxamido)bicyclo[2.1.1]hexan-1-yl)acetic acid;
2-(4-(1-((4-(pentafluorothiol)phenyl)methyl)-1H-indole-7-carboxamido)bicyclo[2.1.1]hexan-1-yl)acetic acid;
rac-6-(1-((4-(pentafluorothiol)phenyl)methyl)-1H-indole-7-carboxamido)spiro[3.3]heptane-2-carboxylic acid;
rac-6-(1-(4-(difluoromethyl)benzyl)-4-fluoro-1H-indole-7-carboxamido)spiro[3.3]heptane-2-carboxylic acid;
2-(3-(1-(4-(difluoromethyl)benzyl)-4-fluoro-1H-indole-7-carboxamido)bicyclo[1.1.1]pentan-1-yl)acetic acid;
2-(3-(5-fluoro-1-(4-(trifluoromethyl)benzyl)-1H-indole-7-carboxamido)bicyclo[1.1.1]pentan-1-yl)acetic acid;
2-(3-(1-([1,1'-biphenyl]-4-ylmethyl)-1H-indole-7-carboxamido)bicyclo[1.1.1] pentan-1-yl)acetic acid;
2-(3-(1-([1,1'-biphenyl]-4-ylmethyl)-4-fluoro-1H-indole-7-carboxamido)bicyclo[1.1.1] pentan-1-yl)acetic acid;
2-(3-(1-([1,1'-biphenyl]-4-ylmethyl)-1H-indazole-7-carboxamido)bicyclo[1.1.1] pentan-1-yl)acetic acid;
2-(3-(1-(4-(trifluoromethoxy)benzyl)-1H-indazole-7-carboxamido)bicyclo[1.1.1] pentan-1-yl)acetic acid;
2-(3-(4-fluoro-1-(4-iodobenzyl)-1H-indole-7-carboxamido) bicyclo[1.1.1]pentan-1-yl) acetic acid;
2-(3-(4-fluoro-1-(4-(pyridine-4-yl)benzyl)-1H-indole-7-carboxamido)bicyclo[1.1.1]pentan-1-yl) acetic acid; and
2-(3-(4-fluoro-1-(4-morpholinobenzyl)-1H-indole-7-carboxamido)bicyclo[1.1.1]pentan-1-yl) acetic acid;
or a pharmaceutically acceptable salt, solvate, solvate of the salt or prodrug thereof.

Some embodiments provided herein describe pharmaceutical compositions comprising a compound of any of the preceding embodiments, and a pharmaceutically acceptable carrier. In some embodiments, the pharmaceutical composition comprises a compound of Formula I, Formula Ia, Formula Ib, Formula Ic, or Formula Id, or a pharmaceutically acceptable salt, solvate, solvate of the salt or prodrug thereof, and a pharmaceutically acceptable carrier.

Some embodiments provided herein describe methods for the treatment of cancer comprising administering to a patient in need thereof a compound or a pharmaceutical composition of any of the preceding embodiments. In some embodiments, the compound is a compound of Formula I, Formula Ia, Formula Ib, Formula Ic, or Formula Id. In some embodiments, the composition comprises a pharmaceutically acceptable carrier and a compound of Formula I, Formula Ia, Formula Ib, Formula Ic, or Formula Id, or a pharmaceutically acceptable salt, solvate, solvate of the salt or prodrug thereof.

In some embodiments, the cancer is selected from the group consisting of glioblastoma, bone cancer, head and neck cancer, melanoma, basal cell carcinoma, squamous cell carcinoma, adenocarcinoma, oral cancer, esophageal cancer, gastric cancer, intestinal cancer, colon cancer, bladder cancer, hepatocellular carcinoma, renal cell carcinoma, pancreatic cancer, ovarian cancer, cervical cancer, lung cancer, breast cancer, and prostate cancer.

In some embodiments, the treatment further comprises an additional agent selected from an anti-PD-1 antibody and an anti-PD-L1 antibody.

In some instances within any of the preceding embodiments, for compounds of Formulae I, Ia and Ib, Ar is substituted phenyl. Examples of substituents for phenyl include CN, halomethyl (such as $CF_3$ and $CHF_2$) and $SF_5$. In some embodiments, the substituents for phenyl are CN (cyano), halogen, haloalkyl, phenyl, pyridyl, haloalkoxy, heterocycle, or $SF_5$.

In some embodiments, each $X^1$, $X^2$, $X^3$, $X^4$ and $X^5$ is independently C—$R^a$, or one of $X^1$, $X^2$, $X^3$, $X^4$ and $X^5$ is N, and the others are each independently C—$R^a$; and $R^a$ is selected from H and halogen (such as chloro and fluoro). Thus, each $R^a$ may be the same or different from the other $R^a$s. In one instance, $X^1$, $X^2$, $X^3$, $X^4$ and $X^5$ are each CH. In another instance, one of $X^1$, $X^2$, $X^3$, $X^4$ and $X^5$ is —C(F)— or —C(Cl)— and the others are each CH.

In some instances within any of the preceding embodiments, for compounds of Formulae I, Ia and Ib, $R^1$ and $R^2$ together is —$CH_2$—.

In some instances within any of the preceding embodiments, for compounds of Formulae I, Ia and Ib, $R^3$ and $R^2$ together is —$CH_2$—.

In some instances within any of the preceding embodiments, for compounds of Formulae I, Ia and Ib W is —$CO_2H$, —$CONHSO_2$-phenyl, —$NHCONHSO_2$-phenyl, and tetrazolyl. In one instance W is —$CO_2H$. In another instance W is tetrazolyl.

Any of the features of an embodiment is applicable to all embodiments identified herein. Moreover, any of the features of an embodiment is independently combinable, partly or wholly with other embodiments described herein in any way, e.g., one, two, or three or more embodiments may be combinable in whole or in part. Further, any of the features of an embodiment may be made optional to other embodiments. Any embodiment of a method can comprise another embodiment of a compound, and any embodiment of a compound can be configured to perform a method of another embodiment.

Definitions

Unless defined otherwise, all technical and scientific terms used herein have the same meaning as is commonly understood by one of ordinary skill in the art. All patents, applications, published applications and other publications referenced herein are incorporated by reference in their entirety unless stated otherwise. In the event that there are a plurality of definitions for a term herein, those in this section prevail unless stated otherwise.

As used in the specification and the appended claims, the singular forms "a," "an" and "the" include plural referents unless the context clearly dictates otherwise. Unless otherwise indicated, conventional methods of mass spectroscopy, NMR, HPLC, protein chemistry, biochemistry, recombinant DNA techniques and pharmacology are employed. The use of "or" or "and" means "and/or" unless stated otherwise. Furthermore, use of the term "including" as well as other forms, such as "include", "includes," and "included," is not limiting. As used in this specification, whether in a transitional phrase or in the body of the claim, the terms "comprise(s)" and "comprising" are to be interpreted as having an open-ended meaning. That is, the terms are to be interpreted synonymously with the phrases "having at least" or "including at least." When used in the context of a process, the term "comprising" means that the process includes at least the recited steps, but may include additional steps. When used in the context of a compound, composition, or device, the term "comprising" means that the compound, composition, or device includes at least the recited features or components, but may also include additional features or components.

The term "patient" includes mammals such as mice, rats, cows, sheep, pigs, rabbits, goats, horses, monkeys, dogs, cats, and humans. In some embodiments, the patient is a human.

The term "halo" or "halogen" refers to any radical of fluorine, chlorine, bromine or iodine.

The term "alkyl" refers to a saturated hydrocarbon chain that may be a straight chain or branched chain, containing the indicated number of carbon atoms. For example, $C_1$-$C_6$ alkyl indicates that the group may have from 1 to 6 (inclusive) carbon atoms in it. In some embodiments, an alkyl is a $C_1$-$C_6$ alkyl which represents a straight-chain or branched saturated hydrocarbon radical having 1 to 6 carbon atoms. Examples of alkyl include without limitation methyl, ethyl, n-propyl, isopropyl, n-butyl, isobutyl, sec-butyl, and tert-butyl.

The term "cycloalkyl" refers to a fully saturated monocyclic, bicyclic, tricyclic or other polycyclic hydrocarbon group having the indicated number of ring carbon atoms. Multicyclic cycloalkyl may be fused, bridged or spiro ring systems. Cycloalkyl groups include, but are not limited to, cyclopropyl, cyclobutyl, cyclopentyl, cyclohexyl, cycloheptyl, cyclooctyl and norbornyl. In some embodiments, cycloalkyl is a monocyclic $C_3$-$C_8$ cycloalkyl.

The term "haloalkyl" refers to an alkyl group in which at least one hydrogen atom is replaced by halo. In some embodiments, more than one hydrogen atom (e.g., 2, 3, 4, 5 or 6) are replaced by halo. In these embodiments, the hydrogen atoms can each be replaced by the same halogen (e.g., fluoro) or the hydrogen atoms can be replaced by a combination of different halogens (e.g., fluoro and chloro). "Haloalkyl" also includes alkyl moieties in which all hydrogens have been replaced by halo (sometimes referred to herein as perhaloalkyl, e.g., perfluoroalkyl, such as trifluoromethyl).

As referred to herein, the term "alkoxy" refers to a group of formula —O-(alkyl). Alkoxy can be, for example, methoxy, ethoxy, propoxy, isopropoxy, butoxy, iso-butoxy, sec-butoxy, pentoxy, 2-pentoxy, 3-pentoxy, or hexyloxy. Likewise, the term "thioalkoxy" refers to a group of formula —S-(alkyl). The terms "haloalkoxy" and "thiohaloalkoxy" refer to —O-(haloalkyl) and —S-(haloalkyl), respectively.

The term "aralkyl" refers to an alkyl moiety in which an alkyl hydrogen atom is replaced by an aryl group. One of the carbons of the alkyl moiety serves as the point of attachment of the aralkyl group to another moiety. Non-limiting examples of "aralkyl" include benzyl, 2-phenylethyl, and 3-phenylpropyl groups.

The term "alkenyl" refers to a straight or branched hydrocarbon chain containing the indicated number of carbon atoms and having one or more carbon-carbon double bonds. Alkenyl groups can include, e.g., vinyl, allyl, 1-butenyl, and 2-hexenyl. In some embodiments, an alkenyl is a $C_2$-$C_6$ alkenyl.

The term "alkynyl" refers to a straight or branched hydrocarbon chain containing the indicated number of carbon atoms and having one or more carbon-carbon triple bonds. Alkynyl groups can include, e.g., ethynyl, propargyl, 1-butynyl, and 2-hexynyl. In some embodiments, an alkynyl is a $C_2$-$C_6$ alkynyl.

The term "heterocycle", "heterocyclyl" or "heterocyclic" as used herein except where noted, represents a stable 4-, 5-, 6- or 7-membered monocyclic- or a stable 6-, 7-, 8-, 9-, 10-, 11-, or 12-membered bicyclic heterocyclic ring system which comprises at least one non-aromatic (i.e. saturated or partially unsaturated) ring which consists of carbon atoms and from one to four, preferably up to three, heteroatoms selected from the group consisting of N, O and S, wherein the nitrogen and sulfur atoms may optionally be oxidized as N-oxide, sulfoxide or sulfone, and wherein the nitrogen atom may optionally be quaternized. A heterocycle can be bonded via a ring carbon atom or, if available, via a ring nitrogen atom. Bicyclic heterocyclic ring systems may be fused, bridged, or spiro bicyclic heterocyclic ring system(s). In some embodiments, heterocyclyl is monocyclic having 4 to 7, preferably 4 to 6, ring atoms, of which 1 or 2 are heteroatoms independently selected from the group consisting of N, O and S. In some embodiments, a heterocyclyl group is bicyclic, and in which case, the second ring may be an aromatic or a non-aromatic ring which consists of carbon atoms and from one to four, preferably up to three, heteroatoms independently selected from the group consisting of N, O and S, or the second ring may be a benzene ring, or a "cycloalkyl", or a "cycloalkenyl", as defined herein. Examples of such heterocyclic groups include, but are not limited to azetidine, chroman, dihydrofuran, dihydropyran, dioxane, dioxolane, hexahydroazepine, imidazolidine, imidazoline, indoline, isochroman, isoindoline, isothiazoline, isothiazolidine, isoxazoline, isoxazolidine, morpholine, oxazoline, oxazolidine, oxetane, piperazine, piperidine, dihydropyridine, tetrahydropyridine, dihydropyridazine, pyran, pyrazolidine, pyrazoline, pyrrolidine, pyrroline, tetrahydrofuran, tetrahydropyran, thiamorpholine, tetrahydrothiophene, thiazoline, thiazolidine, thiomorpholine, thietane, thiolane, sulfolane, 1,3-dioxolane, 1,3-oxazolidine, 1,3-thiazolidine, tetrahydrothiopyran, tetrahydrotriazine, 1,3-dioxane, 1,4-dioxane, hexahydrotriazine, tetrahydro-oxazine, tetrahydropyrimidine, perhydroazepine, perhydro-1,4-diazepine, perhydro-1,4-oxazepine, 7-azabicyclo[2.2.1]heptane, 3-azabicyclo[3.2.0]heptane, 7-azabicyclo[4.1.0]heptane, 2,5-diazabicyclo[2.2.1]heptane, 2-oxa-5-azabicyclo[2.2.1]heptane, tropane, 2-oxa-6-azaspiro[3.3]heptane, dihydrobenzofuran, diydrobenzimidazolyl, dihydrobenzoxazole, and dihydrobenzothiazolyl, and N-oxides or sulfones or sulfoxides thereof.

The term "aryl" as used herein, is intended to mean any stable monocyclic or bicyclic carbon ring of up to 6 members in each ring (i.e., 6 to 10 total ring atoms) wherein at least one ring is aromatic. For example, a $C_6$-$C_{10}$ aryl group such asphenyl, naphthyl, tetrahydronaphthyl, indanyl, or 1H-indenyl. Unless stated otherwise specifically in the specification, the term "aryl" is meant to include aryl radicals optionally substituted by one or more substituents independently selected from CN (cyano), halogen, haloalkyl, —OR$^x$, —N(R$^x$)$_2$—, or alkyl; wherein each R$^x$ is independently H, alkyl, haloalkyl, cycloalkyl, or heterocyclyl.

The term "heteroaryl", as used herein except where noted, represents a stable 5-, 6- or 7-membered monocyclic- or stable 9- or 10-membered fused bicyclic ring system which comprises at least one aromatic ring, which consists of carbon atoms and from one to four, preferably up to three, heteroatoms selected from the group consisting of N, O and S wherein the nitrogen and sulfur heteroatoms may optionally be oxidized, and the nitrogen heteroatom may optionally be quaternized. In the case of a "heteroaryl" which is a bicyclic group, the second ring need not be aromatic and need not comprise a heteroatom. Accordingly, bicyclic "heteroaryl" includes, for example, a stable 5- or 6-membered monocyclic aromatic ring consisting of carbon atoms and from one to four, preferably up to three, heteroatoms, as defined immediately above, fused to a benzene ring, or a second monocyclic "heteroaryl", or a "heterocyclyl", a "cycloalkyl", or a "cycloalkenyl", as defined above. Examples of heteroaryl groups include, but are not limited to, benzimidazole, benzopyrazole, benzisothiazole, benzisoxazole, benzofuran, isobenzofuran, benzothiazole, benzothiophene, benzotriazole, benzoxazole, cinnoline, furan, furazan, imidazole, indazole, indole, indolizine, isoquinoline, isothiazole, isoxazole, naphthyridine, oxadiazole, oxazole, phthalazine, pteridine, purine, pyrazine, pyrazole, pyridazine, pyridine, pyrimidine, pyrrole, quinazoline, quinoline, quinoxaline, tetrazole, thiadiazole, thiazole, thiophene, triazine, triazole, benzimidazole, benzothiadiazole, isoindole, pyrrolopyridines, imidazopyridines such as imidazo[1,2-a]pyridine, pyrazolopyridine, pyrrolopyrimidine and N-oxides thereof. Unless stated otherwise specifically in the specification, the term "heteroaryl" is meant to include heteroaryl radicals optionally substituted by one or more substituents independently selected from CN (cyano), halogen, haloalkyl, —OR$^x$, —N(R$^x$)$_2$—, or alkyl; wherein each R$^x$ is independently H, alkyl, haloalkyl, cycloalkyl, or heterocyclyl.

The term "treating", "treat", or "treatment" refers generally to controlling, alleviating, ameliorating, slowing the progress of or eliminating a named condition once the condition has been established. In addition to its customary meaning, the term "preventing", "prevent", or "prevention" also refers to delaying the onset of, or reducing the risk of developing a named condition or of a process that can lead to the condition, or the recurrence of symptoms of a condition.

The term "therapeutically effective amount" or "effective amount" is an amount sufficient to effect beneficial or desired clinical results. An effective amount can be administered in one or more administrations. An effective amount is typically sufficient to palliate, ameliorate, stabilize, reverse, slow or delay the progression of the disease state.

As used herein, the abbreviations for any protective groups, amino acids and other compounds, are, unless indicated otherwise, in accord with their common usage, recognized abbreviations, or the IUPAC-IUB Commission on Biochemical Nomenclature (See, Biochem. 11:942-944 (1972)).

Compound Forms and Salts

In some embodiments, the compounds described herein contain one or more asymmetric centers and thus occur as racemates and racemic mixtures, enantiomerically enriched mixtures, single enantiomers, individual diastereomers and diastereomeric mixtures. In some embodiments, the compounds described herein, either by nature of asymmetric centers or by restricted rotation, be present in the form of isomers (e.g., enantiomers, diastereomers).

It will also be appreciated that when two or more asymmetric centers are present in the compounds of the disclosure, several diastereomers and enantiomers of the exemplified structures will often be possible, and that pure diastereomers and pure enantiomers represent preferred embodiments. It is intended that pure stereoisomers, pure diastereomers, pure enantiomers, and mixtures thereof, are within the scope of the disclosure. When compounds contains stereochemistry, the compounds are designated as '(racemic)' or "rac" if the stereoisomers have not been separated and '(R) or (S)' if the stereoisomers have been resolved. In certain embodiments, the compounds disclosed herein contain axial chirality, particularly in the case of the spirocyclic[3.3]heptane containing compounds. These have also been designed as either '(R) or (S)' when there is a single stereoisomer, rather than the IUPAC convention of '(aR) or (aS)', where the 'a' denotes axial chirality.

All isomers, whether separated, pure, partially pure, or in racemic mixture, of the compounds of this disclosure are encompassed within the scope of this disclosure. The purification of said isomers and the separation of said isomeric mixtures may be accomplished by standard techniques known in the art. For example, diastereomeric mixtures can be separated into the individual isomers by chromatographic processes or crystallization, and racemates can be separated into the respective enantiomers either by chromatographic processes on chiral phases or by resolution.

The compounds of the present disclosure include all cis, trans, syn, anti, entgegen (E), and zusammen (Z) isomers as well as mixtures thereof. In some embodiments, the compounds described herein exist in multiple tautomeric forms. In such instances, the present disclosure expressly includes all tautomeric forms of the compounds described herein, even though only a single tautomeric form may be represented. In addition, where a term used in the present disclosure encompasses a group that may tautomerize, all tautomeric forms are expressly included thereunder. For example, hydroxy substituted heteroaryl includes 2-hydroxypyridine as well as 2-pyridone, 1-hydroxyisoquinoline as well as 1-oxo-1,2-dihyroisoquinoline, and the like. All such isomeric forms of such compounds are expressly included in the present disclosure.

The compounds of the present disclosure include the compounds themselves, as well as their salts, solvate, solvate of the salt and their prodrugs, if applicable. Salts for the purposes of the present disclosure are preferably pharmaceutically acceptable salts of the compounds according to the present disclosure. Salts which are not themselves suitable for pharmaceutical uses but can be used, for example, for isolation or purification of the compounds according to the disclosure are also included. A salt, for example, can be formed between an anion and a positively charged substituent (e.g., amino) on a compound described herein. Suitable anions include chloride, bromide, iodide, sulfate, nitrate, phosphate, citrate, methanesulfonate, trifluoroacetate, and acetate. Likewise, a salt can also be formed between a cation and a negatively charged substituent (e.g., carboxylate) on a compound described herein. Suitable cations include sodium ion, potassium ion, magnesium ion, calcium ion, and an ammonium cation such as tetramethylammonium ion.

As used herein, "pharmaceutically acceptable salts" refer to derivatives wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. When the compound of the present disclosure is basic, pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfonic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, benzenesulfonic, toluenesulfonic, naphthalenedisulfonic, methanesulfonic, ethanesulfonic, ethanedisulfonic, camphorsulfonic, gluconic, mandelic, mucic, pantothenic, oxalic, isethionic, and the like.

When the compound of the present disclosure is acidic, salts may be prepared from pharmaceutically acceptable non-toxic bases, including inorganic and organic bases. In some embodiments, the pharmaceutically acceptable salt is lithium salt, sodium salt, potassium salt, magnesium salt, calcium salt, dicyclohexylamine salt, N-methyl-D-glucamine salt, tris(hydroxymethyl)methylamine salt, arginine salt, lysine salt, and the like.

Lists of suitable salts may be found in Remington's Pharmaceutical Sciences, 17th ed., Mack Publishing Company, Easton, Pa., 1985, p. 1418; S. M. Berge et al., "Pharmaceutical Salts", J. Pharm. Sci. 1977, 66, 1-19; and "Pharmaceutical Salts: Properties, Selection, and Use. A Handbook"; Wermuth, C. G. and Stahl, P. H. (eds.) Verlag Helvetica Chimica Acta, Zurich, 2002 [ISBN 3-906390-26-8]; each of which is incorporated herein by reference in its entirety.

Solvates in the context of the present disclosure are designated as those forms of the compounds according to the present disclosure which form a complex in the solid or liquid state by stoichiometric coordination with solvent molecules. Hydrates are a specific form of solvates, in which the coordination takes place with water. Hydrates are preferred solvates in the context of the present disclosure. The formation of solvates is described in greater detail in "Solvents and Solvent Effects in Organic Chemistry"; Reichardt, C. and Welton T.; John Wiley & Sons, 2011 [ISBN: 978-3-527-32473-6], the contents of which is incorporated herein by reference in its entirety. A person of ordinary skill in the art would recognize the solvates of the present disclosure.

The present disclosure also encompasses all suitable isotopic variants of the compounds according to the present disclosure, whether radioactive or not. An isotopic variant of a compound according to the present disclosure is understood to mean a compound in which at least one atom within the compound according to the present disclosure has been exchanged for another atom of the same atomic number, but with a different atomic mass than the atomic mass which usually or predominantly occurs in nature. Examples of isotopes which can be incorporated into a compound according to the present disclosure are those of hydrogen, carbon, nitrogen, oxygen, fluorine, chlorine, bromine and iodine, such as $^2$H (deuterium), $^3$H (tritium), $^{13}$C, $^{14}$C, $^{15}$N, $^{17}$O, $^{18}$O, $^{18}$F, $^{36}$Cl, $^{82}$Br, $^{123}$I, $^{124}$I, $^{125}$I, $^{129}$I and $^{131}$I. Particular isotopic variants of a compound according to the present disclosure, especially those in which one or more radioactive isotopes have been incorporated, may be beneficial, for example, for the examination of the mechanism of action or of the active compound distribution in the body. Due to comparatively easy preparability and detectability, especially compounds labelled with $^3$H, $^{14}$C and/or $^{18}$F isotopes are suitable for this purpose. In addition, the incorporation of isotopes, for example of deuterium, can lead to particular therapeutic benefits as a consequence of greater metabolic stability of the compound, for example an extension of the half-life in the body or a reduction in the active dose required. Such modifications of the compounds according to the present disclosure may therefore in some cases also constitute a preferred embodiment of the present disclosure. In some embodiments, hydrogen atoms of the compounds described herein may be replaced with deuterium atoms. Isotopic variants of the compounds according to the present disclosure can be prepared by processes known to those skilled in the art, for example by the methods described below and the methods described in the working examples, by using corresponding isotopic modifications of the particular reagents and/or starting compounds therein.

The present disclosure includes within its scope prodrugs of the compounds of Formula I, and Formulae Ia, Ib, Ic, and Id. Prodrugs are generally drug precursors that, following administration to a subject are converted to an active, or a more active species via some process, such as conversion by chemical hydrolysis or a metabolic pathway. Thus, in the methods of treatment of the present disclosure, the terms "administration of" or "administering a" compound shall encompass the treatment of the various conditions described with the compound specifically disclosed or with a compound which may not be specifically disclosed, but which converts to the specified compound in vivo after administration to the patient. Conventional procedures for the selection and preparation of suitable prodrug derivatives are described, for example, in "Design of Prodrugs," ed. H. Bundgaard, Elsevier, 1985 (Amsterdam, NL), the contents of which is incorporated herein by reference in its entirety. Examples of prodrugs include $C_1$-$C_6$ alkyl esters of carboxylic acid group, which, upon administration to a subject, are capable of providing active compounds.

Pharmaceutical Compositions

The term "pharmaceutical composition" as used herein is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present disclosure encompass any composition made by admixing a compound of the present disclosure, or a pharmaceutically acceptable salt, or solvate or solvate of the salt thereof, and a pharmaceutically acceptable carrier.

The term "pharmaceutically acceptable carrier" refers to a carrier or an adjuvant that may be administered to a patient, together with a compound of the present disclosure, or a pharmaceutically acceptable salt, solvate, salt of the solvate or prodrug thereof, and which does not destroy the pharmacological activity thereof and is nontoxic when administered in doses sufficient to deliver a therapeutic amount of the compound.

In some embodiments, the compounds of the present application are administered at about 1 mg to 1,000 mg, about 2 mg to 900 mg, about 3 mg to 800 mg, about 4 mg to 700 mg, about 5 mg to 600 mg, about 10 mg to 500 mg, about 50 mg to 400 mg, about 100 mg to 300 mg, about 150 mg to 250 mg, or any value in between. In some embodiments, the total daily dosage may be divided and administered in portions during the day, for example, once per day, twice per day, three times per day or four times per day. In some embodiments, the total dosage may be administered once per week, twice per week, three times per week, four times per week, five times per week or six times per week.

In some embodiments, the pharmaceutical compositions of the present disclosure for injection comprise pharmaceutically acceptable sterile aqueous or non-aqueous solutions, dispersions, suspensions or emulsions as well as sterile powders for reconstitution into sterile injectable solutions or dispersions just prior to use. Examples of suitable aqueous and non-aqueous carriers, diluents, solvents or vehicles include water, ethanol, polyols (such as glycerol, propylene glycol, polyethylene glycol, and the like), and suitable mixtures thereof, vegetable oils (such as olive oil), and injectable organic esters such as ethyl oleate. Proper fluidity can be maintained, for example, by the use of coating materials such as lecithin, by the maintenance of the required particle size in the case of dispersions, and by the use of surfactants.

In some embodiments, the pharmaceutical compositions may also contain adjuvants such as preservative, wetting agents, emulsifying agents, and dispersing agents. Prevention of the action of micro-organisms may be ensured by the inclusion of various antibacterial and antifungal agents, for example, paraben, chlorobutanol, phenol sorbic acid, and the like. It may also be desirable to include isotonic agents such as sugars, sodium chloride, and the like. Prolonged absorption of the injectable pharmaceutical form may be brought about by the inclusion of agents that delay absorption such as aluminium monostearate and gelatin. If desired, and for more effective distribution, the compounds can be incorporated into slow release or targeted delivery systems such as polymer matrices, liposomes, and microspheres.

In some embodiments, the pharmaceutical compositions that are injectable formulations can be sterilised, for example, by filtration through a bacterial-retaining filter, or by incorporating sterilizing agents in the form of sterile solid pharmaceutical compositions that can be dissolved or dispersed in sterile water or other sterile injectable medium just prior to use.

In some embodiments, solid dosage forms of the instant pharmaceutical compositions for oral administration. In some embodiments, the oral dosage forms include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid pharmaceutical compositions of a similar type may also be employed as fillers in soft and hard-filled gelatin capsules using such excipients as lactose or milk sugar as well as high molecular weight polyethylene glycols and the like.

The solid dosage forms of the instant pharmaceutical compositions of tablets, dragées, capsules, pills, and granules can be prepared with coatings and shells such as enteric coatings and other coatings well known in the pharmaceutical formulating art. They may optionally contain opacifying agents and can also be of a formulation that they release the active ingredient(s) only, or preferentially, in a certain part of the intestinal tract, optionally, in a delayed manner. Examples of embedding pharmaceutical compositions which can be used include polymeric substances and waxes.

The active compounds can also be in microencapsulated form, if appropriate, with one or more of the above-mentioned excipients.

Some embodiments provide liquid dosage forms of the instant pharmaceutical compositions for oral administration. In some embodiments, the liquid dosages include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral pharmaceutical compositions can also include adjuvants such as wetting agents, emulsifying and suspending agents, sweetening, flavouring, and perfuming agents.

Suspensions of the instant compounds, in addition to the active compounds, may contain suspending agents as, for example, ethoxylated isostearyl alcohols, polyoxyethylene sorbitol and sorbitan esters, microcrystalline cellulose, aluminium metahydroxide, bentonite, agar-agar, and tragacanth, and mixtures thereof.

Pharmaceutical compositions for rectal or vaginal administration are preferably suppositories which can be prepared by mixing the compounds with suitable non-irritating excipients or carriers such as cocoa butter, polyethylene glycol or a suppository wax which are solid at room temperature but liquid at body temperature and therefore melt in the rectum or vaginal cavity and release the active compound.

Dosage forms for topical administration of a compound or pharmaceutical composition of the present disclosure include powders, patches, sprays, ointments and inhalants. The active compound is mixed under sterile conditions with a pharmaceutically acceptable carrier and any needed preservatives, buffers, or propellants which may be required.

Uses

Some embodiments provide methods of treating cancer, comprising administering to a patient in need thereof a therapeutically effective amount of a compound of Formula I, or a pharmaceutically acceptable salt, solvate, solvate of a salt, or a prodrug thereof. In some embodiments the cancers include, but are not limited to: glioblastoma, bone cancer, head and neck cancer, melanoma, basal cell carcinoma, squamous cell carcinoma, adenocarcinoma, oral cancer, esophageal cancer, gastric cancer, intestinal cancer, colon cancer, bladder cancer, hepatocellular carcinoma, renal cell carcinoma, pancreatic cancer, ovarian cancer, cervical cancer, lung cancer, breast cancer, and prostate cancer. In some embodiments, the cancer is glioblastoma. In some embodiments, the cancer is melanoma, basal cell carcinoma, or squamous cell carcinoma. In some embodiments, the cancer is head and neck cancer, oral cancer, or esophageal cancer. In some embodiments, the cancer is bone cancer. In some embodiments, the cancer is adenocarcinoma. In some embodiments, the cancer is gastric cancer, intestinal cancer, colon cancer, or bladder cancer. In some embodiments, the cancer is hepatocellular carcinoma or renal cell carcinoma. In some embodiments, the cancer is pancreatic cancer. In some embodiments, the cancer is lung cancer. In some embodiments, the cancer is non-small cell lung cancer. In some embodiments, the cancer is prostate cancer. In some embodiments, the cancer is ovarian cancer or cervical cancer. In some embodiments, the cancer is breast cancer. In some embodiments, the compound of Formula I, or a pharmaceutically acceptable salt thereof, is a compound of Formulae Ia, Ib, Ic, Id, or a pharmaceutically acceptable salt of any of the foregoing.

Some embodiments provide methods preventing the onset of and/or recurrence of cancer, comprising administering to a patient in need thereof a therapeutically effective amount of a compound of Formula I, or a pharmaceutically acceptable salt, solvate, solvate of a salt, or a prodrug thereof.

Some embodiments provide methods of treating cancer, comprising administering to a patient in need thereof a therapeutically effective amount of a composition comprising a compound of Formula I, or a pharmaceutically acceptable salt, solvate, solvate of a salt, or a prodrug thereof. In some embodiments the cancers include, but are not limited to: glioblastoma, bone cancer, head and neck cancer, melanoma, basal cell carcinoma, squamous cell carcinoma, adenocarcinoma, oral cancer, esophageal cancer, gastric cancer, intestinal cancer, colon cancer, bladder cancer, hepatocellular carcinoma, renal cell carcinoma, pancreatic cancer, ovarian cancer, cervical cancer, lung cancer, breast cancer, and prostate cancer. In some embodiments, the cancer is glioblastoma. In some embodiments, the cancer is melanoma, basal cell carcinoma, or squamous cell carcinoma. In some embodiments, the cancer is head and neck cancer, oral cancer, or esophageal cancer. In some embodiments, the cancer is bone cancer. In some embodiments, the cancer is adenocarcinoma. In some embodiments, the cancer is gastric cancer, intestinal cancer, colon cancer, or bladder cancer. In some embodiments, the cancer is hepatocellular carcinoma or renal cell carcinoma. In some embodiments, the cancer is pancreatic cancer. In some embodiments, the cancer is lung cancer. In some embodiments, the cancer is non-small cell lung cancer. In some embodiments, the cancer is prostate cancer. In some embodiments, the cancer is ovarian cancer or cervical cancer. In some embodiments, the cancer is breast cancer. In some embodiments, the compound of Formula I, or a pharmaceutically acceptable salt thereof, is a compound of Formulae Ia, Ib, Ic, Id, or a pharmaceutically acceptable salt of any of the foregoing.

Some embodiments provide methods preventing the onset of and/or recurrence of cancer, comprising administering to a patient in need thereof a therapeutically effective amount of a compound of Formula I, or a pharmaceutically acceptable salt, solvate, solvate of a salt, or a prodrug thereof.

Some embodiments provide a compound of Formula I for use in treating cancer. In some embodiments the cancers include, but are not limited to: glioblastoma, bone cancer, head and neck cancer, melanoma, basal cell carcinoma, squamous cell carcinoma, adenocarcinoma, oral cancer, esophageal cancer, gastric cancer, intestinal cancer, colon cancer, bladder cancer, hepatocellular carcinoma, renal cell carcinoma, pancreatic cancer, ovarian cancer, cervical cancer, lung cancer, breast cancer, and prostate cancer. In some embodiments, the cancer is glioblastoma. In some embodiments, the cancer is melanoma, basal cell carcinoma, or squamous cell carcinoma. In some embodiments, the cancer is head and neck cancer, oral cancer, or esophageal cancer. In some embodiments, the cancer is bone cancer. In some embodiments, the cancer is adenocarcinoma. In some embodiments, the cancer is gastric cancer, intestinal cancer, colon cancer, or bladder cancer. In some embodiments, the cancer is hepatocellular carcinoma or renal cell carcinoma. In some embodiments, the cancer is pancreatic cancer. In some embodiments, the cancer is lung cancer. In some embodiments, the cancer is non-small cell lung cancer. In some embodiments, the cancer is prostate cancer. In some embodiments, the cancer is ovarian cancer or cervical cancer. In some embodiments, the cancer is breast cancer.

Some embodiments provide a compound of Formula I for use in preventing the onset of and/or recurrence of cancer.

Some embodiments provide a compound of Formula I for the preparation of a medicament for treating cancer. In some embodiments the cancers include, but are not limited to: glioblastoma, bone cancer, head and neck cancer, melanoma, basal cell carcinoma, squamous cell carcinoma, adenocarcinoma, oral cancer, esophageal cancer, gastric cancer, intestinal cancer, colon cancer, bladder cancer, hepatocellular carcinoma, renal cell carcinoma, pancreatic cancer, ovarian cancer, cervical cancer, lung cancer, breast cancer, and prostate cancer. In some embodiments, the cancer is glioblastoma. In some embodiments, the cancer is melanoma, basal cell carcinoma, or squamous cell carcinoma. In some embodiments, the cancer is head and neck cancer, oral cancer, or esophageal cancer. In some embodiments, the cancer is bone cancer. In some embodiments, the cancer is adenocarcinoma. In some embodiments, the cancer is gastric cancer, intestinal cancer, colon cancer, or bladder cancer. In some embodiments, the cancer is hepatocellular carcinoma or renal cell carcinoma. In some embodiments, the cancer is pancreatic cancer. In some embodiments, the cancer is lung cancer. In some embodiments, the cancer is non-small cell lung cancer. In some embodiments, the cancer is prostate cancer. In some embodiments, the cancer is ovarian cancer or cervical cancer. In some embodiments, the cancer is breast cancer.

Some embodiments provide a compound of Formula I for the preparation of a medicament for use in preventing the onset of and/or recurrence of cancer.

Administration

The compounds and compositions described herein can, for example, be administered orally, parenterally (e.g., subcutaneously, intracutaneously, intravenously, intramuscularly, intraarticularly, intraarterially, intrasynovially, intrasternally, intrathecally, intralesionally and by intracranial injection or infusion techniques), by inhalation spray, topically, rectally, nasally, buccally, vaginally, via an implanted reservoir, by injection, subdermally, intraperitoneally, transmucosally, or in an ophthalmic preparation, with a dosage ranging from about 0.01 mg/kg to about 1000 mg/kg, or any value in between (e.g., from about 0.01 to about 100 mg/kg, from about 0.1 to about 100 mg/kg, from about 1 to about 100 mg/kg, from about 1 to about 10 mg/kg, or any value in between) every 4 to 120 hours, or any value in between. The interrelationship of dosages for animals and humans (based on milligrams per meter squared of body surface) is described by Freireich et al., Cancer Chemother. Rep. 50, 219-244 (1966) and is understood by those skilled in the art. Body surface area may be approximately determined from height and weight of the patient by those skilled in the art. See, e.g., Scientific Tables, Geigy Pharmaceuticals, Ardsley, N.Y., 537 (1970). In certain embodiments, the compositions are administered by oral administration or by injection. The methods herein contemplate administration of an effective amount of compound or compound composition to achieve the desired or stated effect. Typically, the pharmaceutical compositions of the present disclosure will be administered from about 1 to about 6 times per day or alternatively, as a continuous infusion. Such administration can be used as a chronic or acute therapy.

Lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the disease, condition or symptoms, the patient's disposition to the disease, and the judgment of the treating physician.

In some embodiments, dosage forms include from about 0.001 milligrams to about 2,000 milligrams, or any value in between (including, from about 0.001 milligrams to about 1,000 milligrams, from about 0.001 milligrams to about 500 milligrams, from about 0.01 milligrams to about 250 milligrams, from about 0.01 milligrams to about 100 milligrams, from about 0.05 milligrams to about 50 milligrams, and from about 0.1 milligrams to about 25 milligrams, or any value in between) of a compound of Formula I (and/or a compound of any of the other formulae described herein) or a salt (e.g., a pharmaceutically acceptable salt) thereof as defined anywhere herein. The dosage forms can further include a pharmaceutically acceptable carrier and/or an additional therapeutic agent.

Appropriate dosage levels may be determined by any suitable method known to one skilled in the art of treating cancer. Preferably, the active substance is administered at a frequency of 1 to 4 times per day for topical administration, or less often if a drug delivery system is used.

Nevertheless, actual dosage levels and time course of administration of the active ingredients in the pharmaceutical compositions of the present disclosure may be varied so as to obtain an amount of the active ingredient which is effective to achieve the desired therapeutic response for a particular patient, composition and mode of administration, without being toxic to the patient. It may therefore be necessary where appropriate to deviate from the stated amounts, in particular as a function of age, gender, body weight, diet and general health status of the patient, route of administration, individual response to the active ingredient, nature of the preparation, and time or interval over which administration takes place. Thus, it may be satisfactory in some cases to manage with less than the aforementioned minimum amount, whereas in other cases the stated upper limit must be exceeded. It may in the event of administration of larger amounts be advisable to divide these into multiple individual doses spread over the day.

In some embodiments, the compounds of the present disclosure may be co-administered with one or more additional agents used in the treatment of cancer. In some embodiments, the additional agents include, but are not limited to: alkylating agents such as cyclophosphamide, chlorambucil, meclorethamine, ifosfamide, or melphalan; antimetabolites such as methotrexate, cytarabine, gemcitabine, fludarabine, 6-mercaptopurine, azathioprene, or 5-fluorouracil; antimitotic agents such as vincristine, vinblastine, vindesine, vinorelbine, paclitaxel, or docetaxel; platinum derivatives such as cisplatin, carboplatin or oxaliplatin; hormone therapeutics such as tamoxifen; aromatase inhibitors such as bicalutamide, anastrozole, exemestane or letrozole; signaling inhibitors such as imatinib (tyrosine kinase inhibitor; Gleevac), gefitinib (EGFR inhibitor; Iressa) or erlotinib (receptor TKI, which acts on EGFR; Tarceva); monoclonal antibodies such as trastuzumab, pertuzumab, inotuzumab, or ozogamicins thereof, as well as other antibody-drug conjugates such as ado-trastuzumab emtansine; antiangiogenic agents such as bevacizumab, sorafenib (tyrosine protein kinase), pazopanib or sunitinib (receptor tyrosine kinase inhibitor); tivozanib, axitinib, and cediranib; -tinib (tyrosine kinase inhibitors) such as lapatinib; biologic response modifiers such as interferon-alpha; topoisomerase inhibitors such as camptothecins (including irinotecan and topotecan), amsacrine, etoposide, etoposide phosphate, or teniposide; anthracyclines such as doxorubicin, daunorubicin, epirubicin, idarubicin, sabarubicin, aclarubicin, carubicin and valrubicin; other cytotoxic agents such as actinomycin, bleomycin, plicamycin or mitomycin; mTOR inhibitors such as rapamycin, temsirolimus and everolimus; and antibody therapy such as CTLA4 antibody therapy, PDL1 antibody therapy, and PD1 antibody therapy.

The terms "CTLA4 antibody" and "anti-CTLA4" refer to an antibody or antibodies directed towards cytotoxic t-lymphocyte antigen 4 (CTLA4). Exemplary antibodies include, but are not limited to, antibodies that are CTLA4 antagonists or the CTLA4 antibodies as set forth in U.S. Pat. Nos. 8,685,394 and 8,709,417. Some embodiments of the antibody include ipilimumab (YERVOY®, Bristol-Myers Squibb) and CP-675,206 (tremelimumab, Pfizer). In a particular embodiment, the antibody is ipilimumab.

"PDL1 antibody" or "anti-PDL1" refers to an antibody directed towards programmed death ligand 1 (PDL1). Exemplary antibodies include, but are not limited to, the antibodies set forth in U.S. Pat. Nos. 8,217,149, 8,383,796, 8,552,154 and 8,617,546. Some embodiments of the antibody include avelumab (Merck KGA/Pfizer), durvalumab (AstraZeneca) and atezolizumab (TECENTRIQ®, Roche). In a particular embodiment, the antibody is atezolizumab.

The terms "PD1 antibody" and "anti-PD1" refers to an antibody directed towards programmed death protein 1 (PD1). Exemplary antibodies include, but are not limited to, the antibodies set forth in U.S. Pat. Nos. 7,029,674, 7,488, 802, 7,521,051, 8,008,449, 8,354,509, 8,617,546 and 8,709, 417. Particular embodiments of the antibody include BGB-A317, nivolumab (OPDIVO®, Bristol-Myers Squibb), labrolizumab (Merck), and pembrolizumab (KEYTRUDA®, Merck).

In some embodiments, the antibody, e.g., anti-CTLA4, anti-PDL1 or anti-PD1, will be mixed, prior to administration, with a non-toxic, pharmaceutically acceptable carrier substance (e.g., normal saline or phosphate-buffered saline), and may be administered using any medically appropriate procedure, for example, including but not limited to, intravenous or intra-arterial administration, and injection into the cerebrospinal fluid. In certain cases, intraperitoneal intradermal, intracavity, intrathecal or direct administration to a tumor or to an artery supplying the tumor may be advantageous.

The terms "antibody" and "antibodies" as used herein is inclusive of all types of immunoglobulins, including IgG, IgM, IgA, IgD, and IgE, or fragments thereof, that may be appropriate for the medical uses disclosed herein. The antibodies may be monoclonal or polyclonal and may be of any species of origin, including, for example, mouse, rat, rabbit, horse, or human. Antibody fragments that retain specific binding to the protein or epitope, for example, CTLA4, PDL1 or PD1, bound by the antibody used in the present disclosure are included within the scope of the term "antibody." Such fragments can be produced by known techniques. The antibodies may be chimeric or humanized, particularly when they are used for therapeutic purposes. The antibody may be obtained or prepared using methods known in the art.

In some embodiments, other immunotherapy targets such as IDO inhibitors, e.g., epacadostat may also be used in combination with compounds of the present disclosure.

In some embodiments, the additional agents may be administered separately from the compounds of the present disclosure as part of a multiple dose regimen (e.g., sequentially, or on different overlapping schedules with the administration of one or more compounds of Formula I). In other embodiments, these agents may be part of a single dosage form, mixed together with the compounds of the present disclosure in a single composition. In some embodiments, these agents can be given as a separate dose that is administered at about the same time as one or more compounds of Formula I are administered (e.g., simultaneously with the administration of one or more compounds of Formula (I) (and/or a compound of any of the other formulae, including any subgenera or specific compounds thereof)). In some embodiments, at least one of the therapeutic agents in the combination therapy is administered using the same dosage regimen (dose, frequency and duration of treatment) that is typically employed when the agent is used as monotherapy for treating the same cancer. In some embodiments, the patient receives a lower total amount of at least one of the therapeutic agents in the combination therapy than when the agent is used as monotherapy, e.g., smaller doses, less frequent doses, and/or shorter treatment duration.

When the compositions of the present disclosure include a combination of a compound of the formulae described herein and one or more additional agents, both the compound and the additional agent can be present at dosage levels of between about 1 to 100%, and more preferably between about 5 to 95% of the dosage normally administered in a monotherapy regimen.

Biological Function

The utility of the present disclosure can be demonstrated by one or more of the following methods or other methods known in the art:

In Vitro Assay

The compounds in the present disclosure were tested in a functional calcium flux assay using stably transfected HEK293 cells. Cells transfected with EP1, EP2, EP3 and EP4 were purchased from Eurofins Discovery Services (St. Charles, Mo.). Each receptor subtype has an additional promiscuous G protein added in order to couple to the calcium signaling pathway. The parental cell line used also expresses a novel variant of clytin, a calcium-activated photo-protein, to enable sensitive luminescent detection.

Cells were plated at 50,000 cells per well in black, clear bottom 96-well plates. The plated cells were allowed to sit at room temperature for 30 min prior to transferring to a humidified, 37° C., 5% $CO_2$ incubator for 18-24 h. Assay buffer (HBSS with 20 mM HEPES) and loading buffer (assay buffer plus 10 µM Coelenterazine) were prepared on the day of the assay. Assays were performed by aspirating media from the assay plate and washing once with assay buffer, then replacing with loading buffer and allowing the cells to incubate for 1.5 h at room temperature. Compounds were prepared in assay buffer at a 3× final concentration in non-binding plates. Compounds were added to the cell plates and incubated for 30 min at room temperature. The prostanoid receptor ligand PGE2 was prepared at a 4× dilution ratio for a final concentration of 10 nM. Plates were run on a Flexstation™ using a 100 ms integration luminescence protocol for a total of 60 sec with ligand addition at 15 sec. Data were obtained from relative light units as measured by area under the curve.

TABLE 1

| Example | MS (ESI+) | MS (ESI−) | $EP_4$ $Ca^{2+}$-flux assay $IC_{50}$ (nM) |
|---|---|---|---|
| 1 | 400 | 398 | 13 |
| 2 | 443 | 441 | 1.5 |
| 3 | 444 | 442 | 160 |
| 5 | 444 | 442 | 930 |
| 6 | 444 | 442 | 19 |
| 7 | 445 | 443 | 2.0 |
| 8, first eluting | 457 | 455 | 520 |
| 8, second eluting | 457 | 455 | 0.19 |
| 9 | 458 | 456 | 6.0 |
| 10, first eluting | 458 | 456 | 20 |
| 10, second eluting | 458 | 456 | 0.13 |
| 11 | 458 | 456 | 24 |
| 12 | 458 | 456 | 2.7 |
| 13 | 458 | 456 | 32 |
| 14 | 459 | 457 | 9.0 |
| 15 | 459 | 457 | 400 |
| 16 | 582 | 580 | 140 |
| 17 | 597 | 595 | 130 |
| 18 | 467 | 465 | 1.5 |
| 19 | 457 | 455 | 9.1 |
| 20, first eluting | 475 | 473 | 24 |
| 20, second eluting | 475 | 473 | 0.31 |
| 21 | 475 | 473 | 0.31 |
| 23 | 475 | 473 | 0.3 |
| 24 | 414 | 412 | 10 |
| 25 | 439 | 437 | 0.4 |
| 26 | 439 | 437 | 3.8 |
| 27 | 461 | 459 | 0.5 |
| 28 | 475 | 473 | 0.6 |
| 29 | 515 | 513 | 1.2 |
| 30 | 515 | 513 | 0.2 |
| 31 | 457 | 455 | 0.03 |
| 32 | 443 | 441 | 0.1 |
| 33 | 461 | 459 | 0.1 |
| 34 | 451 | 449 | 0.22 |
| 35 | 469 | 467 | 0.28 |
| 36 | 452 | 450 | 0.32 |
| 37 | 460 | 458 | 75 |
| 38 | 519 | 517 | — |
| 39 | 470 | 468 | — |
| 40 | 478 | 476 | — |

In Vivo Tumor Model

Figure 1B:
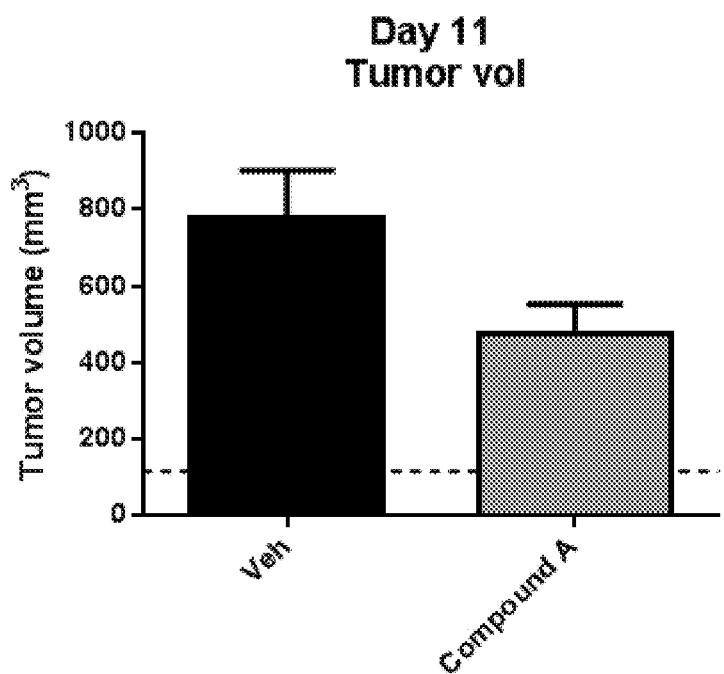

Female Balb/C mice were implanted with $1 \times 10^6$ CT26 colon cancer cells (ATCC® CRL-2638™) in a $2 \times 10^6$ cells/mL++PBS solution. Cells were injected subcutaneously into the left hind flank. Tumors were measured with calipers and tumor volumes calculated using the formula: tumor volume=(length×width$^2$)/2. When tumor volumes were ~150 mm$^3$, mice were randomized into groups (10 animals per group) and treated with either vehicle (0.5% methocel PO, bid for 11 days) or test compound (30 mg/kg PO, bid for 11 days). Tumor volumes were determined 3 times a week until study termination. Results for compound A are provided in FIGS. 1A and 1B.

Preparation of Compounds

The starting materials used for the synthesis are either synthesized or obtained from commercial sources, such as, but not limited to, Sigma-Aldrich, Fluka, Acros Organics, Alfa Aesar, Enamine, PharmaBlock, VWR Scientific, and the like. The reversed phase and normal phase chromatography columns were purchased from Teledyne ISCO, Inc. (NE). Nuclear Magnetic Resonance (NMR) analysis was conducted using a Bruker Fourier 300 MHz spectrometer with an appropriate deuterated solvent. LCMS spectra were obtained on a Shimazu LCMS-2020 Series mass spectrometer using Electrospray Ionization (ESI) and a Luna C18 5 μM, 2.0×50 mm column, eluting with 95:5 to 0:100 H2O: MeCN+0.1% formic acid at a flow rate of 0.7 mL/min over 3.5 minutes. General methods for the preparation of compounds can be modified by the use of appropriate reagents and conditions for the introduction of the various moieties found in the structures as provided herein.

Abbreviations

| Aq. | Aqueous |
|---|---|
| BrettPhos | 2-(dicyclohexylphosphino)3,6-dimethoxy-2',4',6'-trIisopropyl-1,1'-biphenyl |
| CDI | Carbonyldiimidazole |
| DABCO | 1,4-diazabicyclo[2.2.2]octane |
| DCC | N,N'-dicyclohexylcarbodiimide |
| DMAP | 4-dimethylaminopyridine |
| DMF | Dimethylformamide |
| e.e. | Enantiomeric excess |
| EDCI | 1-Ethyl-3-(3-dimethylaminopropyl)carbodiimide |
| Eq. | Equivalent(s) |
| EtOAc | Ethyl acetate |
| h | Hour(s) |
| HATU | 1-[Bis(dimethylamino)methylene]-1H-1,2,3-triazolo[4,5-b]pyridinium 3-oxide hexafluorophosphate |
| Hex | Hexanes |
| LC-MS | Liquid chromatography/mass spectrometry (Shimazu, Model#: LCMS-2020) |
| M | Molar |
| MeCN | Acetonitrile |
| Me-THF | 2-methyltetrahydrofuran |
| min | Minute(s) |
| N | Normal |
| NMP | N-methyl-2-pyrrolidone |
| O/N | Overnight |
| ++PBS | Phosphate buffered saline with added calcium(II) and magnesium(II) |
| PMHS | polymethylhydrosiloxane |
| RBF | Round bottom flask |
| RT | Room temperature |
| RuPhos | 2-dicyclohexylphosphino-2',6'-diisopropoxybiphenyl |
| SFC | Supercritical fluid chromatography |
| T3P | Propylphosphonic anhydride |
| TFA | Trifluoracetic acid |
| THF | Tetrahydrofuran |
| TMSI | Trimethylsilyl iodide |
| v | volume |
| XPhos | 2-dicyclohexylphosphino-2',4',6'-tri-iso-propylbiphenyl |

General Synthetic Scheme

Compounds of formula I of the present disclosure may be prepared, for example, from an amine (1), or its corresponding ammonium salt, and a carboxylic acid (2) in the presence of an appropriate coupling reagent such as HATU, CDI, or the like, and an appropriate base such as triethylamine, ethyl-diisopropyl-amine, or the like. Alternatively, the acid may be pre-activated via its conversion into the corresponding acid chloride using an agent such as thionyl chloride, oxalyl chloride, or the like. The resulting amide 3 is converted into the targeted compound I using synthetic methodologies appropriate for the identity of the functional group "G" in 3 and the desired identity of the functional group "W" in I. Examples of such conversions include, but are not limited to:

(a) ester hydrolysis (i.e. "G"=CO$_2$R, where R can be methyl, ethyl, benzyl, tert-butyl, or the like; and "W"=CO$_2$H) using well-known conditions such as acid-mediated hydrolysis (i.e. HCl, TFA, H$_2$SO$_4$, or the like), base-mediated hydrolysis (i.e. NaOH, LiOH, Bu$_4$NOH, or the like), nucleophile-mediated hydrolysis (i.e. LiI, TMSI, Me$_3$SnOH or the like), enzyme-mediated hydrolysis (pig liver esterase, *Candida antarctica* lipase, *Candida rugosa* lipase, or the like), metal-mediated hydrogenolysis (Pd/C and H$_2$, Pd(PPh$_3$)$_4$ and PMHS, or the like), and others.

Alternatively, the aforementioned ester group can first be derivatized (i.e. mono- or bis-alkylation or arylation at the α-carbon via the corresponding enolate, if accessible, or the like) prior to hydrolysis.

(b) reaction of nitrile (i.e. "G"=CN)—

(i) to form a tetrazole

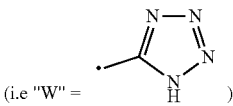

by heating 3 with an appropriate azide source (i.e. NaN$_3$, Bu$_3$SnN$_3$, Bu$_4$NN$_3$, or the like), most often in the presence of an appropriate promoter (i.e. ZnBr$_2$, Bu$_2$Sn=O, NH$_4$Cl, or the like);

(ii) to form an oxadiazalone

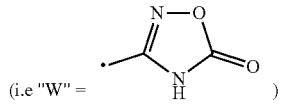

by heating 3 with hydroxylamine and then treating the resulting N-hydroxyamidine with CDI, or the like; and (iii) to form a carboxylic acid (i.e. "W"=CO$_2$H) by heating 3 with aqueous KOH and ethylene glycol, or the like.

(c) elaboration of carboxylic acid (i.e. "G"=CO$_2$H)—

(i) using Arndt-Eistert homologation or the like, in cases where Y is a bond, to provide the corresponding compound where Y is CH$_2$;

(ii) into an acyl sulfonamide by coupling 3 with a sulfonamide in the presence of a coupling agent such as DCC, or the like;

(iii) into a hydroxamic acid by coupling 3 with hydroxylamine in the presence of a coupling agent such as T$_3$P, or the like.

Scheme 1

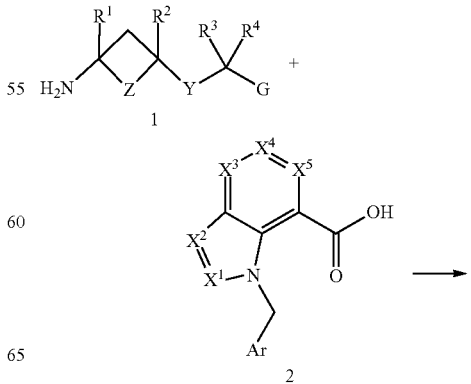

-continued

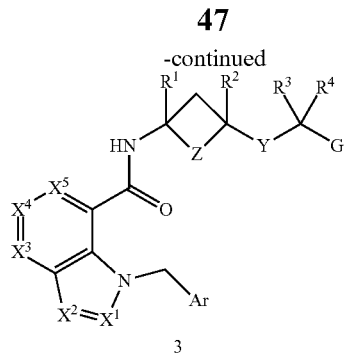

3

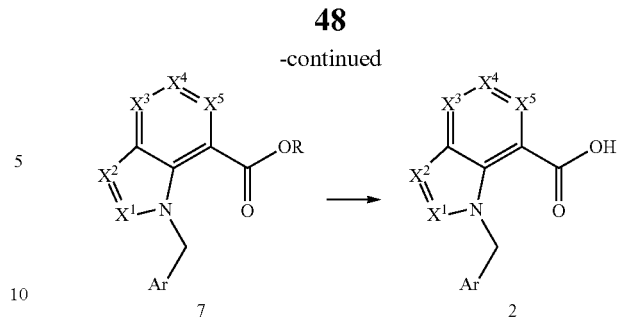

Compound 6 is commercially available, or it may be conveniently prepared from the ester 8 by, for example, the initial reduction of 8 using reagents such as DIBAL-H, LiBH$_4$, LiAlH$_4$, or the like (Scheme 3) to the corresponding alcohol 9. Treatment of alcohol 9 with mesyl chloride, tosyl anhydride, PBr$_3$, or the like, in the presence of an appropriate base such as NEt$_3$, pyridine, DABCO, or the like provides the corresponding compound 6. Furthermore, reduction of 8 using deuterated reducing agents such as LiAlD$_4$ allows access to analogues containing stable deuterium isotopes at the benzylic carbon of 9.

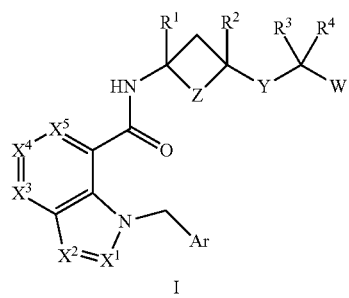

I

Carboxylic acid 2 used for the coupling described in Scheme 1 may be prepared from ester 5 via its initial N-alkylation by an Ar—CH$_2$-LG (i.e. 6) wherein LG is a leaving group such as halide, mesylate, tosylate, or the like, in the presence of an appropriate base (i.e. NaH, Cs$_2$CO$_3$, KOtBu, or the like). Subsequent hydrolysis of ester 7 using procedures known to those skilled in the art including those described above provides the carboxylic acid 2.

Scheme 3

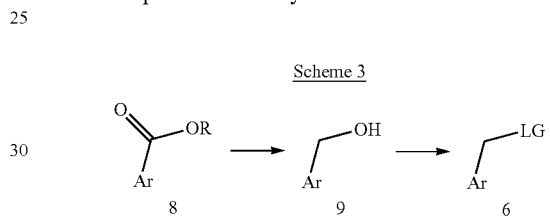

Alternatively, the ester intermediate 7 can be accessed via an initial arylation of amine 10 with ester 11 to provide the aniline ester 12, followed by a suitable annulation sequence (Scheme 4). Arylation of 10 can be realized via direct S$_N$Ar displacement of an appropriately functionalized aryl fluoride (i.e. 11 where Hal=F) or via metal-catalyzed coupling of an appropriately functionalized aryl iodide (i.e. 11 where Hal=I). Annulation sequence can entail metal-catalyzed heterocyclization of the aniline nitrogen on ester 12 onto a pendant alkyne (i.e. 12 where FG=alkyne) to deliver the fused biaryl ester 7a, or acid-promoted condensation of intermediate ester 12 with formic acid, or the like, in the presence of a reducing metal (i.e. 12 where FG=NO$_2$) to deliver the fused biaryl ester 7b.

Scheme 2

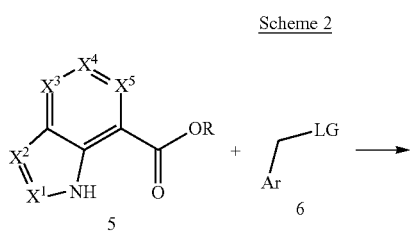

Scheme 4

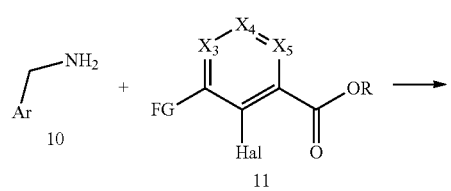

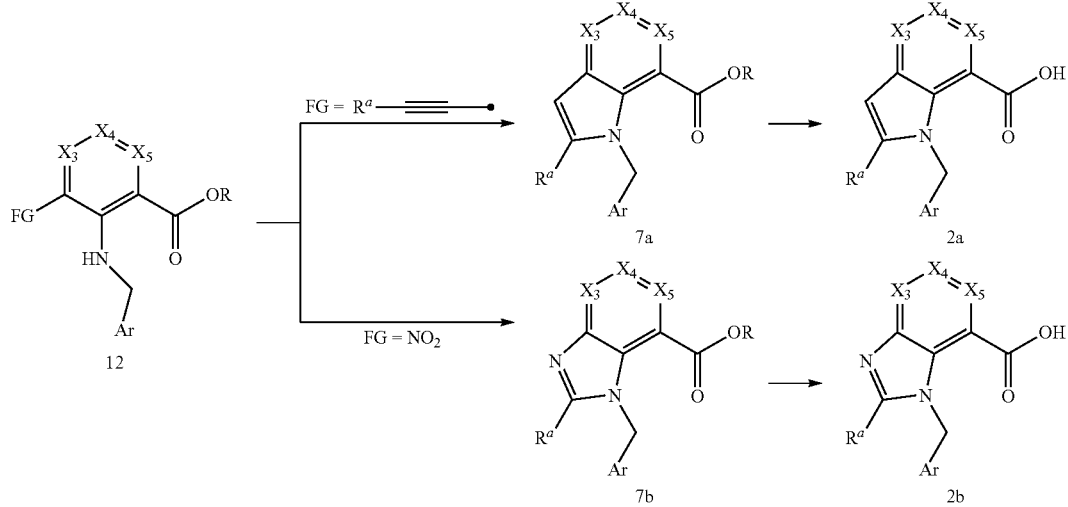

Amine 1 used for the coupling described in Scheme 1 may be prepared from carboxylic acid 13 (Scheme 5) via Curtius rearrangement (i.e. by way of an acyl azide: 14 where FG=N₃), Hoffmann rearrangement (i.e. by way of a primary amide: 14 where FG=NH₂), Lossen rearrangement (i.e. by way of a hydroxamic acid: 14 where FG=NHOH), or the like. The preparation of the precursors for the rearrangement reactions (i.e. 14), as well as reagents and conditions for the rearrangement reactions, are well known to those skilled in the art, and are described in standard textbooks such as March's Advanced Organic Chemistry, 7$^{th}$ Ed., John Wiley & Sons, 2013. The resulting product, carbamate 15, can be directly de-protected to reveal the requisite amine 1 using conditions known to those skilled in the art (i.e. by treatment with HCl, TFA, or the like when R is tert-butyl; or by hydrogenation in the presence of catalysts such as Pd/C, Pt/C, or the like when R is benzyl). Alternatively, the removal of the carbamate protecting group can be postponed until after all the desired chemical manipulations of functional group(s) distal to the nitrogen have been completed.

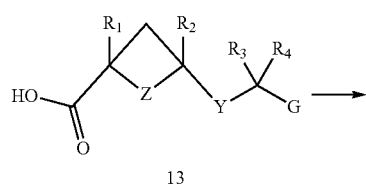

13

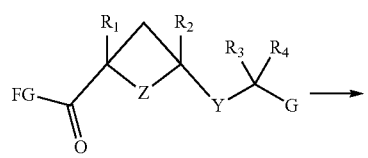

14

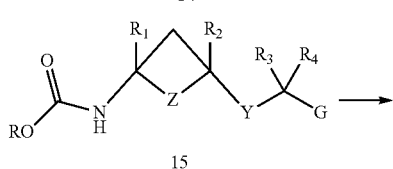

15

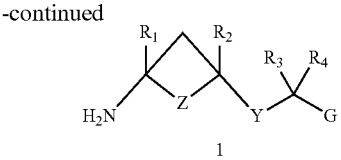

1

In instances where Ar of amide 16 (Scheme 6) is substituted with a halogen such as Br or I, it may be deemed desirable to effect its transformation into, for example, (hetero)aryl amide 17 or heterocyclic amide 18. Such functional group conversion can be readily realized using metal-catalyzed reactions known to those skilled in the art. Examples of such conversions can include, but are not limited to: (a) Suzuki reaction using (hetero)aryl boronic acid or (hetero)aryl boronate ester as the coupling partner, XPhos palladocycle, Pd(dppf)Cl₂ or any other suitable palladium ligand complexes as the catalyst, and aqueous potassium phosphate, sodium carbonate, or the like as the base; (b) Buchwald-Hartwig reaction using primary or secondary amine as the coupling partner, RuPhos palladocycle, BrettPhos palladocycle or any other suitable palladium ligand complexes as the catalyst, and sodium tert-pentoxide, potassium tert-butoxide or the like as the base.

SCHEME 6

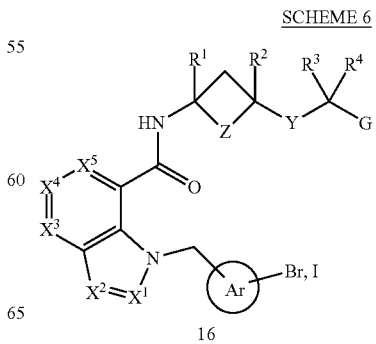

16

-continued

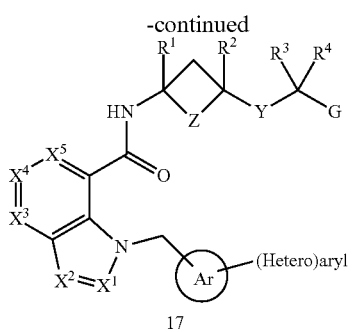

17 or

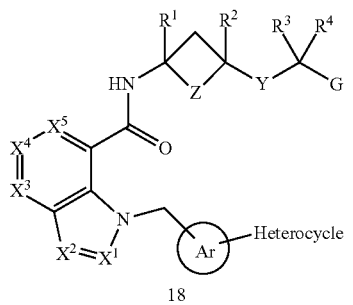

18

Preparation of Intermediates

Intermediate acid 1:
1-(4-cyanobenzyl)-1H-indole-7-carboxylic Acid

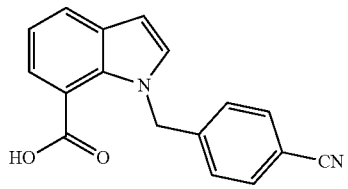 [SMILES: N#Cc1ccc(Cn2ccc3cccc(C(=O)O)c32)cc1]

To a solution of methyl 1H-indole-7-carboxylate (1 eq.) in DMF (0.29 M) cooled to 0° C. was added potassium tert-butoxide (1.2 eq.) such that the reaction temperature does not exceed 5° C. The resulting suspension was stirred at 0° C. for 30 min and then at RT for 30 min. The solution was re-cooled to 0° C. and 4-(bromomethyl)benzonitrile (1.2 eq.) in DMF (0.69M) was added dropwise. The reaction mixture was allowed to warm slowly to RT over 16 h and then quenched with the addition of ice-water and extracted with EtOAc. The combined organic extracts were washed further with water, 10% aq. NaHCO$_3$ and brine, dried over MgSO$_4$, and filtered. Concentration of the filtrate in vacuo furnished the crude reaction product as a yellow viscous oil, which was purified by column chromatography (SiO$_2$, gradient elution, 9:1 Hexane/EtOAc to EtOAc) to afford the product as a colorless oil that solidified upon standing (75% yield).

1-(4-cyanobenzyl)-1H-indole-7-carboxylic acid (1 eq.) was dissolved in a 2:1 (v/v) solution (0.1 M) of THF and methanol. LiOH (5 eq., 2 N aq. solution) was added and the solution was heated at 50° C. for 3 h. The reaction mixture was cooled to RT and then neutralized with HCl (5 eq., 1 N aq. solution). The suspension was extracted with EtOAc. The combined organic extracts were washed further with water and brine, dried over MgSO$_4$, and filtered. Concentration of the filtrate in vacuo furnished the crude reaction product as a yellow viscous oil that solidified upon standing. Trituration in toluene afforded the product as a white, crystalline solid (67% yield).

Intermediate acid 2: 1-(4-(trifluoromethyl)benzyl)-1H-indole-7-carboxylic Acid

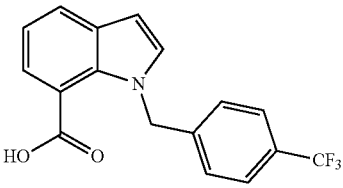

Prepared in an analogous fashion to Intermediate acid 1, but using 1-(bromomethyl)-4-(trifluoromethyl)benzene (1.2 eq.) in place of 4-(bromomethyl)benzonitrile.

Intermediate acid 3: 1-(4-(trifluoromethyl)benzyl)-1H-pyrrolo[3,2-b]pyridine-7-carboxylic Acid

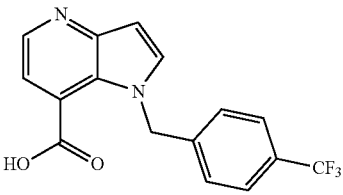 [SMILES: O=C(O)c1ccnc2ccn(Cc3ccc(C(F)(F)F)cc3)c12]

Prepared in an analogous fashion to Intermediate acid 1, but using methyl 1H-pyrrolo[3,2-b]pyridine-7-carboxylate (1 eq.) in place of methyl 1H-indole-7-carboxylate; and 1-(bromomethyl)-4-(trifluoromethyl)benzene (1.2 eq.) in place of 4-(bromomethyl)benzonitrile.

Intermediate acid 4: 1-(4-(trifluoromethyl)benzyl)-1H-pyrrolo[3,2-c]pyridine-7-carboxylic Acid

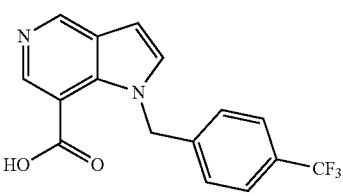 [SMILES: O=C(O)c1cncc2ccn(Cc3ccc(C(F)(F)F)cc3)c12]

Prepared in an analogous fashion to Intermediate acid 1, but using methyl 1H-pyrrolo[3,2-c]pyridine-7-carboxylate (1 eq.) in place of methyl 1H-indole-7-carboxylate; and 1-(bromomethyl)-4-(trifluoromethyl)benzene (1.2 eq.) in place of 4-(bromomethyl)benzonitrile.

Intermediate acid 5: 1-(4-(trifluoromethyl)benzyl)-1H-pyrrolo[2,3-c]pyridine-7-carboxylic Acid

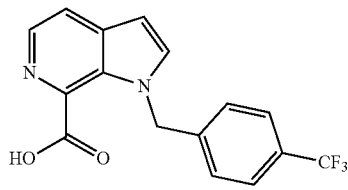 [SMILES: O=C(O)c1nccc2ccn(Cc3ccc(C(F)(F)F)cc3)c12]

Prepared in an analogous fashion to Intermediate acid 1, but using methyl 1H-pyrrolo[2,3-c]pyridine-7-carboxylate (1 eq.) in place of methyl 1H-indole-7-carboxylate; and 1-(bromomethyl)-4-(trifluoromethyl)benzene (1.2 eq.) in place of 4-(bromomethyl)benzonitrile.

Intermediate acid 6: 1-(4-(trifluoromethyl)benzyl)-1H-indazole-7-carboxylic Acid

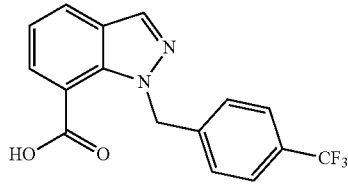 [SMILES: O=C(O)c1cccc2cnn(Cc3ccc(C(F)(F)F)cc3)c12]

A suspension of methyl 1H-indazole-7-carboxylate (1 eq.) and cesium carbonate (3 eq.) in DMF (0.74 M) was cooled to 0° C. and 1-(bromomethyl)-4-(trifluoromethyl)benzene (1.2 eq., 0.89M in DMF) was added dropwise. The reaction mixture was allowed to warm slowly to rt over 16 h and then quenched with ice-water and extracted with TBME. The combined organic extracts were washed further with water and brine, dried over $MgSO_4$, and filtered. Concentration of the filtrate in vacuo furnished the crude reaction product as a golden yellow oil, which was purified with column chromatography ($SiO_2$, 9:1 (v/v) Hex:EtOAc to EtOAc) to afford the product as a colorless oil (76% yield).

The product from the previous step (1 eq.) was dissolved in a 3:2 (v/v) solution (0.11 M) of THF and methanol and LiOH (3 eq., 2 N aq. solution) was added. The resulting solution was stirred at RT for 16 h and neutralized with HCl (3 eq., 1 N aq. solution). The resulting suspension was extracted with EtOAc and the combined organic extracts were washed further with water and brine, dried over $MgSO_4$, and filtered. Concentration of the filtrate in vacuo furnished the crude reaction product as a viscous oil. Recrystallization from TBME and hexanes afforded the product as a white, crystalline solid (60% yield).

Intermediate acid 7: 1-(4-(trifluoromethyl)benzyl)-1H-benzo[d]imidazole-7-carboxylic Acid

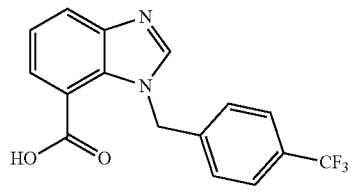 [SMILES: O=C(O)c1cccc2ncn(Cc3ccc(C(F)(F)F)cc3)c12]

Methyl 2-fluoro-3-nitrobenzoate (1 eq.), (4-(trifluoromethyl)phenyl) methanamine (1.5 eq.) and potassium carbonate (2 eq.) were combined in DMF (0.24 M) and the suspension was heated at 80° C. for 2 h. The reaction was cooled to rt, diluted with EtOAc and washed sequentially with 10% aq. $NH_4Cl$, water and brine. The organic layer was then dried over $MgSO_4$ and filtered. Concentration of the filtrate in vacuo furnished the crude reaction product as a yellow semi-solid. Purification by column chromatography ($SiO_2$, 9:1 (v/v) Hex:EtOAc to 3:7 (v/v) Hex:EtOAc) afforded methyl 3-nitro-2-((4-(trifluoromethyl)benzyl)amino)benzoate as a golden, yellow oil (56% yield).

Methyl 3-nitro-2-((4-(trifluoromethyl)benzyl)amino)benzoate (1 eq.), iron powder (10 eq.) and ammonium chloride (10 eq.) were dissolved in a 1:1 (v/v) solution (0.05 M) of 2-propanol and formic acid. The vessel was tightly sealed and heated at 80° C. for 3 h. The suspension was cooled to rt, diluted with 2-propanol and filtered through celite. The filtrate was concentrated in vacuo and the resulting residue was taken up in DCM. The solution was then washed sequentially with 1 N aq. NaOH, water and brine, dried over $MgSO_4$, and filtered. Concentration of the filtrate in vacuo furnished the crude reaction product as an orange oil. Purification by column chromatography ($SiO_2$, 9:1 (v/v) Hex:EtOAc to EtOAc) afforded methyl 1-(4-(trifluoromethyl)benzyl)-1H-benzo[d] imidazole-7-carboxylate as an orange oil (31% yield).

Methyl 1-(4-(trifluoromethyl)benzyl)-1H-benzo[d]imidazole-7-carboxylate (1 eq.) was dissolved in a 2:1 (v/v) solution (0.04 M) of THF and methanol and LiOH was added (3 eq., 2 N aq. solution). The solution was stirred at rt for 16 h and then neutralized with HCl (3 eq., 1 N aq. solution). The volatiles were removed in vacuo and the solid residue was triturated in water to afford 1-(4-(trifluoromethyl)benzyl)-1H-benzo[d]imidazole-7-carboxylic acid as a white, crystalline solid (58% yield).

Intermediate acid 8: 1-((4-(trifluoromethyl)phenyl)-methyl-d$_2$)-1H-indole-7-carboxylic Acid

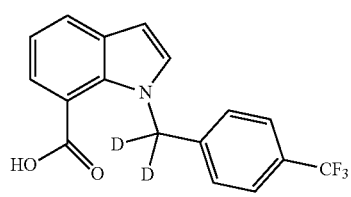 [SMILES: [2H]C([2H])(c1ccc(C(F)(F)F)cc1)n1ccc2cccc(C(=O)O)c21]

Methyl 4-(trifluoromethyl)benzoate (1 eq.) was dissolved in THF (0.3 M) and cooled to 0° C. Lithium aluminum deuteride (1 eq.) was added and the resulting suspension was warmed slowly to rt over 16 h. The reaction was cooled to 0° C. and quenched with 1 N aq. HCl and then extracted with DCM. The combined organic extracts were then washed further with water and brine, dried over MgSO₄ and filtered. Concentration of the filtrate in vacuo furnished the crude reaction product as a colorless oil. Purification by column chromatography (SiO₂, Hex to 3:7 (v/v) Hex:EtOAc) afforded (4-(trifluoromethyl)phenyl)-methan-d₂-ol as a colorless oil (61% yield).

(4-(trifluoromethyl)phenyl)-methan-d₂-ol (1 eq.) and triethylamine (1.5 eq.) were combined in DCM (0.39 M), cooled to 0° C., and methanesulfonyl chloride (1.2 eq.) was added dropwise. The resulting solution stirred at 0° C. for 30 min and then at rt for 1.5 h. The reaction mixture was then diluted with TBME and washed sequentially with water, 1 N aq. NaOH, 1 N aq. HCl, water and finally brine. The organic extract was then dried over MgSO₄ and filtered. Concentration of the filtrate in vacuo furnished the desired crude ((4-(trifluoromethyl)phenyl)-methyl-d₂)-methanesulfonate as a colorless oil (>99% yield).

Methyl 1H-indole-7-carboxylate (1 eq.) was dissolved in DMF (0.32 M) and cooled to 0° C. Potassium tert-butoxide (1.2 eq.) was added over 20 min such that the internal reaction temperature does not exceed 5° C. The resulting suspension was stirred at 0° C. for 30 min, at rt for 30 min, then cooled back to 0° C. ((4-(trifluoromethyl)phenyl)-methyl-d₂)-methanesulfonate (1.2 eq.) from the previous step was added dropwise as a DMF (0.2 M) solution. The resulting reaction mixture was warmed slowly to rt over 16 h and then quenched with deuterium oxide and extracted with EtOAc. The combined organic extracts were washed further with water, 10% aq. NaHCO₃ and brine, dried over MgSO₄, and filtered. Concentration of the filtrate in vacuo furnished the crude reaction product as a viscous oil. Purification by column chromatography (SiO₂, 9:1 (v/v) Hex:EtOAc to EtOAc) afforded methyl 1-((4-(trifluoromethyl)phenyl)-methyl-d₂)-1H-indole-7-carboxylate as a colorless oil (59% yield).

Methyl 1-((4-(trifluoromethyl)phenyl)-methyl-d₂)-1H-indole-7-carboxylate (1 eq.) was dissolved in a 2:1 (v/v) solution (0.1 M) of THF and methanol and LiOH (3 eq., 2 N aq. solution) was added. The resulting solution was heated at 50° C. for 3 h, cooled to rt and then neutralized with HCl (3 eq., 1 N aq. solution). The resulting suspension was filtered and the solid cake rinsed with a cold 1:1 (v/v) solution of methanol and water. The product 1-((4-(trifluoromethyl)phenyl)-methyl-d₂)-1H-indole-7-carboxylic acid was dried in vacuo for 16 h, providing a crystalline solid (61% yield).

Intermediate acid 9: 4-fluoro-1-(4-(trifluoromethyl)benzyl)-1H-indole-7-carboxylic Acid

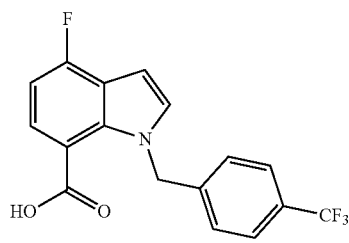 [SMILES: O=C(O)c1ccc(F)c2ccn(Cc3ccc(C(F)(F)F)cc3)c12]

Prepared in an analogous fashion to Intermediate acid 1, but using methyl 4-fluoro-1H-indole-7-carboxylate (1 eq.) in place of methyl 1H-indole-7-carboxylate; and 1-(bromomethyl)-4-(trifluoromethyl)benzene (1.2 eq.) in place of 4-(bromomethyl)benzonitrile.

Intermediate acid 10: 5-fluoro-1-(4-(trifluoromethyl)benzyl)-1H-indole-7-carboxylic Acid

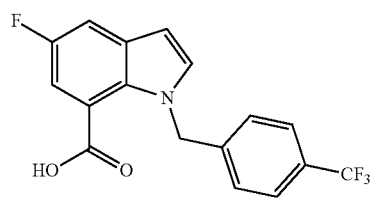 [SMILES: O=C(O)c1cc(F)cc2ccn(Cc3ccc(C(F)(F)F)cc3)c12]

Prepared in an analogous fashion to Intermediate acid 1, but using methyl 5-fluoro-1H-indole-7-carboxylate (1 eq.) in place of methyl 1H-indole-7-carboxylate; and 1-(bromomethyl)-4-(trifluoromethyl)benzene (1.2 eq.) in place of 4-(bromomethyl)benzonitrile.

Intermediate acid 11: 5-chloro-1-(4-(trifluoromethyl)benzyl)-1H-indole-7-carboxylic Acid

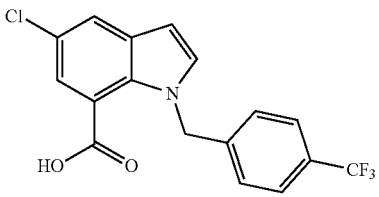 [SMILES: O=C(O)c1cc(Cl)cc2ccn(Cc3ccc(C(F)(F)F)cc3)c12]

Prepared in an analogous fashion to Intermediate acid 1, but using methyl 5-chloro-1H-indole-7-carboxylate (1 eq.) in place of methyl 1H-indole-7-carboxylate; and 1-(bromomethyl)-4-(trifluoromethyl)benzene (1.2 eq.) in place of 4-(bromomethyl)benzonitrile.

Intermediate acid 12: 6-fluoro-1-(4-(trifluoromethyl)benzyl)-1H-indole-7-carboxylic Acid

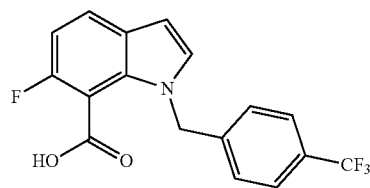 [SMILES: O=C(O)c1c(F)ccc2ccn(Cc3ccc(C(F)(F)F)cc3)c12]

Prepared in an analogous fashion to Intermediate acid 1, but using methyl 6-fluoro-1H-indole-7-carboxylate (1 eq.) in place of methyl 1H-indole-7-carboxylate; and 1-(bromomethyl)-4-(trifluoromethyl)benzene (1.2 eq.) in place of 4-(bromomethyl)benzonitrile.

Intermediate acid 13: 1-(4-(difluoromethyl)benzyl)-1H-indole-7-carboxylic Acid

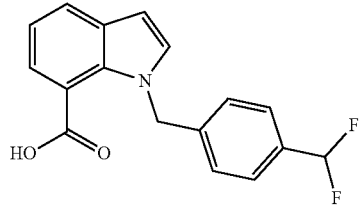 [SMILES: O=C(O)c1cccc2ccn(Cc3ccc(C(F)F)cc3)c12]

Prepared in an analogous fashion to Intermediate acid 1, but using 1-(chloromethyl)-4-(difluoromethyl)benzene (1.2 eq.) in place of 4-(bromomethyl)benzonitrile.

Intermediate acid 14: 1-(4-(difluoromethyl)benzyl)-4-fluoro-1H-indole-7-carboxylic Acid

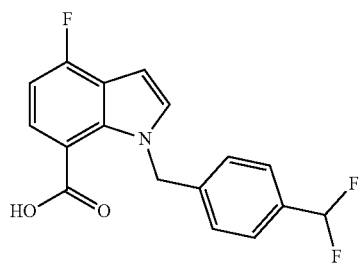 [SMILES: O=C(O)c1ccc(F)c2ccn(Cc3ccc(C(F)F)cc3)c12]

Prepared in an analogous fashion to Intermediate acid 1, but using methyl 4-fluoro-1H-indole-7-carboxylate (1 eq.) in place of methyl 1H-indole-7-carboxylate; and 1-(chloromethyl)-4-(difluoromethyl)benzene (1.2 eq.) in place of 4-(bromomethyl)benzonitrile.

Intermediate acid 15: 1-(4-(pentafluoro-$\lambda^6$-sulfaneyl)benzyl)-1H-indole-7-carboxylic Acid

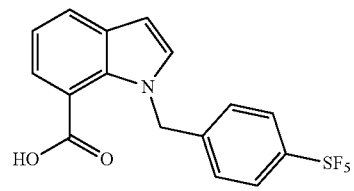

Prepared in an analogous fashion to Intermediate acid 1, but using 4-(pentafluorothio)benzyl bromide (1.2 eq.) in place of 4-(bromomethyl)benzonitrile.

Intermediate acid 16: 1-([1,1'-biphenyl]-4-ylmethyl)-1H-indole-7-carboxylic Acid

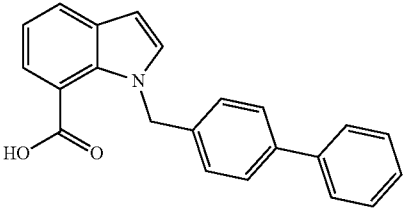 [SMILES: O=C(O)c1cccc2ccn(Cc3ccc(-c4ccccc4)cc3)c12]

Prepared in an analogous fashion to Intermediate acid 1, but using 4-(bromomethyl)-1,1'-biphenyl (1.2 eq.) in place of 4-(bromomethyl)benzonitrile.

Intermediate acid 17: 1-([1,1'-biphenyl]-4-ylmethyl)-4-fluoro-1H-indole-7-carboxylic Acid

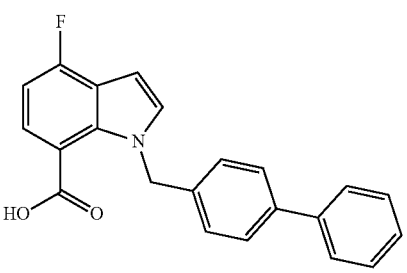 [SMILES: O=C(O)c1ccc(F)c2ccn(Cc3ccc(-c4ccccc4)cc3)c12]

Prepared in an analogous fashion to Intermediate acid 1, but using methyl 4-fluoro-1H-indole-7-carboxylate (1 eq.) in place of methyl 1H-indole-7-carboxylate; and 4-(bromomethyl)-1,1'-biphenyl (1.2 eq.) in place of 4-(bromomethyl)benzonitrile.

Intermediate acid 18: 1-([1,1'-biphenyl]-4-ylmethyl)-1H-indazole-7-carboxylic Acid

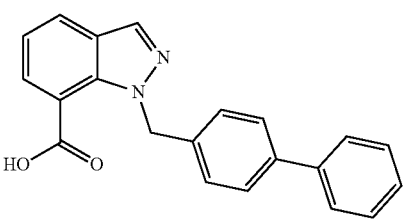 [SMILES: O=C(O)c1cccc2cnn(Cc3ccc(-c4ccccc4)cc3)c12]

Prepared in an analogous fashion to Intermediate acid 6, but using 4-(bromomethyl)-1,1'-biphenyl (1.2 eq.) in place of 1-(bromomethyl)-4-(trifluoromethyl)benzene.

Intermediate acid 19: 1-(4-(trifluoromethoxy)benzyl)-1H-indazole-7-carboxylic Acid

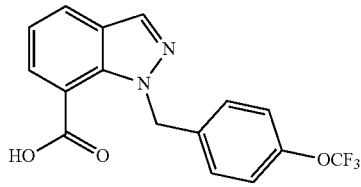 [SMILES: O=C(O)c1cccc2cnn(Cc3ccc(OC(F)(F)F)cc3)c12]

Prepared in an analogous fashion to Intermediate acid 6, but using 1-(bromomethyl)-4-(trifluoromethoxy)benzene (1.2 eq.) in place of 1-(bromomethyl)-4-(trifluoromethyl)benzene.

Intermediate acid 20: 4-fluoro-1-(4-iodobenzyl)-1H-indole-7-carboxylic Acid

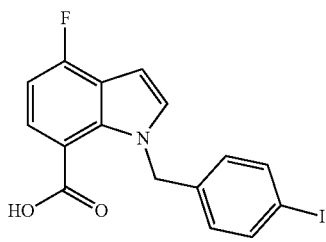 [SMILES: O=C(O)c1ccc(F)c2ccn(Cc3ccc(I)cc3)c12]

Prepared in an analogous fashion to Intermediate acid 1, but using methyl 4-fluoro-1H-indole-7-carboxylate (1 eq.) in place of methyl 1H-indole-7-carboxylate; and 1-(bromomethyl)-4-iodobenzene (1.2 eq.) in place of 4-(bromomethyl)benzonitrile.

Intermediate amine 1: ethyl 2-(3-aminobicyclo[1.1.1]pentan-1-yl)acetate Hydrochloride

3-(methoxycarbonyl)bicyclo[1.1.1]pentan-1-carboxylic acid (1 eq.) was dissolved in tert-butanol (0.25 M) and triethylamine (1 eq.) and diphenylphosphoryl azide (1.5 eq.) were added sequentially. The resulting solution was stirred at RT for 1 h and then heated at 80° C. for 22 h. The volatiles were then removed in vacuo and the resulting residue was taken up in EtOAc. The organic layer was then washed sequentially with water and brine, dried over MgSO$_4$, and filtered. Concentration of the filtrate in vacuo furnished the crude reaction product as a viscous oil. Purification by column chromatography (SiO$_2$, 9:1 (v/v) Hex:EtOAc to 1:1 (v/v) Hex:EtOAc) afforded methyl 3-((tert-butoxycarbonyl)amino)bicyclo[1.1.1]pentan-1-carboxylate as a white, crystalline solid (79% yield).

Methyl 3-((tert-butoxycarbonyl)amino)bicyclo[1.1.1]pentan-1-carboxylate (1 eq.) was dissolved in THF (0.13 M), the solution cooled to 0° C. and LiBH$_4$ (10 eq., 1 M THF solution) was added dropwise. The resulting mixture was warmed slowly to rt over 18 h, quenched with 10% aq. NH$_4$Cl and the volatiles were removed in vacuo. The resulting aqueous residue was then diluted further with water and extracted with EtOAc and Me-THF. The combined organic extracts were then washed further with water and brine, dried over MgSO$_4$, filtered and the filtrate concentrated in vacuo. Purification by column chromatography (SiO$_2$, 9:1 (v/v) Hex:EtOAc to 3:7 (v/v) Hex:EtOAc) afforded tert-butyl (3-(hydroxymethyl)bicyclo[1.1.1]pentan-1-yl)carbamate as a white, crystalline solid (78% yield).

tert-butyl (3-(hydroxymethyl)bicyclo[1.1.1]pentan-1-yl)carbamate (1 eq.) and triethylamine (1.5 eq.) were combined in DCM (0.21 M), cooled to 0° C., and methanesulfonyl chloride (1.2 eq.) was added dropwise. The resulting solution stirred at 0° C. for 30 min and then at rt for 18 h. The reaction mixture was then diluted with EtOAc and washed sequentially with water and brine. The organic extract was then dried over MgSO$_4$ and filtered. Concentration of the filtrate in vacuo furnished the desired crude (3-((tert-butoxycarbonyl)amino)bicyclo[1.1.1]pentan-1-yl)methyl methanesulfonate as a white crystalline solid (99% yield).

(3-((tert-butoxycarbonyl)amino)bicyclo[1.1.1]pentan-1-yl)methyl methanesulfonate (1 eq.) and KCN (2 eq.) were combined in DMF (0.075 M) and heated at 70° C. for 24 h. The crude reaction mixture was cooled to rt, diluted with TBME, and washed sequentially with water and brine. The organic extract was then dried over MgSO$_4$ and filtered. Concentration of the filtrate in vacuo furnished the crude tert-butyl (3-(cyanomethyl)bicyclo[1.1.1]pentan-1-yl)carbamate as a pale yellow oil (92% yield).

tert-butyl (3-(cyanomethyl)bicyclo[1.1.1]pentan-1-yl)carbamate (1 eq.) was dissolved in ethanol (0.14 M) and bubbled with gaseous HCl (with cooling) for 10 min. The reaction vessel was then tightly sealed and heated at 75° C. for 48 h, and then cooled to rt and carefully vented. Water (10 eq.) was added, and the reaction mixture was stirred at rt for 3 h. The volatiles were removed in vacuo and the resulting residue was triturated in ethanol and DCM for 30 min, filtered, and the filtrate was then concentrated in vacuo to furnish the desired, crude ethyl 2-(3-aminobicyclo[1.1.1]pentan-1-yl)acetate hydrochloride as a hygroscopic solid (93% yield).

Intermediate Amine 2: 2-(3-(chloro-λ$^5$-azaneyl)bicyclo[1.1.1]pentan-1-yl)acetonitrile

tert-butyl (3-(cyanomethyl)bicyclo[1.1.1]pentan-1-yl)carbamate (1 eq., Intermediate amine 1, Step 4) was dissolved in DCM (0.071 M), cooled to 0° C., and HCl (30 eq., 4 M dioxane solution) was added dropwise. The resulting solution was stirred at 0° C. for 30 min and then at rt for 2 h. The volatiles were removed in vacuo to furnish the title compound as a pale yellow foam (99% yield).

Intermediate amine 3: ethyl 2-(4-aminobicyclo[2.1.1]hexan-1-yl)acetate Hydrochloride

4-((tert-butoxycarbonyl)amino)bicyclo[2.1.1]hexane-1-carboxylic acid (1 eq.) and triethylamine (1.5 eq.) were dissolved in THF (0.22 M), cooled to −15° C., and ethyl chloroformate (1.5 eq.) was added dropwise. The resulting mixture was stirred at −15° C. for 3 h, diluted with TBME and washed sequentially with water and brine. The organic extract was then dried over MgSO$_4$, filtered and the filtrate concentrated in vacuo. The crude mixed anhydride intermediate was taken up in methanol (0.22 M), cooled to 0° C., and LiBH$_4$ (6 eq.) was added portion-wise over a period of 30 min. The resulting mixture was warmed slowly to rt over 16 h and quenched with 10% aq. NH$_4$Cl. The volatiles were removed in vacuo, and the resulting aqueous residue was diluted further with water and extracted with EtOAc. The combined organic extracts were then washed further with water and brine, dried over MgSO$_4$, filtered and the filtrate concentrated in vacuo. Purification by column chromatography (SiO$_2$, 9:1 (v/v) Hex:EtOAc to 3:7 (v/v) Hex:EtOAc) afforded tert-butyl (4-(hydroxymethyl)bicyclo[2.1.1]hexan-1-yl)carbamate as a white, crystalline solid (88% yield).

tert-butyl (4-(hydroxymethyl)bicyclo[2.1.1]hexan-1-yl)carbamate (1 eq.) and triethylamine (1.5 eq.) were combined in DCM (0.13 M), cooled to 0° C., and methanesulfonyl chloride (1.2 eq.) was added dropwise. The resulting solution was stirred at 0° C. for 30 min and at rt for 18 h, diluted with EtOAc and washed sequentially with water and brine. The organic extract was dried over MgSO$_4$ and filtered. Concentration of the filtrate in vacuo furnished crude 4-(((tert-butoxycarbonyl)amino)bicyclo[2.1.1]hexan-1-yl) methyl methanesulfonate as a white crystalline solid (99% yield).

(4-((tert-butoxycarbonyl)amino)bicyclo[2.1.1]hexan-1-yl)methyl methanesulfonate (1 eq.) and KCN (2 eq.) were combined in DMF (0.055 M) and heated at 80° C. for 24 h. The crude reaction mixture was cooled to rt, diluted with TBME, and washed sequentially with water and brine. The organic extract was then dried over MgSO$_4$ and filtered. Concentration of the filtrate in vacuo furnished crude tert-butyl (4-(cyanomethyl)bicyclo[2.1.1]hexan-1-yl)carbamate as a pale yellow oil (99% yield).

tert-butyl (4-(cyanomethyl)bicyclo[2.1.1]hexan-1-yl)carbamate (1 eq.) was dissolved in ethanol (0.05 M), and gaseous HCl was bubbled in with cooling for 10 min. The reaction vessel was tightly sealed and heated at 80° C. for 48 h, cooled to rt and carefully vented. Water (10 eq.) was added and the mixture was stirred at rt for 2 h. The volatiles were removed in vacuo and the resulting residue was triturated in ethanol and DCM for 30 min, filtered, and the filtrate concentrated in vacuo to furnish the desired, crude product as a hygroscopic solid (96% yield).

EXAMPLES

While preferred embodiments of the present disclosure have been shown and described herein, it will be obvious to those skilled in the art that such embodiments are provided by way of example only. Numerous variations, changes, and substitutions will now occur to those skilled in the art without departing from the present disclosure. It should be understood that various alternatives to the embodiments of the present disclosure described herein may be employed in practicing the present disclosure. It is intended that the following claims define the scope of the present disclosure and that methods and structures within the scope of these claims and their equivalents be covered thereby.

Example 1: 2-(3-(1-(4-cyanobenzyl)-1H-indole-7-carboxamido)bicyclo[1.1.1]pentan-1-yl) acetic Acid

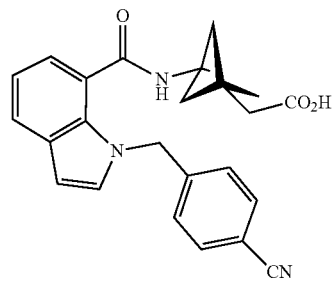

Step 1: ethyl 2-(3-(1-(4-cyanobenzyl)-1H-indole-7-carboxamido)bicyclo pentan-1-yl)acetate: Intermediate acid 1 (1 eq.), Intermediate amine 1 (1.5 eq.) and HATU (1.5 eq.) were dissolved in DMF (0.09 M). To this was then added ethyl-diisopropyl-amine (3 eq.) and the resulting yellow solution was allowed to stir at RT for 18 h. The crude reaction mixture was diluted with EtOAc and washed sequentially with water, 10% aq. NaHCO$_3$, 10% aq. NH$_4$Cl, water and brine. The organic extract was dried over MgSO$_4$, filtered and the filtrate concentrated in vacuo. Further purification by column chromatography (SiO$_2$, 1:1 (v/v) Hex:EtOAc to EtOAc) furnished the product as a pale yellow solid (54% yield).

Step 2: 2-(3-(1-(4-cyanobenzyl)-1H-indole-7-carboxamido)bicyclo[1.1.1] pentan-1-yl)acetic acid: Ethyl 2-(3-(1-(4-cyanobenzyl)-1H-indole-7-carboxamido)bicyclo[1.1.1]pentan-1-yl)acetate (1 eq.) from the previous step was dissolved in a 2:1 (v/v) solution (0.02 M) of THF and methanol, LiOH (5 eq., 2 N aq. solution) was added and the resulting solution was heated at 50° C. for 4 h. The reaction mixture was cooled to RT and then neutralized with HCl (5 eq., 1 N aq. solution). The volatiles were then removed in vacuo and the resulting residue was directly subjected to reverse-phase column chromatography (C$_{18}$, 9:1 (v/v) H$_2$O:MeCN+0.1% formic acid to MeCN+0.1% formic acid). Fractions with the product were combined and concentrated in vacuo. The resulting aqueous suspension was then neutralized with sat. aq. NaHCO$_3$ and extracted with EtOAc. The combined organic extracts were washed further with water and brine, dried over MgSO$_4$, and filtered. Concentration of the filtrate in vacuo afforded, after a further trituration in toluene, the product as a white, crystalline solid (77% yield). ESI$^+$: M+1: 400. ESI$^-$: M−1: 398.

Example 2: 2-(3-(1-(4-(trifluoromethyl)benzyl)-1H-indole-7-carboxamido)bicyclo[1.1.1] pentan-1-yl) acetic Acid

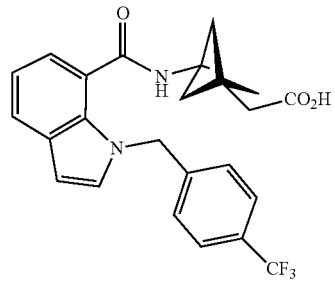

Prepared in an analogous fashion to Example 1, but using Intermediate acid 2 (1 eq.) in place of Intermediate acid 1 in Step 1. ESI+: M+1: 443. ESI−: M−1: 441.

Example 3: 2-(3-(1-(4-(trifluoromethyl)benzyl)-1H-pyrrolo[3,2-b]pyridine-7-carboxamido) bicyclo [1.1.1]pentan-1-yl)acetic Acid

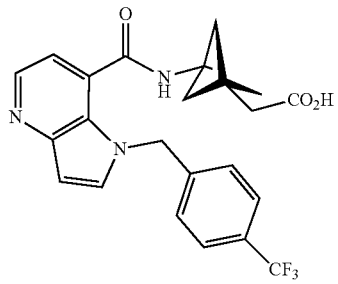

Prepared in an analogous fashion to Example 1, but using Intermediate acid 3 (1 eq.) in place of Intermediate acid 1 in Step 1. ESI+: M+1: 444. ESI−: M−1: 442.

Example 4: 2-(3-(1-(4-(trifluoromethyl)benzyl)-1H-pyrrolo[3,2-c]pyridine-7-carboxamido) bicyclo[1.1.] pentan-1-yl)acetic Acid

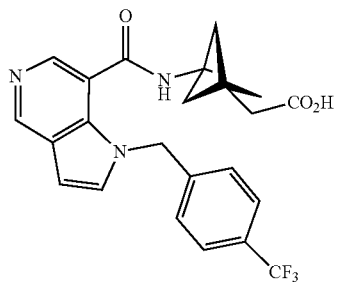

Prepare in an analogous fashion to Example 1, but using Intermediate acid 4 (1 eq.) in place of Intermediate acid 1 in Step 1. ESI+: M+1: 444. ESI−: M−1: 442.

Example 5: 2-(3-(1-(4-(trifluoromethyl)benzyl)-1H-pyrrolo[2,3-c]pyridine-7-carboxamido) bicyclo [1.1.1]pentan-1-yl)acetic Acid

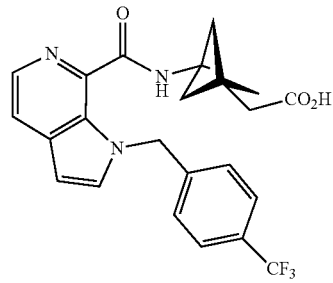

Prepared in an analogous fashion to Example 1, but using Intermediate acid 5 (1 eq.) in place of Intermediate acid 1 in Step 1. ESI+: M+1: 444. ESI−: M−1: 442.

Example 6: 2-(3-(1-(4-(trifluoromethyl)benzyl)-1H-indazole-7-carboxamido)bicyclo[1.1.1] pentan-1-yl) acetic Acid

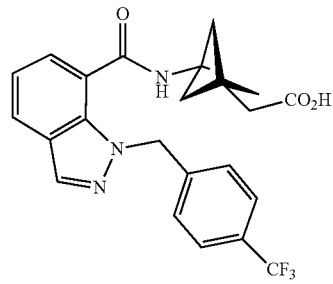

Prepared in an analogous fashion to Example 1, but using Intermediate acid 6 (1 eq.) in place of Intermediate acid 1 in Step 1. ESI+: M+1: 444. ESI−: M−1: 442.

Example 7: 2-(3-(1-((4-(trifluoromethyl)phenyl) methyl-d$_2$)-1H-indole-7-carboxamido) bicyclo [1.1.1]pentan-1-yl)acetic Acid

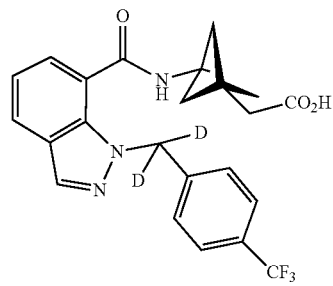

Prepared in an analogous fashion to Example 1, but using Intermediate acid 8 (1 eq.) in place of Intermediate acid 1 in Step 1. ESI+: M+1: 445. ESI−: M−1: 443.

Example 8: (R)-6-(1-(4-(trifluoromethyl)benzyl)-1H-indole-7-carboxamido)spiro[3.3]heptane-2-carboxylic Acid and (S)-6-(1-(4-(trifluoromethyl)benzyl)-1H-indole-7-carboxamido)spiro[3.3]heptane-2-carboxylic Acid (Enantiomer 8a and Enantiomer 8b)

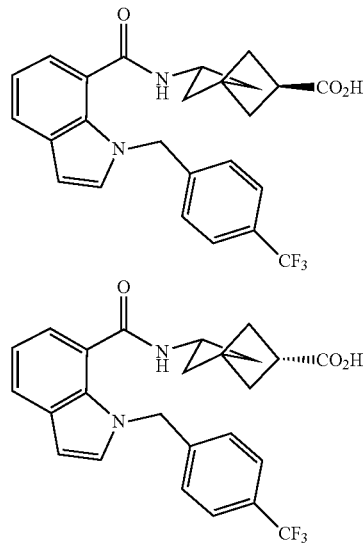

Prepared in an analogous fashion to Example 1, but using Intermediate acid 2 (1 eq.) in place of Intermediate acid 1 and rac-methyl 6-aminospiro[3.3]heptane-2-carboxylate hydrochloride (1.5 eq.) in place of Intermediate amine 1 in Step 1. The racemic product from Step 2 was further resolved by chiral SFC (stationary phase: AD 10×250 mm, 5 μm; mobile phase: 25% methanol, 100 Bar of $CO_2$; column temperature: 35° C.; flow rate: 10 mL/min) into its two enantio-enriched (>99% e.e.) antipodes. First eluting enantiomer; RT: 3.16 min, ESI$^+$: M+1: 457. ESI$^-$: M−1: 455. Second eluting enantiomer; RT: 5.32 min, ESI$^+$: M+1: 457. ESI$^-$: M−1: 455.

Example 9: rac-6-(1-(4-(trifluoromethyl)benzyl)-1H-pyrrolo[3,2-b]pyridine-7-carboxamido) spiro[3.3]heptane-2-carboxylic Acid

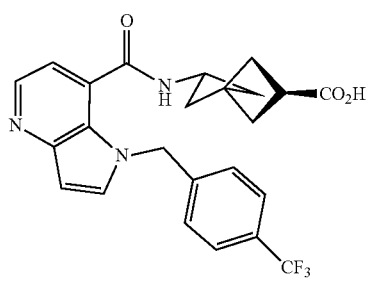

Prepared in an analogous fashion to Example 1, but using Intermediate acid 3 (1 eq.) in place of Intermediate acid 1 and rac-methyl 6-aminospiro[3.3]heptane-2-carboxylate hydrochloride (1.5 eq.) in place of Intermediate amine 1 in Step 1. ESI$^+$: M+1: 458. ESI$^-$: M−1: 456.

Example 10: (R)-6-(1-(4-(trifluoromethyl)benzyl)-1H-pyrrolo[3,2-c]pyridine-7-carboxamido) spiro[3.3]heptane-2-carboxylic Acid and (S)-6-(1-(4-(trifluoromethyl)benzyl)-1H-pyrrolo[3,2-c]pyridine-7-carboxamido) spiro[3.3]heptane-2-carboxylic Acid (Enantiomer 10a and Enantiomer 10b)

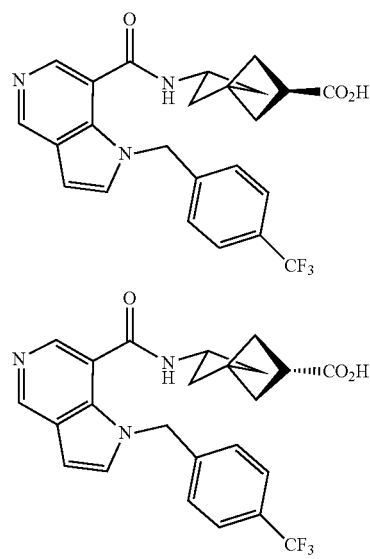

Prepared in an analogous fashion to Example 1, but using Intermediate acid 4 (1 eq.) in place of Intermediate acid 1 and rac-methyl 6-aminospiro[3.3]heptane-2-carboxylate hydrochloride (1.5 eq.) in place of Intermediate amine 1 in Step 1. ESI$^+$: M+1: 458. ESI$^-$: M−1: 456. The racemic product from Step 2 was further resolved by chiral SFC (stationary phase: OJ 10×250 mm, 5 μm; mobile phase: 25% methanol, 100 Bar of $CO_2$; column temperature: 35° C.; flow rate: 10 mL/min) into its two enantio-enriched (>99% e.e.) antipodes. First eluting enantiomer; RT: 3.10 min, ESI$^+$: M+1: 458. ESI$^-$: M−1: 456. Second eluting enantiomer; RT: 4.60 min, ESI$^+$: M+1: 458. ESI$^-$: M−1: 456.

Example 11: rac-6-(1-(4-(trifluoromethyl)benzyl)-1H-pyrrolo[2,3-c]pyridine-7-carboxamido)spiro[3.3]heptane-2-carboxylic Acid

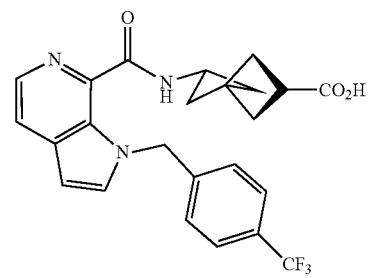

Prepared in an analogous fashion to Example 1, but using Intermediate acid 5 (1 eq.) in place of Intermediate acid 1 and rac-methyl 6-aminospiro[3.3]heptane-2-carboxylate hydrochloride (1.5 eq.) in place of Intermediate amine 1 in Step 1. ESI+: M+1: 458. ESI−: M−1: 456.

Example 12: rac-6-(1-(4-(trifluoromethyl)benzyl)-1H-indazole-7-carboxamido)spiro[3.3]heptane-2-carboxylic Acid

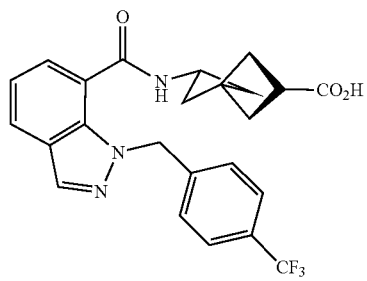

Prepared in an analogous fashion to Example 1, but using Intermediate acid 6 (1 eq.) in place of Intermediate acid 1 and rac-methyl 6-aminospiro[3.3]heptane-2-carboxylate hydrochloride (1.5 eq.) in place of Intermediate amine 1 in Step 1. ESI+: M+1: 458. ESI−: M−1: 456.

Example 13: rac-6-(1-(4-(trifluoromethyl)benzyl)-1H-benzo[d]imidazole-7-carboxamido) spiro[3.3]heptane-2-carboxylic Acid

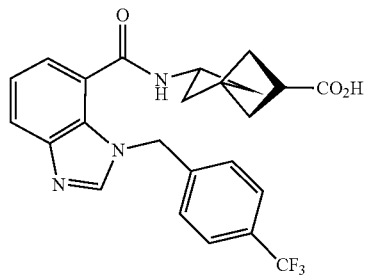

Prepared in an analogous fashion to Example 1, but using Intermediate acid 7 (1 eq.) in place of Intermediate acid 1 and rac-methyl 6-aminospiro[3.3]heptane-2-carboxylate hydrochloride (1.5 eq.) in place of Intermediate amine 1 in Step 1. ESI+: M+1: 458. ESI−: M−1: 456.

Example 14: 3-(3-(1-(4-(trifluoromethyl)benzyl)-1H-indole-7-carboxamido)bicyclo[1.1.1] pentan-1-yl)propanoic Acid Example 15: cis-3-(3-methyl-3-(1-(4-(trifluoromethyl)benzyl)-1H-indole-7-carboxamido) cyclobutyl) propanoic Acid

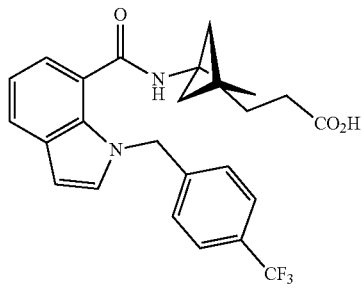

Example 14

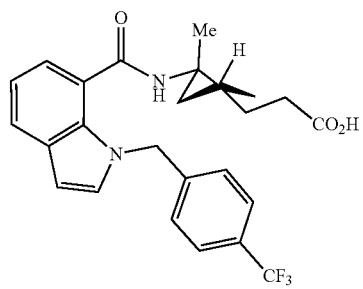

Example 15

Step 1: tert-butyl (3-formylbicyclo[1.1.1]pentan-1-yl)carbamate: tert-butyl (3-(hydroxymethyl)bicyclo[1.1.1]pentan-1-yl)carbamate (1 eq., Intermediate amine 1, Step 2) and sodium bicarbonate (1.5 eq.) were suspended in DCM (0.034 M). Dess-Martin periodinane (1.2 eq.) was added to the reaction mixture and stirred at RT for 1.5 h. The reaction mixture was then diluted with TBME and washed sequentially with 10% aq. Na$_2$S$_2$O$_3$, 1 N aq. NaOH, water and brine. The organic extract was then dried over MgSO$_4$ and filtered. Concentration of the filtrate in vacuo furnished the desired crude product as a white crystalline solid (68% yield).

Step 2: (E)-methyl 3-(3-((tert-butoxycarbonyl)amino)bicyclo[1.1.1] pentan-1-yl)acrylate: tert-butyl (3-formylbicyclo[1.1.1]pentan-1-yl)carbamate (1 eq.) from the previous step was dissolved in THF (0.034 M) and methyl 2-(triphenylphosphoranylidene)acetate (1 eq.) was added. The resulting solution was stirred at RT for 18 h and then diluted with TBME and washed sequentially with 1 N aq. HCl, water and brine. The organic extract was then dried over MgSO$_4$ and filtered. Concentration of the filtrate in vacuo furnished the crude reaction product as a viscous oil. Further purification by way of column chromatography (SiO$_2$, 9:1 (v/v) Hex:EtOAc to 3:7 (v/v) Hex:EtOAc) afforded the product as a colorless oil (94% yield).

Step 3: methyl 3-(3-((tert-butoxycarbonyl)amino)bicyclo[1.1.1]pentan-1-yl)propanoate and cis-methyl 3-(3-((tert-butoxycarbonyl)amino)-3-methylcyclobutyl) propanoate: (E)-methyl 3-(3-((tert-butoxycarbonyl)amino)bicyclo[1.1.1] pentan-1-yl)acrylate (1 eq.) from the previous step and palladium (0.06 eq., 10% (w/w) over carbon, dry) were mixed in a 1:1 (v/v) solution (0.032 M) of methanol and EtOAc. The resulting suspension was then deoxygenated with nitrogen for 10 min and the reaction vessel was evacuated and back-filled with hydrogen and stirred at RT under a balloon of hydrogen for 2 h. The reaction was then quenched with DCM and the resulting suspension was filtered through celite. Concentration of the filtrate in vacuo furnished a 1.7:1 mixture of methyl 3-(3-((tert-butoxycarbonyl)amino)bicyclo[1.1.1]pentan-1-yl)propanoate and cis-methyl 3-(3-((tert-butoxycarbonyl)amino)-3-methylcyclobutyl)propanoate as a white foam (81% yield).

Step 4: methyl 3-(3-aminobicyclo[1.1.1]pentan-1-yl)propanoate hydrochloride and cis-methyl 3-(3-amino-3-methylcyclobutyl)propanoate hydrochloride: The mixture of methyl 3-(3-((tert-butoxycarbonyl)amino)bicyclo[1.1.1]pentan-1-yl)propanoate and cis-methyl 3-(3-((tert-butoxycarbonyl)amino)-3-methylcyclobutyl)propanoate (1 eq.) from the previous step was dissolved in DCM (0.051 M) and HCl (10 eq., 4 M dioxane solution) was added dropwise at 0° C. The resulting solution was stirred at 0° C. for 30 min and then at RT for 4 h. The volatiles were then evaporated in vacuo to furnish a 1.7:1 mixture of methyl 3-(3-aminobicyclo[1.1.1]pentan-1-yl)propanoate hydrochloride and cis-methyl 3-(3-amino-3-methylcyclobutyl)propanoate hydrochloride as a white foam (99% yield).

Step 5: methyl 3-(3-(1-(4-(trifluoromethyl)benzyl)-1H-indole-7-carboxamido)bicyclo[1.1.1]pentan-1-yl)propanoate and cis-methyl 3-(3-methyl-3-(1-(4-(trifluoromethyl)benzyl)-1H-indole-7-carboxamido)cyclobutyl)propanoate: Intermediate acid 2 (1 eq.), the mixture of methyl 3-(3-aminobicyclo[1.1.1]pentan-1-yl)propanoate hydrochloride and cis-methyl 3-(3-amino-3-methylcyclobutyl)propanoate hydrochloride (1.5 eq.) from the previous step, and HATU (1.5 eq.) were dissolved in DMF (0.13 M). Ethyl-diisopropyl-amine (3 eq.) was added and the resulting solution stirred at RT for 18 h. The crude reaction mixture was diluted with EtOAc and washed sequentially with water, 10% aq. NaHCO$_3$, 10% aq. NH$_4$Cl, water and brine. The organic extract was then dried over MgSO$_4$, filtered and the filtrate concentrated in vacuo. Purification by column chromatography (SiO$_2$, 1:1 (v/v) Hex:EtOAc to EtOAc) furnished a 1.7:1 mixture of methyl 3-(3-(1-(4-(trifluoromethyl)benzyl)-1H-indole-7-carboxamido)bicyclo[1.1.1]pentan-1-yl)propanoate and cis-methyl 3-(3-methyl-3-(1-(4-(trifluoromethyl)benzyl)-1H-indole-7-carboxamido)cyclobutyl)propanoate as a pale yellow foam (67% yield).

Step 6: 3-(3-(1-(4-(trifluoromethyl)benzyl)-1H-indole-7-carboxamido)bicyclo[1.1.1]pentan-1-yl)propanoic acid and cis-3-(3-methyl-3-(1-(4-(trifluoromethyl)benzyl)-1H-indole-7-carboxamido)cyclobutyl)propanoic acid: The mixture of methyl 3-(3-(1-(4-(trifluoromethyl)benzyl)-1H-indole-7-carboxamido)bicyclo[1.1.1] pentan-1-yl)propanoate and cis-methyl 3-(3-methyl-3-(1-(4-(trifluoromethyl)benzyl)-1H-indole-7-carboxamido)cyclobutyl)propanoate (1 eq.) from the previous step were dissolved in a 2:1 (v/v) solution (0.057 M) of THF and methanol and LiOH (3 eq., 2 N aq. solution) was added. The resulting solution was stirred at RT for 16 h and neutralized with HCl (3 eq., 1 N aq. solution). The volatiles were then removed in vacuo and the resulting residue was directly subjected to purification by way of chiral SFC (stationary phase: AD 10×250 mm, 5 µm; mobile phase: 25% methanol, 100 Bar of CO$_2$; column temperature: 35° C.; flow rate: 10 mL/min). Second eluting peak: 3-(3-(1-(4-(trifluoromethyl)benzyl)-1H-indole-7-carboxamido)bicyclo[1.1.1]pentan-1-yl)propanoic acid, Example 14, ESI$^+$: M+1: 459. ESI$^-$: M−1: 457. First eluting peak: cis-3-(3-methyl-3-(1-(4-(trifluoromethyl)benzyl)-1H-indole-7-carboxamido)cyclobutyl)propanoic acid, Example 15, ESI$^+$: M+1: 459. ESI$^-$: M−1: 457.

Example 16: N-(3-(2-oxo-2-(phenylsulfonamido)ethyl)bicyclo[1.1.1]pentan-1-yl)-1-(4-(trifluoromethyl)benzyl)-1H-indole-7-carboxamide

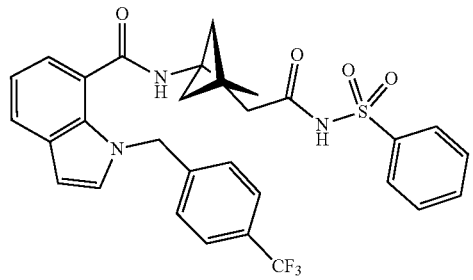

2-(3-(1-(4-(trifluoromethyl)benzyl)-1H-indole-7-carboxamido)bicyclo [1.1.1]pentan-1-yl)acetic acid (1 eq., Example 2), EDCI (1.4 eq.), benzenesulfonamide (1.4 eq.) and DMAP (1.4 eq.) were combined in DCM (0.019 M). Ethyl-diisopropyl-amine (1.4 eq.) was added and the resulting solution was stirred at RT for 18 h. The reaction mixture was then diluted with EtOAc and washed sequentially with 1 N aq. HCl, water and brine. The organic extract was then dried over MgSO$_4$ and filtered. Concentration of the filtrate in vacuo furnished the crude reaction product as an off-white solid. Further purification by column chromatography (SiO$_2$, 9:1 (v/v) Hex:EtOAc to EtOAc to 10:1 (v/v) EtOAc:MeOH) afforded the title compound as a white powder (30% yield). ESI$^+$: M+1: 582. ESI$^-$: M−1: 580.

Example 17: N-(3-((3-(phenylsulfonyl)ureido)methyl)bicyclo[1.1.1]pentan-1-yl)-1-(4-(trifluoromethyl)benzyl)-1H-indole-7-carboxamide

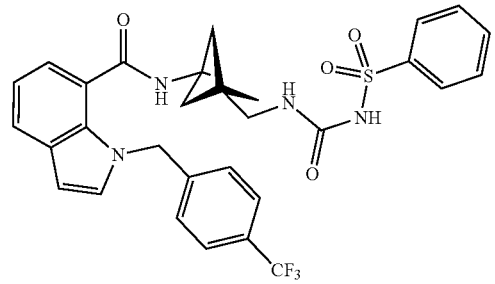

Step 1: methyl 3-(1-(4-(trifluoromethyl)benzyl)-1H-indole-7-carboxamido)bicyclo[1.1.1]pentane-1-carboxylate: Intermediate acid 2 (1 eq.), methyl 3-aminobicyclo[1.1.1]pentane-1-carboxylate hydrochloride (1.5 eq.) and HATU (1.5 eq.) were dissolved in DMF (0.09 M) and ethyl-diisopropyl-amine (3 eq.) was added. The resulting solution stirred at RT for 18 h, diluted with EtOAc and washed sequentially with water, 10% aq. NaHCO$_3$, 10% aq. NH$_4$Cl, water and brine. The organic extract was then dried over MgSO$_4$, filtered and the filtrate concentrated in vacuo. Purification by column chromatography (SiO$_2$, 1:1 (v/v) Hex:EtOAc to EtOAc) furnished the product as a pale yellow solid (71% yield).

Step 2: 3-(1-(4-(trifluoromethyl)benzyl)-1H-indole-7-carboxamido) bicyclo[1.1.1]pentane-1-carboxylic acid: methyl 3-(1-(4-(trifluoromethyl)benzyl)-1H-indole-7-carboxamido)bicyclo[1.1.1]pentane-1-carboxylate (1 eq.) from the previous step was dissolved in a 2:1 (v/v) solution (0.03 M) of THF and methanol and LiOH (5 eq., 2 N aq. solution) was added. The resulting solution was stirred at 50° C. for 18 h, cooled to RT and neutralized with HCl (5 eq., 1 N aq. solution). The volatiles were then removed in vacuo and the resulting residue was directly subjected to reverse-phase column chromatography ($C_{18}$, 9:1 (v/v) $H_2O$:MeCN+0.1% formic acid to MeCN+0.1% formic acid). Fractions with the product were combined and concentrated in vacuo. The resulting aqueous suspension was then neutralized with the addition of sat. aq. NaHCO$_3$ and extracted with EtOAc. The combined organic extracts were washed further with water and brine, dried over MgSO$_4$, and filtered. Concentration of the filtrate in vacuo afforded the product as a white, crystalline solid (55% yield).

Step 3: N-(3-(hydroxymethyl)bicyclo[1.1.1]pentan-1-yl)-1-(4-(trifluoromethyl)benzyl)-1H-indole-7-carboxamide: 3-(1-(4-(trifluoromethyl)benzyl)-1H-indole-7-carboxamido)bicyclo[1.1.1]pentane-1-carboxylic acid (1 eq.) from the previous step and triethylamine (1.5 eq.) were dissolved in THF (0.12 M), the solution was cooled to −15° C. and ethyl chloroformate (1.5 eq.) was added dropwise. The reaction mixture was stirred at −15° C. for 3 h, diluted with TBME and washed sequentially with water and brine. The organic extract was then dried over MgSO$_4$, filtered and the filtrate concentrated in vacuo. The crude mixed anhydride intermediate was taken up in methanol (0.12 M) and LiBH$_4$ (6 eq.) was added at 0° C. The resulting mixture was then warmed slowly to RT over 16 h, quenched with 10% aq. NH$_4$Cl and the volatiles were removed in vacuo. The resulting aqueous residue was then diluted further with water and extracted with EtOAc. The combined organic extracts were washed further with water and brine, dried over MgSO$_4$, filtered and the filtrate concentrated in vacuo. Purification by column chromatography (SiO$_2$, 4:1 (v/v) Hex:EtOAc to EtOAc) afforded the product as a white foam (60% yield).

Step 4: (3-(1-(4-(trifluoromethyl)benzyl)-1H-indole-7-carboxamido) bicyclo[1.1.1]pentan-1-yl)methyl methanesulfonate: N-(3-(hydroxymethyl)bicyclo[1.1.1]pentan-1-yl)-1-(4-(trifluoromethyl)benzyl)-1H-indole-7-carboxamide (1 eq.) from the previous step and triethylamine (1.5 eq.) were dissolved in DCM (0.087 M) and methanesulfonyl chloride (1.2 eq.) was added dropwise at 0° C. The resulting solution was stirred at 0° C. for 30 min and then at RT for 18 h. The reaction mixture was then diluted with EtOAc and washed sequentially with water and brine. The organic extract was then dried over MgSO$_4$ and filtered. Concentration of the filtrate in vacuo furnished the desired crude product as a pale yellow foam (89% yield).

Step 5: N-(3-(azidomethyl)bicyclo[1.1.1]pentan-1-yl)-1-(4-(trifluoromethyl)benzyl)-1H-indole-7-carboxamide: (3-(1-(4-(trifluoromethyl)benzyl)-1H-indole-7-carboxamido)bicyclo[1.1.1]pentan-1-yl)methyl methanesulfonate (1 eq.) from the previous step and sodium azide (2 eq.) were combined in DMF (0.12 M) and heated at 80° C. for 24 h. The crude reaction mixture was then cooled to RT, diluted with EtOAc, and washed sequentially with water and brine. The organic extract was then dried over MgSO$_4$, filtered and the filtrate concentrated in vacuo. Purification by column chromatography (SiO$_2$, 4:1 (v/v) Hex:EtOAc to EtOAc) afforded the product as a white, crystalline solid (47% yield).

Step 6: N-(3-(aminomethyl)bicyclo[1.1.1]pentan-1-yl)-1-(4-(trifluoromethyl)benzyl)-1H-indole-7-carboxamide: N-(3-(azidomethyl)bicyclo[1.1.1]pentan-1-yl)-1-(4-(trifluoromethyl)benzyl)-1H-indole-7-carboxamide (1 eq.) from the previous step and triphenylphosphine (1.5 eq.) were combined in a 3:1 (v/v) solution (0.028 M) of THF and water. The resulting mixture was heated at 45° C. for 48 h, cooled to RT and directly subjected to purification by rpHPLC (C$_{18}$, 9:1 (v/v) H$_2$O:MeCN+0.1% formic acid to MeCN+0.1% formic acid). Fractions with the product were combined and concentrated in vacuo. The resulting aqueous suspension was then neutralized with 1 N aq. NaOH and extracted with DCM. The combined organic extracts were washed further with water and brine, dried over MgSO$_4$, and filtered. Concentration of the filtrate in vacuo afforded the product as a colorless oil (77% yield).

Step 7: N-(3-((3-(phenylsulfonyl)ureido)methyl)bicyclo[1.1.1]pentan-1-yl)-1-(4-(trifluoromethyl)benzyl)-1H-indole-7-carboxamide: N-(3-(aminomethyl)bicyclo [1.1.1] pentan-1-yl)-1-(4-(trifluoromethyl)benzyl)-1H-indole-7-carboxamide (1 eq.) from the previous step was dissolved in DCM (0.042 M) and benzenesulfonyl isocyanate (1.1 eq.) was added. The resulting mixture was stirred at RT for 18 h, the volatiles were removed in vacuo and the resulting residue was directly subjected to purification by rpHPLC (C$_{18}$, 9:1 (v/v) H$_2$O:MeCN+0.1% formic acid to MeCN+0.1% formic acid). Fractions with the product were combined and concentrated in vacuo to afford the title compound as a white foam (52% yield). ESI$^+$: M+1: 597. ESI$^-$: M−1: 595.

Example 18: N-(3-((1H-tetrazol-5-yl)methyl)bicyclo [1.1.1]pentan-1-yl)-1-(4-(trifluoro methyl)benzyl)-1H-indole-7-carboxamide

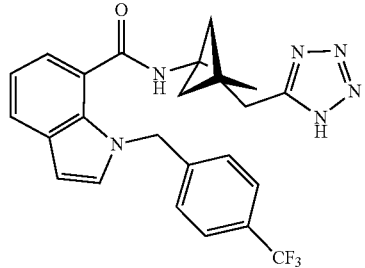

Step 1: N-(3-(cyanomethyl)bicyclo[1.1.1]pentan-1-yl)-1-(4-(trifluoromethyl)benzyl)-1H-indole-7-carboxamide: Intermediate acid 2 (1 eq.), Intermediate amine 2 (1.5 eq.) and HATU (1.5 eq.) were dissolved in DMF (0.55 M). and ethyl-diisopropyl-amine (3 eq.) was added. The resulting solution was stirred at RT for 18 h, diluted with TBME and washed sequentially with water, 1 N aq. NaOH, water and brine. The organic extract was then dried over MgSO$_4$, filtered and the filtrate concentrated in vacuo. Purification by column chromatography (SiO$_2$, 9:1 (v/v) Hex:EtOAc to EtOAc) furnished the product as a white, crystalline solid (62% yield).

Step 2: N-(3-((1H-tetrazol-5-yl)methyl)bicyclo[1.1.1]pentan-1-yl)-1-(4-(trifluoromethyl)benzyl)-1H-indole-7-carboxamide: N-(3-(cyanomethyl)bicyclo[1.1.1] pentan-1-yl)-1-(4-(trifluoromethyl)benzyl)-1H-indole-7-carboxamide (1 eq.) from the previous step, sodium azide (2 eq.) and dibutyltin(IV) oxide (0.1 eq.) were combined in a 1:1 (v/v)

solution (0.052 M) of NMP and water. The reaction vessel was tightly sealed and heated behind a blast shield at 110° C. for 1 week. The resulting mixture was cooled to RT and then directly subjected to rpHPLC ($C_{18}$, 9:1 (v/v) $H_2O$: MeCN+0.1% formic acid to MeCN+0.1% formic acid). Fractions with the product were combined and concentrated in vacuo to afford the title compound as a white foam (45% yield). ESI⁺: M+1: 467. ESI⁻: M−1: 465.

Example 19: 2-(4-(1-(4-(trifluoromethyl)benzyl)-1H-indole-7-carboxamido)bicyclo[2.1.1] hexan-1-yl)acetic Acid

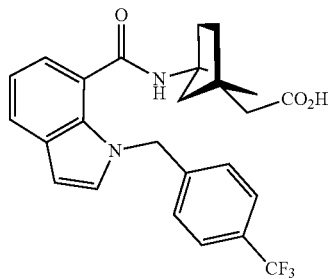

Prepared in an analogous fashion to Example 1, but using Intermediate acid 2 (1 eq.) in place of Intermediate acid 1 and intermediate amine 3 (1.5 eq.) in place of in intermediate amine 1 in Step 1. ESI⁺: M+1: 457. ESI⁻: M−1: 455.

Example 20: (R)-6-(4-fluoro-1-(4-(trifluoromethyl)benzyl)-1H-indole-7-carboxamido)spiro[3.3]heptane-2-carboxylic acid and (S)-6-(4-fluoro-1-(4-(trifluoromethyl)benzyl)-1H-indole-7-carboxamido) spiro[3.3] heptane-2-carboxylic Acid (Enantiomer 20a and Enantiomer 20b)

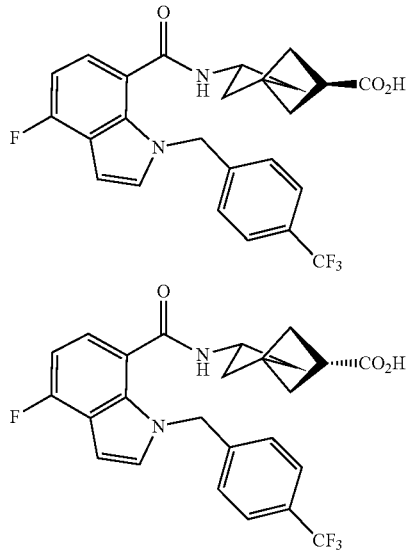

Prepared in an analogous fashion to Example 1, but using Intermediate acid 9 (1 eq.) in place of Intermediate acid 1 and rac-methyl 6-aminospiro[3.3]heptane-2-carboxylate hydrochloride (1.5 eq.) in place of Intermediate amine 1 in Step 1. ESI⁺: M+1: 475. ESI⁻: M−1: 473. The racemic product from Step 2 was further resolved by chiral SFC (stationary phase: AD 10×250 mm, 5 μm; mobile phase: 20% methanol, 100 Bar of $CO_2$; column temperature: 35° C.; flow rate: 10 mL/min) into its two enantio-enriched (>99% e.e.) antipodes. First eluting enantiomer; RT: 3.96 min, ESI⁺: M+1: 475. ESI⁻: M−1: 473. Second eluting enantiomer; RT: 7.66 min, ESI⁺: M+1: 475. ESI⁻: M−1: 473.

Example 21: rac-6-(5-fluoro-1-(4-(trifluoromethyl)benzyl)-1H-indole-7-carboxamido)spiro heptane-2-carboxylic Acid

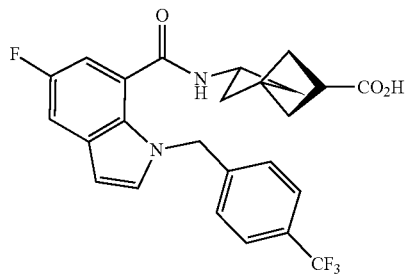

Prepared in an analogous fashion to Example 1, but using Intermediate acid 10 (1 eq.) in place of Intermediate acid 1 and rac-methyl 6-aminospiro[3.3]heptane-2-carboxylate hydrochloride (1.5 eq.) in place of Intermediate amine 1 in Step 1. ESI⁺: M+1: 475. ESI⁻: M−1: 473.

Example 22: rac-6-(5-chloro-1-(4-(trifluoromethyl)benzyl)-1H-indole-7-carboxamido)spiro heptane-2-carboxylic Acid

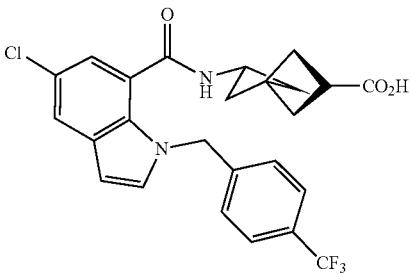

Prepare in an analogous fashion to Example 1, but using Intermediate acid 11 (1 eq.) in place of Intermediate acid 1 and rac-methyl 6-aminospiro[3.3]heptane-2-carboxylate hydrochloride (1.5 eq.) in place of Intermediate amine 1 in Step 1. ESI⁺: M+1: 491. ESI⁻: M−1: 489.

Example 23: rac-6-(6-fluoro-1-(4-(trifluoromethyl)benzyl)-1H-indole-7-carboxamido)spiro heptane-2-carboxylic Acid

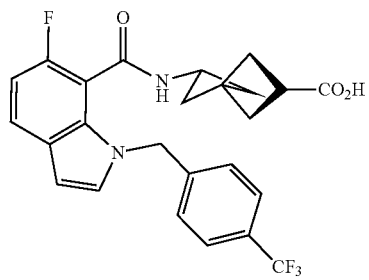

Prepared in an analogous fashion to Example 1, but using Intermediate acid 12 (1 eq.) in place of Intermediate acid 1 and rac-methyl 6-aminospiro[3.3]heptane-2-carboxylate hydrochloride (1.5 eq.) in place of Intermediate amine 1 in Step 1. ESI$^+$: M+1: 475. ESI$^-$: M−1: 473.

Example 24: rac-6-(1-(4-cyanobenzyl)-1H-indole-7-carboxamido)spiro[3.3]heptane-2-carboxylic Acid

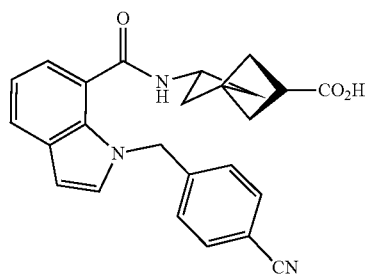

Prepared in an analogous fashion to Example 1, but using rac-methyl 6-aminospiro[3.3]heptane-2-carboxylate hydrochloride (1.5 eq.) in place of Intermediate amine 1 in Step 1. ESI$^+$: M+1: 414. ESI$^-$: M−1: 412.

Example 25: rac-6-(1-(4-(difluoromethyl)benzyl)-1H-indole-7-carboxamido)spiro[3.3] heptane-2-carboxylic Acid

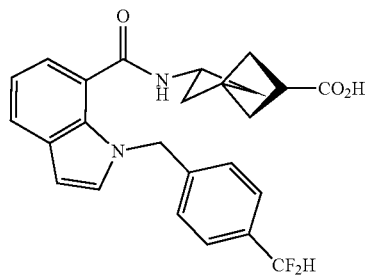

Prepared in an analogous fashion to Example 1, but using Intermediate acid 13 (1 eq.) in place of Intermediate acid 1 and rac-methyl 6-aminospiro[3.3]heptane-2-carboxylate hydrochloride (1.5 eq.) in place of Intermediate amine 1 in Step 1. ESI$^+$: M+1: 439. ESI$^-$: M−1: 437.

Example 26: 2-(4-(1-(4-(difluoromethyl)benzyl)-1H-indole-7-carboxamido)bicyclo[2.1.1] hexan-1-yl)acetic Acid

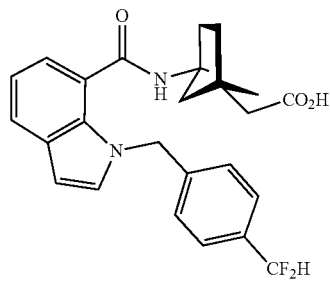

Prepared in an analogous fashion to Example 1, but using Intermediate acid 13 (1 eq.) in place of Intermediate acid 1 and intermediate amine 3 (1.5 eq.) in place of Intermediate amine 1 in Step 1. ESI$^+$: M+1: 439. ESI$^-$: M−1: 437.

Example 27: 2-(3-(4-fluoro-1-(4-(trifluoromethyl)benzyl)-1H-indole-7-carboxamido)bicyclo pentan-1-yl)acetic Acid

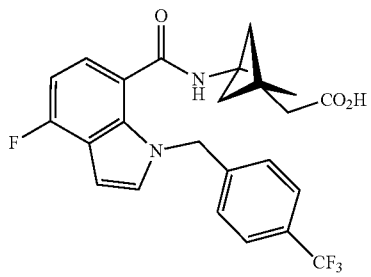

Prepared in an analogous fashion to Example 1, but using Intermediate acid 9 (1 eq.) in place of Intermediate acid 1 in Step 1. ESI$^+$: M+1: 461. ESI$^-$: M−1: 459.

Example 28: 2-(4-(4-fluoro-1-(4-(trifluoromethyl)benzyl)-1H-indole-7-carboxamido)bicyclo hexan-1-yl)acetic Acid

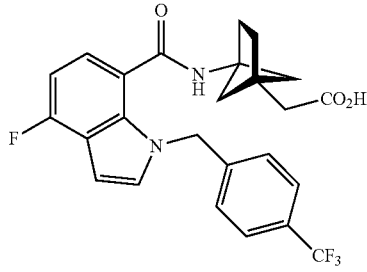

Prepared in an analogous fashion to Example 1, but using Intermediate acid 9 (1 eq.) in place of Intermediate acid 1 and intermediate amine 3 (1.5 eq.) in place of in intermediate amine 1 in Step 1. ESI+: M+1: 475. ESI−: M−1: 473.

Example 29: 2-(4-(1-((4-(pentafluorothiol)phenyl)methyl)-1H-indole-7-carboxamido)bicyclo hexan-1-yl)acetic Acid

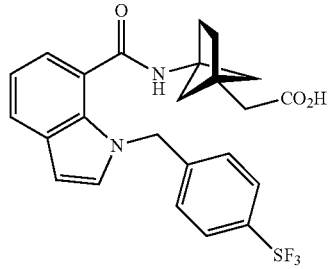

Prepared in an analogous fashion to Example 1, but using Intermediate acid 15 (1 eq.) in place of Intermediate acid 1 and intermediate amine 3 (1.5 eq.) in place of in intermediate amine 1 in Step 1. ESI+: M+1: 515. ESI−: M−1: 513.

Example 30: rac-6-(1-((4-(pentafluorothiol)phenyl)methyl)-1H-indole-7-carboxamido)spiro heptane-2-carboxylic Acid

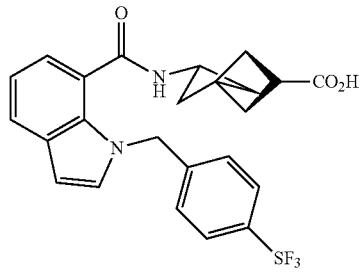

Prepared in an analogous fashion to Example 1, but using Intermediate acid 15 (1 eq.) in place of Intermediate acid 1 and rac-methyl 6-aminospiro[3.3]heptane-2-carboxylate hydrochloride (1.5 eq.) in place of Intermediate amine 1 in Step 1. ESI+: M+1: 515. ESI−: M−1: 513.

Example 31: rac-6-(1-(4-(difluoromethyl)benzyl)-4-fluoro-1H-indole-7-carboxamido)spiro heptane-2-carboxylic Acid

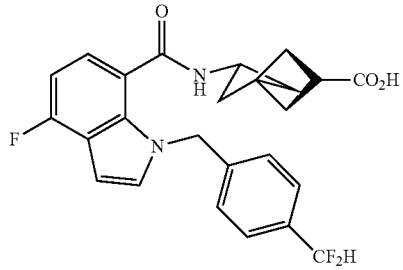

Prepared in an analogous fashion to Example 1, but using Intermediate acid 14 (1 eq.) in place of Intermediate acid 1 and rac-methyl 6-aminospiro[3.3]heptane-2-carboxylate hydrochloride (1.5 eq.) in place of Intermediate amine 1 in Step 1. ESI+: M+1: 457. ESI−: M−1: 455.

Example 32: 2-(3-(1-(4-(difluoromethyl)benzyl)-4-fluoro-1H-indole-7-carboxamido)bicyclo pentan-1-yl)acetic Acid

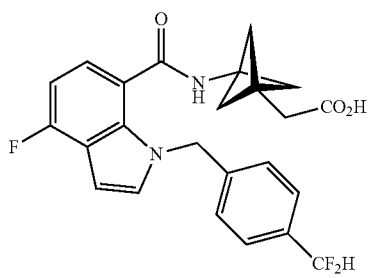

Prepared in an analogous fashion to Example 1, but using Intermediate acid 14 (1 eq.) in place of Intermediate acid 1 in Step 1. ESI+: M+1: 443. ESI−: M−1: 441.

Example 33: 2-(3-(5-fluoro-1-(4-(trifluoromethyl)benzyl)-1H-indole-7-carboxamido)bicyclo pentan-1-yl)acetic Acid

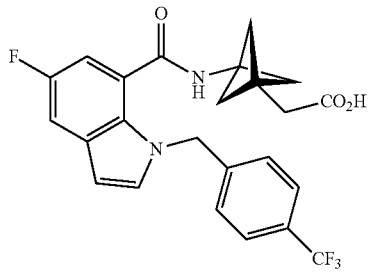

Prepared in an analogous fashion to Example 1, but using Intermediate acid 9 (1 eq.) in place of Intermediate acid 1 in Step 1. ESI+: M+1: 461. ESI−: M−1: 459.

Example 34: 2-(3-(1-([1,1'-biphenyl]-4-ylmethyl)-1H-indole-7-carboxamido)bicyclo[1.1.1] pentan-1-yl)acetic Acid

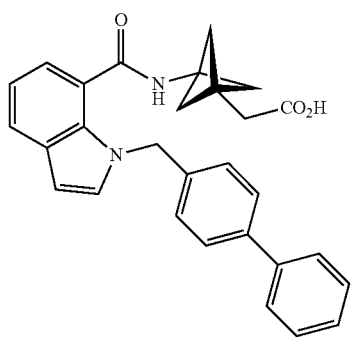

Prepared in an analogous fashion to Example 1, but using Intermediate acid 16 (1 eq.) in place of Intermediate acid 1 in Step 1. ESI+: M+1: 451. ESI−: M−1: 449.

Example 35: 2-(3-(1-([1,1'-biphenyl]-4-ylmethyl)-4-fluoro-1H-indole-7-carboxamido)bicyclo[1.1.11]pentan-1-yl)acetic Acid

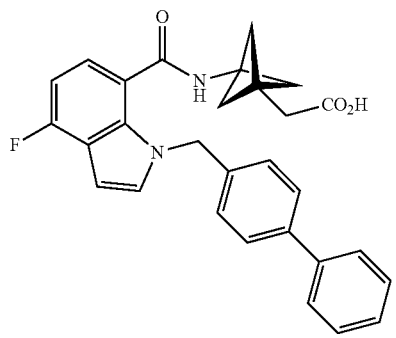

Prepared in an analogous fashion to Example 1, but using Intermediate acid 17 (1 eq.) in place of Intermediate acid 1 in Step 1. ESI+: M+1: 469. ESI−: M−1: 467.

Example 36: 2-(3-(1-([1,1'-biphenyl]-4-ylmethyl)-1H-indazole-7-carboxamido)bicyclo[1.1.1] pentan-1-yl)acetic Acid

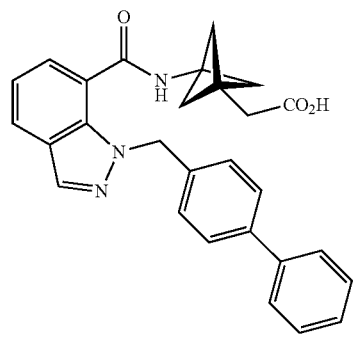

Prepared in an analogous fashion to Example 1, but using Intermediate acid 18 (1 eq.) in place of Intermediate acid 1 in Step 1. ESI+: M+1: 452. ESI−: M−1: 450.

Example 37: 2-(3-(1-(4-(trifluoromethoxy)benzyl)-1H-indazole-7-carboxamido)bicyclo[1.1.1] pentan-1-yl)acetic Acid

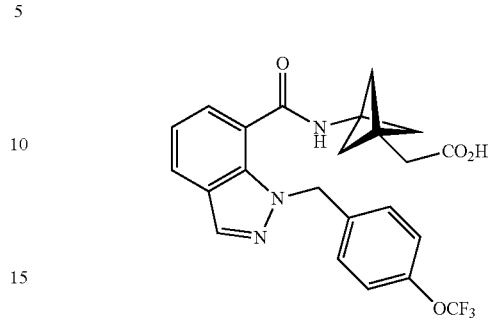

Prepared in an analogous fashion to Example 1, but using Intermediate acid 19 (1 eq.) in place of Intermediate acid 1 in Step 1. ESI+: M+1: 460. ESI−: M−1: 458.

Example 38: 2-(3-(4-fluoro-1-(4-iodobenzyl)-1H-indole-7-carboxamido)bicyclo[1.1.1]pentan-1-yl) acetic Acid

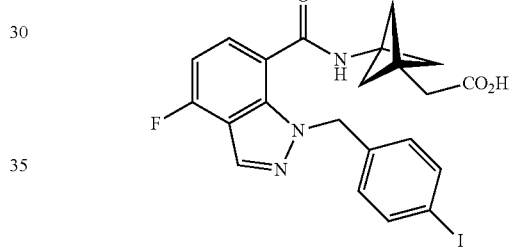

Prepared in an analogous fashion to Example 1, but using Intermediate acid 20 (1 eq.) in place of Intermediate acid 1 in Step 1. ESI+: M+1: 519. ESI−: M−1: 517.

Example 39: 2-(3-(4-fluoro-1-(4-(pyridine-4-yl)benzyl)-1H-indole-7-carboxamido)bicyclo[1.1.1] pentan-1-yl) acetic Acid

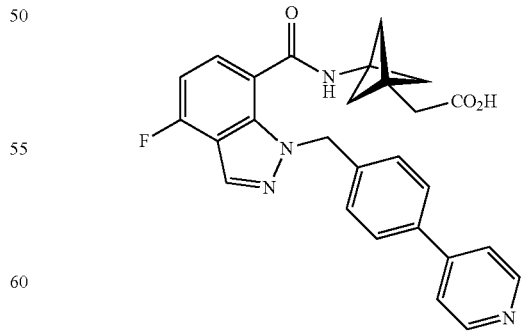

2-(3-(4-Fluoro-1-(4-iodobenzyl)-1H-indole-7-carboxamido)bicyclo [1.1.1]pentan-1-yl)acetic acid (1 eq., Example 38), 4-pyridinylboronic acid (3 eq.), and XPhos-Palladium 3$^{rd}$ generation precatalyst complex (0.1 eq.) were combined in dioxane (0.14 M). The resulting yellow solution was deoxygenated via sub-surface purging with a stream of nitrogen for 15 min. Potassium phosphate (3 eq. 2 N aq. solution) was then added to the reaction mixture and the resulting biphasic solution was further deoxygenated via sub-surface purging with a stream of nitrogen for another 15 min. The reaction vessel was then tightly sealed and heated at 80° C. for 12 h. The resulting mixture was cooled to RT and then directly subjected to rpHPLC ($C_{18}$, 9:1 (v/v) $H_2O$:MeCN+0.1% formic acid to MeCN+0.1% formic acid). Fractions with the product were combined and concentrated in vacuo to afford the title compound as an off-white solid (53% yield). $ESI^+$: M+1: 470. $ESI^-$: M−1: 468.

Example 40: 2-(3-(4-fluoro-1-(4-morpholinobenzyl)-1H-indole-7-carboxamido)bicyclo[1.1.1]pentan-1-yl) acetic Acid

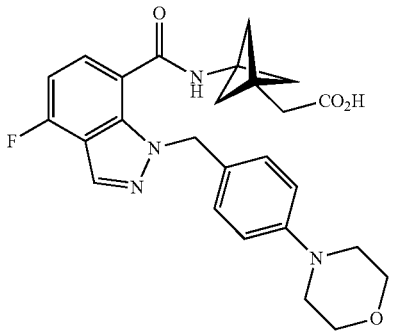

2-(3-(4-Fluoro-1-(4-iodobenzyl)-1H-indole-7-carboxamido)bicyclo [1.1.1]pentan-1-yl)acetic acid (1 eq., Example 38), morpholine (2 eq.), RuPhos-Palladium $2^{nd}$ generation precatalyst complex (0.05 eq.) and sodium tert-pentoxide (2.5 eq.) were combined in dioxane (0.055 M). The resulting orange-red suspension was deoxygenated via sub-surface purging with a stream of nitrogen for 15 min. The reaction vessel was then tightly sealed and heated at 80° C. for 12 h. The resulting mixture was cooled to RT and then directly subjected to rpHPLC ($C_{18}$, 9:1 (v/v) $H_2O$:MeCN+ 0.1% formic acid to MeCN+0.1% formic acid). Fractions with the product were combined and concentrated in vacuo to afford the title compound as an off-white solid (53% yield). $ESI^+$: M+1: 478. $ESI^-$: M−1:476.

The embodiments described above are intended to be merely exemplary and those skilled in the art will recognize, or will be able to ascertain using no more than routine experimentation, numerous equivalents of specific compounds, materials, and procedures. All such equivalents are considered to be within the scope of the claimed subject matter and are encompassed by the appended claims.

What is claimed is:

1. A compound of Formula Ib:

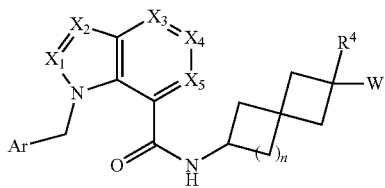

or a pharmaceutically acceptable salt, solvate, solvate of the salt, hydrate, a single stereoisomer, a mixture of stereoisomers, or a racemic mixture of stereoisomers thereof, wherein:

Ar is an aryl or a heteroaryl, wherein said aryl and said heteroaryl are each optionally substituted with 1 to 3 substituents independently selected from $C_1$-$C_6$ alkyl, $C_3$-$C_7$ cycloalkyl, heterocycle, aryl, heteroaryl, halogen, CN, $OR^b$, $SF_5$, and $C_1$-$C_6$ haloalkyl;

W is selected from $C(=O)OR^5$, $C(=O)NHOH$, $S(=O)_2NHR^b$, $S(=O)_2NHC(=O)R^b$, $NHC(=O)NHSO_2R^b$, 1H-tetrazole, and $C(=O)NHS(=O)_2R^b$;

$X^1$, $X^2$, $X^3$, $X^4$, and $X^5$ are each independently N or $CR^a$, wherein not more than 2 of $X^1$, $X^2$, $X^3$, $X^4$, and $X^5$ are N;

$R^4$ is selected from H, $C_1$-$C_6$ alkyl, halogen and $C_1$-$C_6$ haloalkyl;

$R^5$ is selected from H and $C_1$-$C_6$ alkyl;

each $R^a$ is independently selected from H, $C_1$-$C_6$ alkyl, halogen, $OR^b$, CN, $C_3$-$C_6$ cycloalkyl, and $C_1$-$C_6$ haloalkyl;

$R^b$ is selected from H, $C_1$-$C_6$ alkyl, $C_3$-$C_6$ cycloalkyl, and $C_1$-$C_6$ haloalkyl; and n is 1, 2 or 3.

2. The compound of claim 1, or a pharmaceutically acceptable salt, solvate, solvate of the salt, hydrate, a single stereoisomer, a mixture of stereoisomers, or a racemic mixture of stereoisomers thereof, wherein Ar is aryl optionally substituted with 1 to 3 substituents independently selected from halogen, CN, $C_1$-$C_6$ alkyl, $SF_5$, $C_1$-$C_6$ haloalkyl, heterocycle, aryl, heteroaryl, and $OR^b$ wherein $R^b$ is $C_1$-$C_6$ alkyl, $C_3$-$C_6$ cycloalkyl, or $C_1$-$C_6$ haloalkyl.

3. The compound of claim 1, or a pharmaceutically acceptable salt, solvate, solvate of the salt, hydrate, a single stereoisomer, a mixture of stereoisomers, or a racemic mixture of stereoisomers thereof, wherein one of $X^1$, $X^2$, $X^3$, $X^4$ and $X^5$ is N, and the others are each independently C—$R^a$.

4. The compound of claim 1, or a pharmaceutically acceptable salt, solvate, solvate of the salt, hydrate, a single stereoisomer, a mixture of stereoisomers, or a racemic mixture of stereoisomers thereof, wherein W is selected from $C(=O)OR^5$, $S(=O)_2NHR^b$, $S(=O)_2NHC(=O)R^b$, $NHC(=O)NHSO_2R^b$, and 1H-tetrazole.

5. The compound of claim 4, or a pharmaceutically acceptable salt, solvate, solvate of the salt, hydrate, a single stereoisomer, a mixture of stereoisomers, or a racemic mixture of stereoisomers thereof, wherein W is $CO_2H$.

6. The compound of claim 1, or a pharmaceutically acceptable salt, solvate, solvate of the salt, hydrate, a single stereoisomer, a mixture of stereoisomers, or a racemic mixture of stereoisomers thereof, wherein n is 1.

7. The compound of claim 1, or a pharmaceutically acceptable salt, solvate, solvate of the salt, hydrate, a single stereoisomer, a mixture of stereoisomers, or a racemic mixture of stereoisomers thereof, wherein $R^4$ is selected from H, $C_1$-$C_3$ alkyl, and $C_1$-$C_3$ haloalkyl.

8. The compound of claim 7, or a pharmaceutically acceptable salt, solvate, solvate of the salt, hydrate, a single stereoisomer, a mixture of stereoisomers, or a racemic mixture of stereoisomers thereof, wherein $R^4$ is H.

9. The compound of claim 1, or a pharmaceutically acceptable salt, solvate, solvate of the salt, hydrate, a single stereoisomer, a mixture of stereoisomers, or a racemic mixture of stereoisomers thereof, wherein each $R^a$ is independently selected from H, $C_1$-$C_6$ alkyl, halogen, $OR^b$, CN, and $C_1$-$C_6$ haloalkyl.

10. The compound of claim 9, or a pharmaceutically acceptable salt, solvate, solvate of the salt, hydrate, a single stereoisomer, a mixture of stereoisomers, or a racemic mixture of stereoisomers thereof, wherein each $R^a$ is independently selected from H, halogen, $OR^b$, and CN.

11. The compound of claim 1, wherein the compound has the Formula Id:

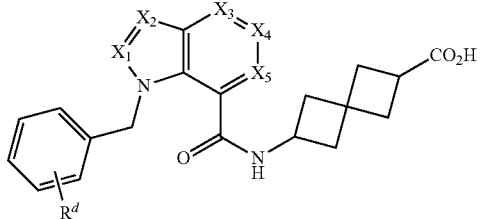

Id or a pharmaceutically acceptable salt, solvate, solvate of the salt, hydrate, a single stereoisomer, a mixture of stereoisomers, or a racemic mixture of stereoisomers thereof, wherein each $X^1$, $X^2$, $X^3$, $X^4$ and $X^5$ is independently C—$R^a$, or one of $X^1$, $X^2$, $X^3$, $X^4$ and $X^5$ is N, and the others are each independently C—$R^a$;

each $R^a$ is independently selected from H and halogen;

$R^d$ is selected from CN, $C_1$-$C_3$ alkyl, $SF_5$, $C_1$-$C_3$ haloalkyl, heterocycle, aryl, heteroaryl, and $OR^b$ wherein $R^b$ is $C_1$-$C_6$ alkyl, $C_3$-$C_6$ cycloalkyl, or $C_1$-$C_6$ haloalkyl.

12. The compound of claim 11, or a pharmaceutically acceptable salt, solvate, solvate of the salt, hydrate, a single stereoisomer, a mixture of stereoisomers, or a racemic mixture of stereoisomers thereof, wherein one of $X^1$, $X^2$, $X^3$, $X^4$ and $X^5$ is C—$R^a$ and the others are CH, and $R^a$ is halogen.

13. The compound of claim 11, or a pharmaceutically acceptable salt, solvate, solvate of the salt, hydrate, a single stereoisomer, a mixture of stereoisomers, or a racemic mixture of stereoisomers thereof, wherein $R^d$ is selected from heterocycle, aryl, and heteroaryl.

14. The compound of claim 13, or a pharmaceutically acceptable salt, solvate, solvate of the salt, hydrate, a single stereoisomer, a mixture of stereoisomers, or a racemic mixture of stereoisomers thereof, wherein $R^d$ is aryl.

15. The compound of claim 1 selected from:

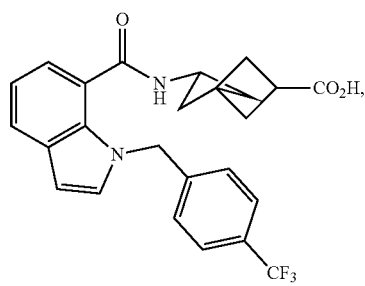

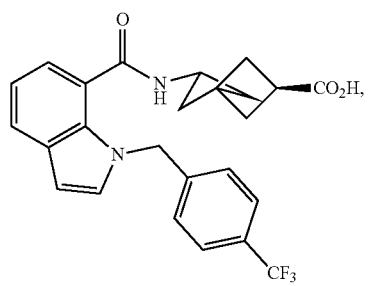

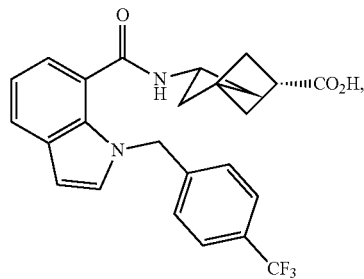

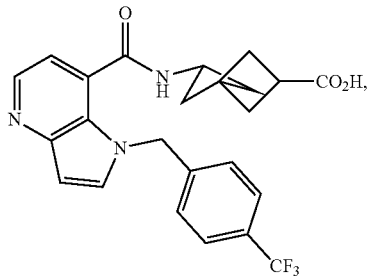

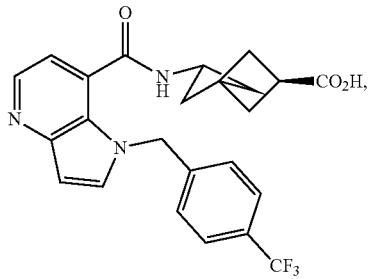

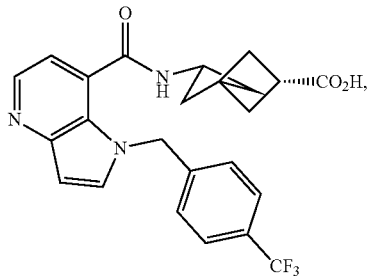

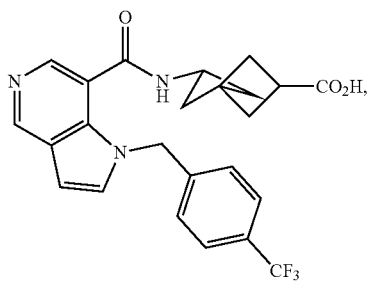

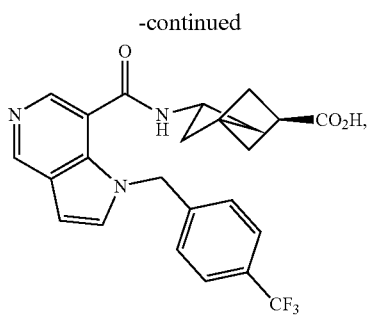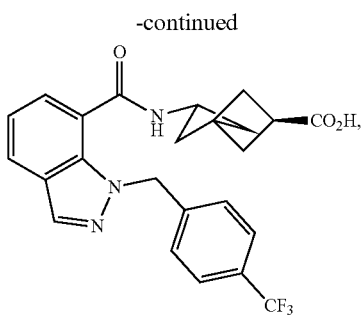

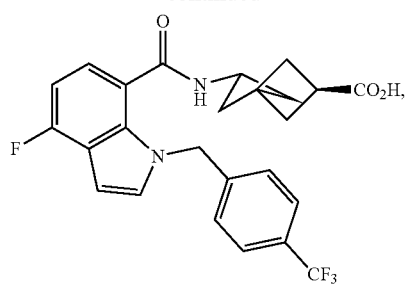
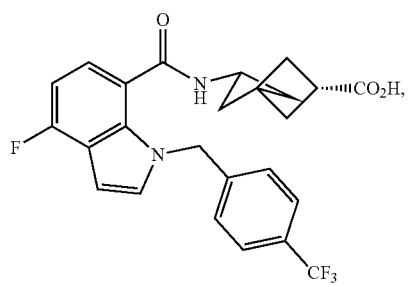
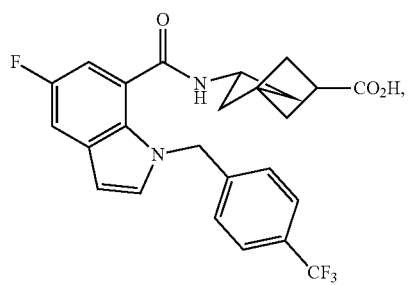
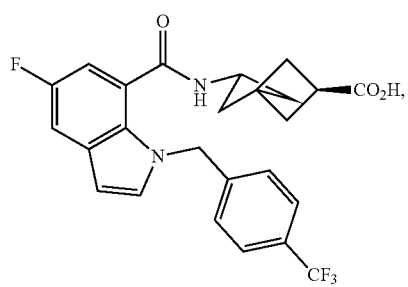
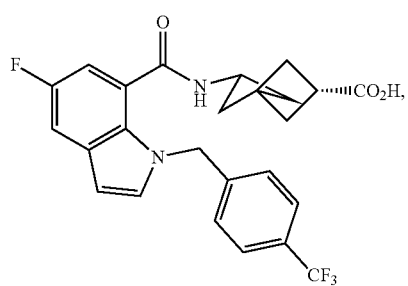
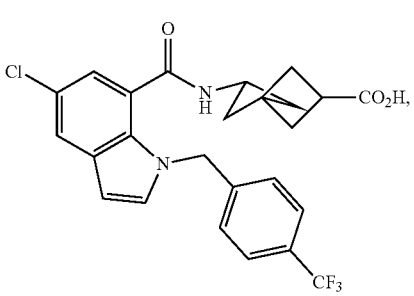
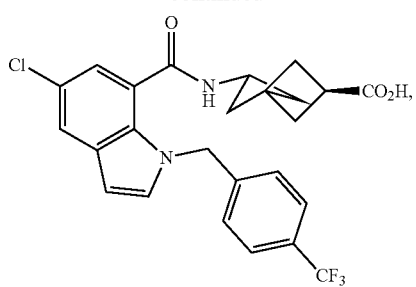
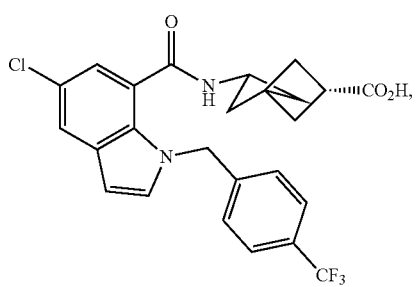
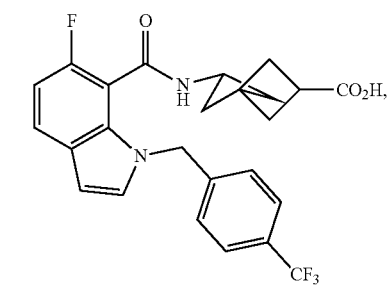
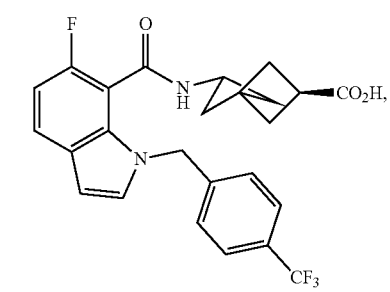
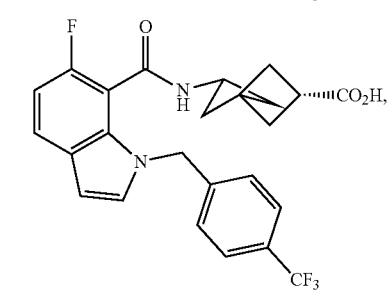
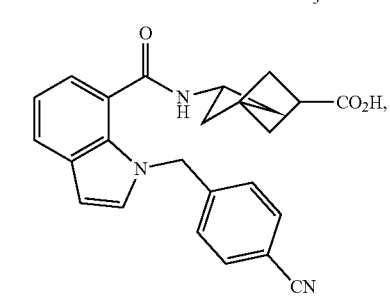

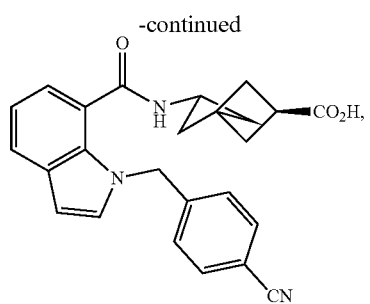

or a pharmaceutically acceptable salt, solvate, or solvate of the salt thereof.

16. A pharmaceutical composition comprising the compound of claim 1, or a pharmaceutically acceptable salt, solvate, solvate of the salt, hydrate, a single stereoisomer, a mixture of stereoisomers, or a racemic mixture of stereoisomers thereof, and a pharmaceutically acceptable carrier.

* * * * *